US009644009B2

(12) United States Patent
Iwatani et al.

(10) Patent No.: US 9,644,009 B2
(45) Date of Patent: May 9, 2017

(54) L-AMINO ACID-PRODUCING BACTERIUM AND A METHOD FOR PRODUCING AN L-AMINO ACID

(75) Inventors: Shintaro Iwatani, Kawasaki (JP); Akira Imaizumi, Kawasaki (JP); Yoshihiro Usuda, Kawasaki (JP); Kazuhiko Matsui, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 1871 days.

(21) Appl. No.: 12/055,438

(22) Filed: Mar. 26, 2008

(65) Prior Publication Data

US 2009/0246835 A1 Oct. 1, 2009

Related U.S. Application Data

(63) Continuation of application No. PCT/JP2006/319821, filed on Sep. 27, 2006.

(60) Provisional application No. 60/723,936, filed on Oct. 6, 2005.

(30) Foreign Application Priority Data

Sep. 27, 2005 (JP) .................................. 2005-279027
Aug. 4, 2006 (JP) .................................. 2006-213584

(51) Int. Cl.
  *C12P 13/04* (2006.01)
  *C07K 14/245* (2006.01)
  *C12P 13/08* (2006.01)
  *C12P 13/22* (2006.01)

(52) U.S. Cl.
  CPC ............ *C07K 14/245* (2013.01); *C12P 13/04* (2013.01); *C12P 13/08* (2013.01); *C12P 13/22* (2013.01)

(58) Field of Classification Search
  None
  See application file for complete search history.

(56) References Cited

U.S. PATENT DOCUMENTS

| | | | |
|---|---|---|---|
| 5,168,056 A | 12/1992 | Frost | |
| 5,776,736 A | 7/1998 | Frost et al. | |
| 5,906,925 A | 5/1999 | Liao | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,045,320 B2 | 5/2006 | Iwatani et al. | |
| 7,060,475 B2 | 6/2006 | Usuda et al. | |
| 7,090,998 B2 | 8/2006 | Ishikawa et al. | |
| 7,192,748 B2 | 3/2007 | Usuda et al. | |
| 7,220,570 B2 | 5/2007 | Usuda et al. | |
| 7,306,933 B2 | 12/2007 | Van Dien et al. | |
| 2002/0155556 A1 | 10/2002 | Imaizumi et al. | |
| 2004/0229305 A1 | 11/2004 | Usuda et al. | |
| 2004/0265956 A1 | 12/2004 | Takikawa et al. | |
| 2005/0106688 A1 | 5/2005 | Imaizumi et al. | |
| 2005/0233308 A1 | 10/2005 | Nishio et al. | |
| 2006/0019356 A1 | 1/2006 | Usuda et al. | |
| 2006/0030010 A1 | 2/2006 | Usuda et al. | |
| 2006/0030011 A1 | 2/2006 | Usuda et al. | |
| 2006/0234356 A1 | 10/2006 | Usuda et al. | |
| 2006/0234357 A1 | 10/2006 | Usuda et al. | |
| 2007/0249017 A1 | 10/2007 | Usuda et al. | |

FOREIGN PATENT DOCUMENTS

| | | |
|---|---|---|
| WO | WO02/081722 | 10/2002 |
| WO | WO03/076636 | 9/2003 |
| WO | WO03/076637 | 9/2003 |

OTHER PUBLICATIONS

Ma, Z., et al., "Characterization of EvgAS-YdeO-GadE Branches Regulatory Circuit Governing Glutamate-Dependent Acid Resistance in *Escherichia coli*," J. Bacteriol. 2004;186(21):7378-7389.
Nishino, K., et al., "Global Analysis of Genes Regulated by EvgA of the Two-Component Regulatory System in *Escherichia coli*," J. Bacteriol. 2003;185(8):2667-2672.
Interntational Search Report and Written Opinion of the International Searching Authority for PCT Patent App. No. PCT/JP2006/319821 (Dec. 11, 2006).
Hommais, F., et al., "GadE (YhiE): a novel activator involved in the response to acid environment in *Escherichia coli*," Microbiol. 2004;150:61-72.
Ma, Z., et al., "Characterization of EvgAS-YdeO-GadE Branched Regulatory Circuit Governing Glutamate-Dependent Acid Resistance in *Escherichia coli*," J. Bacteriol. 2004;186(21):7378-7389.
Ma, Z., et al., "GadE (YhiE) activates glutamate decarboxylase-dependent acid resistance in *Escherichia coli* K-12," Mol. Microbiol. 2003 ;49(5):1309-1320.
Masuda, N., et al., "*Escherichia coli* Gene Expression Responsive to Levels of the Response Regulator EvgA," J. Bacteriol. 2002;184(22):6225-6234.
Masuda, N., et al., "Regulatory network of acid resistance genes in *Escherichia coli*," Mol. Microbiol. 2003;48(3):699-712.
Nishino, K., et al., "Global Analysis of Genes Regulated by EvgA of the Two-Component Regulatory System in *Escherichia coli*," J. Bacteriol. 2003;185(8):2667-2672.

(Continued)

*Primary Examiner* — Richard Hutson
(74) *Attorney, Agent, or Firm* — Shelly Guest Cermak; Cermak Nakajima & McGowan LLP

(57) ABSTRACT

An L-amino acid is produced by culturing a microorganism of the family Enterobacteriaceae which has the ability to produce an L-amino acid and which has been modified so as to increase the expression of the evgA gene, the gadE gene, and/or the ydeO gene. These genes encode a transcription factor involved in the EvgAS two-component system regulon. The culture takes place in a medium, and the L-amino acid is collected from the medium or cells.

11 Claims, 1 Drawing Sheet

(56) References Cited

OTHER PUBLICATIONS

International Preliminary Report on Patentability and Written Opinion of the Internation Searching Authority for PCT Patent App. No. PCT/JP2006/319821 (Apr. 10, 2008).
U.S. Appl. No. 11/877,726, Van Dien et al., filed Oct. 24, 2007.

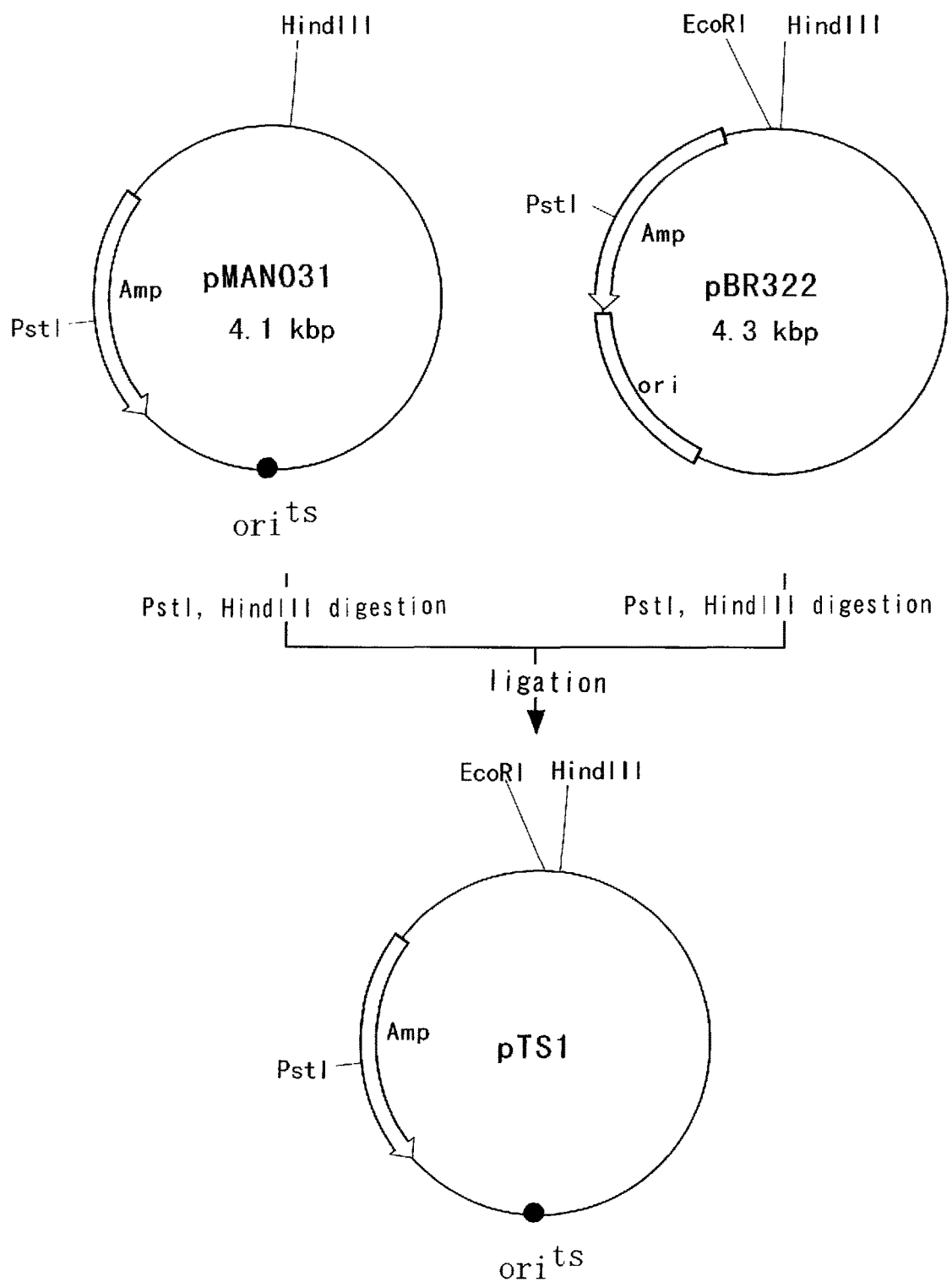

L-AMINO ACID-PRODUCING BACTERIUM AND A METHOD FOR PRODUCING AN L-AMINO ACID

The present application claims priority under 35 U.S.C. §119 to Japanese Patent Application No. 2005-279027, filed Sep. 27, 2005, U.S. Provisional Patent Application No. 60/723,936, filed Oct. 6, 2005, and Japanese Patent Application No. 2006-213584, filed Aug. 4, 2006, and is a continuation under 35 U.S.C. §120 of PCT/JP2006/319821, filed Sep. 27, 2006, the entirety of both of which is incorporated by reference. Also, the Sequence Listing on compact disk filed herewith is hereby incorporated by reference (File name: US-254 Seq List; File size: 132 KB; Date recorded: Mar. 26, 2008).

BACKGROUND OF THE INVENTION

Technical Field

The present invention relates to a method for producing an L-amino acid using a microorganism, and more specifically, to a method for producing an L-amino acid, such as L-lysine, L-threonine, L-tryptophan, etc. L-lysine, L-threonine, and L-tryptophan are used in industry as animal feed additives, health food ingredients, and for amino acid infusions.

Brief Description of the Related Art

To produce a target substance, such as an L-amino acid, etc., by fermentation using a microorganism, methods have been described which use a wild-type microorganism (wild-type strain), an auxotrophic strain derived from a wild-type strain, a metabolic regulation mutant strain as one of various types of drug-resistant mutant strains derived from a wild-type strain, a strain which has the characteristics of both the auxotrophic strain and metabolic regulation mutant strain, and so forth.

In recent years, recombinant DNA technology has been used to produce target substances by fermentation. For example, the ability of a microorganism to produce an L-amino acid has been improved by enhancing the expression of genes that encode L-amino acid biosynthesis enzymes (U.S. Pat. No. 5,168,056, U.S. Pat. No. 5,776,736), or by enhancing the influx of the carbon source to the L-amino acid biosynthesis system (U.S. Pat. No. 5,906,925).

The two-component system EvgAS has been identified in Enterobacteriaceae, such as *Escherichia coli*, etc. The function of the sensor kinase EvgS is unknown, but the response regulator transcription factor EvgA is known to regulate the transcription of many genes (Masuda, N. and Church, G. M., J. Bacteriol. 2002. 184(22):6225-6234. *Escherichia coli* gene expression responsive to levels of the response regulator EvgA.). EvgA is also known to positively regulate the transcription of the ydeO and gadE genes, which encode two transcription factors, YdeO and gadE, respectively. YdeO is also known to positively regulate the transcription of the gadE gene (Masuda, N. and Church, G. M., Mol. Microbiol. 2003. 48(3):699-712. Regulatory network of acid resistance genes in *Escherichia coli*.; Ma, Z., Masuda, N., and Foster, J. W., J. Bacteriol. 2004. 186(21):7378-7389. Characterization of EvgAS-YdeO-GadE branched regulatory circuit governing glutamate-dependent acid resistance in *Escherichia coli*.). However, the production of an amino acid using a microorganism with increased expression of the evgA, gadE, or ydeO genes has not been previously reported.

SUMMARY OF THE INVENTION

An aspect of the present invention is to provide a bacterial strain of the family Enterobacteriaceae which is capable of efficiently producing an L-amino acid, and to also provide a method for efficiently producing an L-amino acid using the bacterial strain.

The inventors of the present invention extensively studied in order to resolve the above-mentioned problems, resulting in the discovery that the L-amino acid-producing ability of a microorganism can be improved by modifying the microorganism to increase the expression of one or more of the evgA gene, gadE gene, or ydeO genes. These genes encode transcription factors involved in the EvgAS two-component system.

It is an aspect of the present invention to provide a method for producing an L-amino acid comprising culturing in a medium a bacterium of the family Enterobacteriaceae which has an ability to produce an L-amino acid and which has been modified to increase expression of a gene selected from the group consisting of evgA, gadE, ydeO, and combinations thereof, and collecting the L-amino acid from the medium and/or the bacterium.

It is a further aspect of the present invention to provide the method as described above, wherein the expression of said gene(s) is/are increased by a method selected from the group consisting of increasing the copy number of said gene(s), or modifying the expression regulatory sequence of said gene(s), and combinations thereof.

It is a further aspect of the present invention to provide the method as described above, wherein the expression of the evgS gene is increased.

It is a further aspect of the present invention to provide the method as described above, wherein the evgA gene is selected from the group consisting of:

(a) a DNA comprising the nucleotide sequence of SEQ ID NO: 23, (b) a DNA which hybridizes with: i) a nucleotide sequence complementary to the nucleotide sequence of SEQ ID NO: 23, or ii) a probe prepared from said nucleotide sequence in i) under stringent conditions, and which encodes a protein having transcription factor activity.

It is a further aspect of the present invention to provide the method as described above, wherein the gadE gene is selected from the group consisting of:

(a) a DNA comprising the nucleotide sequence of SEQ ID NO: 27, (b) a DNA which hybridizes with: i) a nucleotide sequence complementary to the nucleotide sequence of SEQ ID NO: 27, or ii) a probe that can be prepared from said nucleotide sequence in i) under stringent conditions, and which encodes a protein having transcription factor activity.

It is a further aspect of the present invention to provide the method as described above, wherein the ydeO gene is selected from the group consisting of:

(a) a DNA comprising the nucleotide sequence of SEQ ID NO: 29, (b) a DNA which hybridizes with: i) a nucleotide sequence complementary to the nucleotide sequence of SEQ ID NO: 29, or ii) a probe prepared from said nucleotide sequence in i) under stringent conditions, and which encodes a protein having transcription factor activity.

It is a further aspect of the present invention to provide the method as described above, wherein the evgS gene is selected from the group consisting of:

(a) a DNA comprising the nucleotide sequence of SEQ ID NO: 25.

(b) a DNA which hybridizes with: i) a nucleotide sequence complementary to the nucleotide sequence of SEQ ID NO: 25, or ii) a probe prepared from said nucleotide sequence in i) under stringent conditions, and which encodes a protein having phosphotransfer activity.

It is a further aspect of the present invention to provide the method as described above, wherein the evgA gene encodes a protein selected from the group consisting of:

(a) a protein comprising the amino acid sequence of SEQ ID NO: 24, (b) a protein comprising the amino acid sequence of SEQ ID NO: 24, but which includes one or more amino acid substitutions, deletions, insertions, additions, or inversions, and has transcription factor activity.

It is a further aspect of the present invention to provide the method as described above, wherein the gadE gene encodes a protein selected from the group consisting of:

(a) a protein comprising the amino acid sequence of SEQ ID NO: 28.

(b) a protein comprising the amino acid sequence of SEQ ID NO: 28, but which includes one or more amino acid substitutions, deletions, insertions, additions, or inversions, and has transcription factor activity.

It is a further aspect of the present invention to provide the method as described above, wherein the ydeO gene encodes a protein selected from the group consisting of:

(a) a protein comprising the amino acid sequence of SEQ ID NO: 30.

(b) a protein comprising the amino acid sequence of SEQ ID NO: 30, but which includes one or more amino acid substitutions, deletions, insertions, additions, or inversions, and has transcription factor activity.

It is a further aspect of the present invention to provide the method as described above, wherein the evgS gene encodes a protein selected from the group consisting of:

(a) a protein comprising the amino acid sequence of SEQ ID NO: 26, (b) a protein comprising the amino acid sequence of SEQ ID NO: 26, but which includes one or more amino acid substitutions, deletions, insertions, additions, or inversions, and has phosphotransferase activity.

It is a further aspect of the present invention to provide the method as described above wherein the bacterium is a member of the genera selected from the group consisting of *Escherichia, Enterobacter, Pantoea, Klebsiella*, and *Serratia*.

It is a further aspect of the present invention to provide the method as described above wherein the L-amino acid is selected from the group consisting of L-lysine, L-threonine, L-tryptophan, and combinations thereof.

BRIEF DESCRIPTION OF THE DRAWING

FIG. 1 shows construction of plasmid vector pTS1, which has a temperature-sensitive replication origin.

DESCRIPTION OF THE PREFERRED EMBODIMENTS

Hereinafter, the present invention will be explained in detail.

1. The Microorganism of the Present Invention

The microorganism of the present invention is a member of the family Enterobacteriaceae, and has an ability to produce an L-amino acid. Furthermore, this microorganism has been modified so as to increase the expression of one or more of the evgA, gadE, or ydeO genes. These genes are known to encode the transcription factor involved in the EvgAS two-component system regulon. The expression "an ability to produce an L-amino acid" means an ability to produce an L-amino acid and cause accumulation of it to a level at which it can be collected from a medium or the microorganism's cells when the microorganism is cultured in the medium. The microorganism may be able to produce multiple L-amino acids. The microorganism may inherently be able to produce an L-amino acid, or may be modified by mutagenesis or recombinant DNA techniques so that it is able to produce an L-amino acid, as described below.

Also, the phrase "increase the expression of a gene" means that the transcription and/or translation of the gene is increased.

The type of the L-amino acid is not particularly limited. Examples include basic amino acids such as L-lysine, L-ornithine, L-arginine, L-histidine, and L-citrulline; aliphatic L-amino acids such as L-isoleucine, L-alanine, L-valine, L-leucine, and glycine; L-amino acids which are hydroxymonoaminocarboxylic acids such as L-threonine and L-serine; cyclic L-amino acids such as L-proline; aromatic L-amino acids such as L-phenyl-alanine, L-tyrosine, and L-tryptophan; sulfur-containing L-amino acids such as L-cysteine, L-cystine, and L-methionine; acidic L-amino acids such as L-glutamic acid, and L-aspartic acid; and amides of acidic L-amino acid such as L-glutamine, and L-asparagine, etc. In particular, L-lysine, L-threonine, and L-tryptophan are preferred. The microorganism of the present invention may be able to produce two or more amino acids.

1-1. Imparting L-Amino Acid-Producing Ability

The following includes a description of the method for imparting the ability to produce an L-amino acid to a microorganism, along with examples of microorganisms imparted with L-amino acid-producing ability, but any microorganism can be used as long as it has an L-amino acid-producing ability.

The microorganism is not particularly limited, as long as it belongs to the family Enterobacteriaceae, such as the genera *Escherichia, Enterobacter, Pantoea, Klebsiella, Serratia, Erwinia, Salmonella, Morganella*, etc., and has an L-amino acid-producing ability. Specifically, any microorganism belonging to the family Enterobacteriaceae with its classification described in the NCBI (National Center for Biotechnology Information) database may be used. The bacterial strain, or parent strain, from the family Enterobacteriaceae which can be used to derive the microorganism of the present invention includes bacteria which belong to the genera *Escherichia, Enterobacter*, or *Pantoea*.

There is no particular *Escherichia* bacterial strain which must be used, but those listed in Neidhardt et al., may be used (Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, D.C.). One example is *Escherichia coli*. Specific examples of *Escherichia coli* are *Escherichia coli* W3110 (ATCC 27325) and *Escherichia coli* MG1655 (ATCC 47076), etc., which are prototypes derived from wild-type strains of K12.

These are available, for example, from the American Type Culture Collection (address: P.O. Box 1549, Manassas, Va. 20108, United States of America). They are available through this organization's web site via the use of accession numbers given to each bacterial strain. The accession numbers which correspond to each bacterial strain are given in the American Type Culture Collection's catalogue.

Examples of bacteria of the genus *Enterobacter* include *Enterobacter agglomerans* and *Enterobacter aerogenes*. An example of a bacterium of the genus *Pantoea* includes

*Pantoea ananatis*. In recent years, based on 16S rRNA nucleotide sequence analysis, *Enterobacter agglomerans* has on occasion been reclassified as *Pantoea agglomerans, Pantoea ananatis*, and *Pantoea stewartii*. Any bacterium belonging to the genus *Enterobacter* or *Pantoea* may be used as long as the bacterium is classified in the family Enterobacteriaceae. When *Pantoea ananatis* is bred by genetic engineering, the strains *Pantoea ananatis* AJ13355 (FERM BP-6614), AJ13356 (FERM BP-6615), AJ13601 (FERM BP-7207), or any derivative thereof may be employed. When isolated, these strains were identified and deposited as *Enterobacter agglomerans*. As stated above, analysis by 16S rRNA nucleotide sequence has resulted in their being reclassified as *Pantoea ananatis*.

The following is a description of methods for imparting L-amino acid-producing ability to microorganisms which belong to the family Enterobacteriaceae and methods for increasing the L-amino-acid-producing ability in these microorganisms.

To impart the ability to produce an L-amino acid, methods conventionally employed in the breeding of the coryneform bacteria or bacteria of the genus *Escherichia* (see "Amino Acid Fermentation", Gakkai Shuppan Center (Ltd.), 1st Edition, published May 30, 1986, pp. 77-100) can be applied. Such methods include acquisition of an auxotrophic mutant, an analog-resistant strain, or a metabolic regulation mutant. Furthermore, a recombinant strain having enhanced expression of an L-amino acid biosynthesis enzyme can be constructed. When breeding the L-amino acid-producing bacteria, one or more properties, such as an auxotrophic or metabolic regulation mutation, and analog resistance may be imparted. The expression of one or more L-amino acid biosynthesis enzymes can be enhanced singly or in combinations of two or more. Furthermore, the technique of imparting these properties may be combined with the technique of enhancing the biosynthesis enzymes.

An auxotrophic mutant strain, L-amino acid analog-resistant strain, or metabolic regulation mutant strain with the ability to produce an L-amino acid can be obtained by subjecting a parent strain or wild-type strain to a conventional mutation treatment, such as exposure to X-rays or UV irradiation, or treatment with a mutagenic agent such as N-methyl-N'-nitro-N-nitrosoguanidine (NTG) or ethyl methane sulfonate (EMS), etc., then selecting those which exhibit the desired properties and which also have the ability to produce an L-amino acid.

The following are examples of L-lysine-producing bacteria and method for construction.

For example, bacteria which have L-lysine-producing ability include an L-lysine analog-resistant strain or a metabolic regulation mutant strain. Examples of the L-lysine analogs include, but are not limited to, oxalysine, lysine hydroxamate, S-(2-aminoethyl)-cysteine (AEC), γ-methyl lysine, α-chlorocaprolactam, etc. Mutant strains which are resistant to these lysine analogs may be obtained by subjecting bacteria belonging to the genus *Escherichia* to a conventional artificial mutagenesis treatment. Examples of L-lysine-producing bacteria include *Escherichia coli* AJ11442 (FERM BP-1543, NRRL B-12185; see JP56-18596A and U.S. Pat. No. 4,346,170), *Escherichia coli* VL611 (EP1016710), etc. The *Escherichia coli* WC1-96 strain (see WO96/17930) may also be used as an L-lysine producing bacterium. The WC1-96 strain was bred by imparting AEC resistance to the W3110 strain derived from *Escherichia coli* K-12. This strain was named *Escherichia coli* AJ13069, and was deposited on Dec. 6, 1994 at the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14690. Then, it was converted to an international deposit under the Budapest Treaty on Sep. 29, 1995, and given Accession No. FERM BP-5252.

L-lysine-producing bacteria can also be constructed by increasing the activity of an L-lysine biosynthetic enzyme. The activity of these enzymes can be increased by increasing the copy number of the gene encoding the desired enzyme in the cells, or by modifying an expression regulatory sequence of the gene.

Examples of genes encoding L-lysine biosynthesis enzymes include, but are not limited to, genes encoding dihydrodipicolinate synthase (dapA), aspartokinase (lysC), dihydrodipicolinate reductase (dapB), diaminopimelate decarbonylase (lysA), diaminopimelate dehydrogenase (ddh) (WO96/40934, U.S. Pat. No. 6,040,160), phosphoenolpyruvate carboxylase (ppc) (60-87788A), aspartate aminotransferase (aspC) (JP6-102028)B, diaminopimelate epimerase (dapF) (JP2003-135066A), aspartate semialdehyde dehydrogenase (asd) (WO00/61723), and other genes encoding enzymes of the diaminopimelate pathway, as well as a gene encoding homoaconitate hydratase (JP2000-157276A) and other genes encoding enzymes of the aminoadipate pathway.

Furthermore, wild-type dihydrodipicolinate synthase (DDPS) and aspartokinase (AK) are known to be suppressed by feedback inhibition by L-lysine; therefore, when dapA and lysC are used, it is preferable to use mutant genes encoding dihydrodipicolinate synthase and aspartokinase, respectively, that are resistant to the feedback inhibition by L-lysine (EP 0733710, U.S. Pat. No. 5,932,453).

Examples of the DNA encoding mutant dihydrodipicolinate synthase that is resistant to feedback inhibition by L-lysine include a DNA encoding DDPS having an amino acid sequence wherein the 118th histidine residue is substituted with tyrosine. (U.S. Pat. Nos. 5,661,012 and 6,040,160). Furthermore, examples of the DNA encoding a mutant AK that is resistant to feedback inhibition by L-lysine include a DNA encoding AK having the amino acid sequence wherein the 352-threonine residue is substituted with isoleucine (U.S. Pat. Nos. 5,661,012 and 6,040,160). These mutant DNAs can be obtained by site-directed mutagenesis using PCR, or the like.

The following is an example of a technique for imparting an L-lysine-producing ability by introducing a gene encoding an L-lysine biosynthesis enzyme into a host. That is, recombinant DNA is prepared by ligating a gene fragment that encodes the L-lysine biosynthesis gene with a vector that functions in the chosen host microorganism, preferably a multi copy vector, and transforming the host with the recombinant vector. Due to the transformation, the copy number of the gene encoding the L-lysine biosynthesis enzyme in the host cell increases, increasing the expression and consequently increasing the enzymatic activity.

The genes encoding the L-lysine biosynthesis enzymes are not particularly specified, as long as they can be expressed in the host microorganism. Examples include genes derived from *Escherichia coli*, and genes derived from the coryneform group of bacteria. Because the entire genome sequences of *Escherichia coli* and *Corynebacterium glutamicum* have been reported, it is possible to synthesize primers based on the nucleotide sequences of these genes and obtain these genes by PCR in which the genomic DNA of a microorganism, such as *Escherichia coli* K12, etc., is used as the template.

In order to clone the genes, plasmids that autonomously replicate in the family Enterobacteriaceae can be used. Examples include pBR322, pTWV228 (Takara Bio Inc.), pMW119 (Nippon Gene Co., Ltd.), pUC19, pSTV29 (Takara Bio Inc.), RSF1010 (Gene, 75:271-288 (1989)), etc. In addition to these, a phage vector may also be used.

To ligate the target gene to the above-mentioned vector, the vector is digested with a restriction enzyme matched to the end of the DNA fragment containing the target gene. The ligation is usually conducted with a ligase such as T4 DNA ligase. Target genes may be located on separate vectors, respectively, or located on the same vector. Typical methods known to those skilled in the art can be employed for digesting and ligating a DNA, as well as for preparing genomic DNA, performing PCR, preparing plasmid DNA, transformation, designing oligonucleotide primers, etc. These methods are described in Sambrook, J., and Russell, D. W. Molecular Cloning A Laboratory Manual/Third Edition. New York: Cold Spring Harbor Laboratory Press (2001), etc. Any method which achieves adequate transformation efficiency may be employed to introduce the recombinant DNA that has been prepared as described above into the host microorganism. An example of such a method is electroporation (Can. J. Microbiol. 43:197-201 (1997)). An example of a plasmid prepared using this method is the Lys-producing plasmid pCABD2 which contains the dapA, dapB, and LysC genes (WO 01/53459).

Enhancing the expression of genes encoding L-lysine biosynthesis enzymes can also be achieved by introducing multiple copies of the target gene into the genomic DNA of a microorganism. Multiple copies of the target gene can be introduced into the genomic DNA of the microorganism by using a sequence which is present in multiple copies on the genomic DNA as a target in homologous recombination. Such site-specific introduction of mutations based on gene substitution using homologous recombination has been described. Either a linear DNA or a plasmid containing a temperature-sensitive replication origin can be used in such methods (U.S. Pat. No. 6,303,383 and JP05-007491A). Repetitive DNA and inverted repeats present on the ends of transposable elements can be employed as sequences which are present in multiple copies on genomic DNA. An L-lysine biosynthesis gene may be ligated in tandem with a gene which is native to the genome, or it may be introduced into a non-essential region on the genome or a gene region in which the L-lysine yield will be improved by deletion. Or, as disclosed in U.S. Pat. No. 5,595,889, the target gene may also be located on a transposon, which is then transferred to introduce multiple copies to the genomic DNA. With either method, the number of copies of the target gene in the transformant increases, so that the enzymatic activity of L-lysine biosynthesis increases.

In addition to the above-described genetic amplification, an increase in the L-lysine biosynthesis enzyme activity can be achieved by replacing an expression regulatory sequence of the target gene, such as a promoter, etc., with a stronger one (see JP1-215280A). For example, the lac promoter, trp promoter, trc promoter, tac promoter, araBA promoter, lambda phage PR promoter, PL promoter, tet promoter, T7 promoter, φ10 promoter, etc., are known as strong promoters. Substitution of the native promoter with these promoters enhances expression of the target gene, thus increasing the enzymatic activity. Examples of strong promoters and methods for evaluating strength of promoters are described in Goldstein et al. (Biotechnol. Annu. Rev., 1, 105-128, (1995) Prokaryotic promoters in biotechnology.), etc.

An increase in the activity of the target enzyme can also be achieved by modifying an element which is involved in the regulation of expression of the gene that encodes the target enzyme, for example, an operator or repressor (Hamilton et al, J. Bacteriol. 171:4617-4622 (1989)). As disclosed in WO 00/18935, it is possible to substitute several bases in the promoter region of a target gene to modify and strengthen it. Furthermore, substituting several nucleotides in the spacer between the ribosome binding site (RBS) and the start codon, particularly in the sequence immediately upstream of the start codon, is known to have a strong effect on mRNA translation efficiency. Therefore, these regions may be modified to increase transcription efficiency. The expression regulatory regions of the target gene, such as a promoter, etc., can be determined by promoter probe vectors and gene analysis software such as GENETYX (GENETYX CORPORATION), etc. Expression of the target gene can be increased by substituting or modifying these promoters. Substitution of expression regulatory sequences can be conducted, for example, in the same manner as in the above-described gene substitution employing temperature-sensitive plasmids. The Red-driven integration method (WO2005/010175) may also be used.

Furthermore, in the L-amino-acid-producing bacteria, when the activity of an enzyme catalyzes a reaction to produce a compound other than the target L-amino acid, directs a reaction which branches off from the biosynthesis pathway of the target L-amino acid, or the activity of an enzyme has a negative effect on the synthesis or accumulation of the target L-amino acid, such activities may be reduced or deleted. In L-lysine production, such enzymes include homoserine dehydrogenase (thrA), lysine decarboxylase (cadA, ldcC), and malic enzyme (sfcA, b2463). Strains with reduced or deficient enzymatic activity are disclosed in WO 95/23864, WO96/17930, WO2005/010175, etc.

To reduce or delete the activities of these enzymes, a mutant which reduces or deletes the enzyme activity may be introduced into the gene of the above-mentioned enzyme on the genome, using a known mutatagenisis method or genetic recombination techniques. A mutant can be introduced, for example, by deleting the gene that encodes an enzyme on the genome by genetic recombination, or by modifying an expression regulatory sequence such as a promoter or a Shine-Dalgarno (SD) sequence, etc. This can also be achieved by introducing an amino acid substitution (missense mutation) or stop codon (nonsense mutation) in the region encoding the enzyme on the genome, by introducing a frameshift mutation to add or delete 1-2 bases, or by deleting a part of the gene or the entire region (J. Biol. Chem. 272:8611-8617 (1997)). Also, the enzyme activity can be reduced or deleted by deleting a part or the entire coding region of the gene that encodes the mutant enzyme, and then substituting the normal gene on the genome with the mutant gene by homologous recombination, etc., or introducing a transposon or IS element into said gene. The following methods may be used to introduce a mutation which reduces or deletes the above-mentioned enzyme activity by genetic recombination. An isolated DNA containing the target gene is mutated so that the resulting mutant gene does not produce an enzyme that functions normally. Then, a microorganism which belongs to the family Enterobacteriaceae is transformed with the DNA containing the mutated gene to cause recombination between the mutated gene and the target gene on the genome. Thus, the target gene on the genome may be substituted with the mutated gene. For gene substitution using this kind of homologous recombination, linear DNA can be used, such as in the method called "Red-driven integration" (Datsenko, K. A, and Wanner, B. L. Proc. Natl. Acad. Sci. USA. 97:6640-6645 (2000)), a method combining the Red-driven integration method and the λ phage excision system (Cho, E. H., Gumport, R. I., Gardner, J. F. J. Bacteriol. 184: 5200-5203 (2002)) (see WO2005/010175), etc. A temperature-sensitive replication origin could also be employed (U.S. Pat. No. 6,303,383; U.S. Pat. No. 5,616,480). Such site-specific introduction of mutations by gene substitution using homologous recombination as described above may also be performed using a plasmid which is not able to replicate in the chosen host.

The above-mentioned method for increasing the activity of the enzyme involving L-lysine biosynthesis and the method for lowering the enzyme activity may likewise be used in breeding other L-amino acid-producing bacteria. The following is a description of methods for breeding other L-amino acid bacteria.

The L-tryptophan-producing bacteria preferably used in the present invention include bacteria in which the activity of one or more of the following enzymes anthranilate synthase, phosphoglycerate dehydrogenase, or tryptophan synthase has been enhanced. Since anthranilate synthase and phosphoglycerate dehydrogenase both are subject to feedback inhibition by L-tryptophan and L-serine, the activities of these enzymes can be increased by retaining the desensitizing mutant enzyme. For instance, it is possible to obtain a bacterium which has a desensitizing enzyme by causing a mutation of the anthranilate synthase gene (trpE) and/or the phosphoglycerate dehydrogenase gene (serA) to prevent the feedback inhibition, then introducing the mutant gene into a microorganism belonging to the family Enterobacteriaceae. (U.S. Pat. No. 5,618,716, U.S. Pat. No. 6,180,373) A specific example of this kind of bacteria includes a transformant obtained by introducing plasmid pGH5 having a mutant serA that encodes desensitized phosphoglycerate dehydrogenase into *Escherichia coli* SV164 which retains desensitized anthranilate synthase (WO94/08301). Strain SV164 is obtained by introducing a gene that encodes desensitized anthranilate synthase into a trpE deficient strain of *Escherichia coli* KB862 (DSM7196) (See WO94/08031).

Bacteria transformed with recombinant DNA containing a tryptophan operon are also preferable. A specific example includes *Escherichia coli* transformed with a tryptophan operon containing a gene encoding desensitized anthranilate synthase (JP57-71397A, JP62-244382A, U.S. Pat. No. 4,371,614). Furthermore, it is possible to enhance or impart an ability to produce L-tryptophan by enhancing the expression of a gene encoding tryptophan synthase (trpBA). Tryptophan synthase consists of α and β subunits that are encoded by trpA and trpB, respectively. The nucleotide sequence of trpA is shown in SEQ ID NO: 13 and the nucleotide sequence of trpB is shown in SEQ ID NO: 15.

A strain with deficient trpR, the tryptophan operon repressor, and a strain with a mutant trpR are also preferable. (U.S. Pat. No. 4,371,614, WO2005/056776).

Another preferable L-tryptophan-producing bacterium is one in which malate synthase, isocitrate lyase, isocitrate dehydrogenase/phosphatase operon (ace operon) is structurally expressed or the expression of said operon has been enhanced. Specifically, it is preferable that the promoter of the ace operon is not suppressed by the repressor iclR or that the suppression by iclR has been removed. Such a bacterium can be obtained by disrupting the iclR gene or modifying the expression regulatory sequence of the ace operon. The iclR gene of *Escherichia coli* is shown in SEQ ID NO: 5. A bacterium with enhanced expression of the ace operon can be obtained by ligating a DNA containing the ace operon to a strong promoter and introducing the recombinant DNA into cells using a plasmid or by homologous recombination, or amplifying the copy number of the ace operon using a transposon. Genes contained in the ace operon include aceB, aceA, and aceK. The nucleotide sequences of aceB, aceA and aceK are shown in SEQ ID NOS: 9, 7, and 11, respectively.

Examples of L-tryptophan-producing bacteria include *Escherichia coli* AGX17 (pGX44) [NRRL B-12263], which is L-phenylalanine and L-tyrosine auxotrophic, and AGX6 (pGX50) aroP [NRRL B-12264], which contains the tryptophan operon-containing plasmid pGX50 (see U.S. Pat. No. 4,371,614, for both). These strains are available from the Agricultural Research Service Culture Collection, National Center for Agricultural Utilization Research (address: Peoria, Ill. 61604, USA).

L-tryptophan, L-phenylalanine, and L-tyrosine are all aromatic amino acids and share a common biosynthesis pathway. Examples of the genes encoding the biosynthesis enzymes for these aromatic amino acids include deoxyarabino-heptulosonate phosphate synthase (aroG), 3-dehydroquinate synthase (aroB), shikimate dehydratase, shikimate kinase (aroL), 5-enolpyruvylshikimate-3-phosphate synthase (aroA), and chorismate synthase (aroC) (EP763127). Therefore, by placing multiple copies of the genes encoding these enzymes on a plasmid or genome, the aromatic amino acid-producing ability can be improved. It is known that these genes are controlled by a tyrosine repressor (tyrR), so the enzyme activity of an aromatic amino acid biosynthesis may also be increased by deleting the tyrR gene (See EP763127).

Examples of L-phenylalanine-producing bacteria include *Escherichia coli*

AJ12739 (tyrA::Tn10, tyrR) (VKPM B-8197) which is tyrA, tyrR deficient, and strains with amplified genes encoding a phenylalanine excreting protein such as yddG and yedA (WO03/044192; US2003/0148473A1).

L-threonine-producing bacteria used in the present patent are preferably microorganisms belonging to the family Enterobacteriaceae wherein an L-threonine biosynthesis enzyme has been enhanced. Examples of such genes include genes encoding aspartokinase III (lysC), aspartate-semialdehyde dehydrogenase (asd), aspartokinase I (thrA included in thr operon), homoserine kinase (thrB), and threonine synthase (thrC). Two or more of these genes may be introduced. The L-threonine biosynthesis gene may be introduced into a bacterium of the genus *Escherichia* with suppressed threonine degradation. Examples such bacteria include the TDH6 strain wherein the threonine dehydrogenase activity has been deleted (U.S. Pat. No. 6,960,455), and so forth.

Activities of some of the enzymes of the L-threonine biosynthesis pathway are suppressed by L-threonine. Therefore, in order to construct an L-threonine-producing bacterium, it is preferable to modify the L-threonine biosynthesis enzyme so that the enzyme is not subject to feedback inhibition by L-threonine. The above-mentioned thrA, thrB, and thrC genes constitute the threonine operon which contains an attenuator structure. Their expression is suppressed by this attenuation. In addition, the expression of the threonine operon is inhibited by isoleucine and threonine present during the culture. The modification of the threonine operon can be achieved by removing the leader sequence in the attenuation region or the attenuator. (See Lynn, S. P., Burton, W. S., Donohue, T. J., Gould, R. M., Gumport, R. I., and Gardner, J. F. J. Mol. Biol. 194:59-69 (1987); WO02/26993; WO2005/049808).

A native promoter is present upstream of the threonine operon. The promoter may be substituted with a non-native promoter (see WO 98/04715). Alternatively, a threonine operon may be constructed so that the expression of the gene involved in threonine biosynthesis is controlled by the lambda phage repressor and promoter (See EP0593792). Also, to prevent feedback inhibition by L-threonine, an α-amino-β-hydroxyvaleric acid (AHV) resistant strain of *Escherichia* bacteria may be selected.

The copy number of the modified threonine operon as described above may be increased in the host, or may be ligated to a strong promoter to further enhance the expression of the operon. In addition to amplifying the copy number using a plasmid, the copy number can be increased by introducing the threonine operon on the genome using a transposon, Mu-phage, etc.

The gene encoding aspartokinase III gene (lysC) can be modified to prevent feedback inhibition by L-lysine. This modified lysC gene can be obtained using the method described in the U.S. Pat. No. 5,932,453.

Aside from the L-threonine biosynthesis enzymes, expression of genes related to the glycolytic system, TCA cycle, and respiratory chain can also be enhanced. Furthermore, the expression of any gene which controls expression of these genes, and/or a gene which induces the uptake of sugar can also be enhanced. Examples of genes which are effective in L-threonine production include genes encoding transhydrogenase (pntAB) (EP733712), phosphoenolpyruvate carboxylase (ppc) (WO95/06114), phosphoenolpyruvate synthase gene (pps) (EP877090), and a gene encoding pyruvate carboxylase of a coryneform bacterium or a bacterium of the genus *Bacillus* (WO99/18228, EP1092776).

The expression of genes that impart resistance to L-threonine, L-homoserine, and/or both in the host can also be enhanced. Examples of such genes include rhtA (Res. Microbiol. 154:123-135 (2003)), rhtB (EP0994190), rhtC (EP1013765), yfiK, and yeaS (EP1016710). For methods of imparting L-threonine resistance to a host, refer to EP0994190, WO90/04636.

Another example of an L-threonine-producing bacterium is *Escherichia coli* VKPM B-3996 (see U.S. Pat. No. 5,175,107). This VKPM B-3996 strain was deposited on Apr. 7, 1987, under Accession No. VKPM B-3996, at the Russian National Collection of Industrial Microorganisms (VKPM), GNII Genetika (address: Russia, 117545 Moscow, 1 Dorozhny proezd. 1). In addition, the VKPM B-3996 strain contains the plasmid pVIC40 (WO90/04636), which was obtained by inserting a threonine biosynthesis gene (threonine operon: thrABC) into a wide host-range vector plasmid pAY32 which includes a streptomycin-resistant marker (see Chistorerdov, A. Y., and Tsygankov, Y. D. Plasmid, 16, 161-167 (1986)). The thrA gene on pVIC40, and the feedback inhibition by the L-threonine of aspartokinase I-homoserine dehydrogenase I has been desensitized.

Another example of an L-threonine-producing bacteria is *Escherichia coli* VKPM B-5318 (see EP0593792). The VKPM B-5318 strain was deposited under Accession No. VKPM B-5318 at the Russian National Collection of Industrial Microorganisms (VKPM), GNII Genetika (address: Russia, 117545 Moscow, 1 Dorozhny proezd. 1) on May 3, 1990. This VKPM B-5318 strain is non-auxotrophic for isoleucine, and contains a recombinant plasmid constructed so that the gene involved in threonine biosynthesis, i.e., the threonine operon wherein the attenuator and inherent transcriptional regulatory regions have been deleted, is located downstream of the temperature-sensitive CI repressor, PR promoter, and the N-terminus of the Cro protein of the lambda phage. Therefore, expression of the gene involved in the threonine biosynthesis is controlled by the lambda phage repressor and promoter.

Examples of L-glutamic acid-producing bacteria include a microorganism belonging to the family Enterobacteriaceae which has been modified to increase the expression of the gene encoding an enzyme that is involved in L-glutamic acid biosynthesis. The enzymes involved in the L-glutamic acid biosynthesis include glutamate dehydrogenase (hereinafter, also referred to as "GDH"), glutamine synthetase, glutamate synthase, isocitrate dehydrogenase, aconitate hydratase, citrate synthase (hereinafter, also referred to as "CS"), phosphoenolpyruvate carboxylase (hereinafter, also referred to as "PEPC"), pyruvate carboxylase, pyruvate dehydrogenase, pyruvate kinase, phosphoenolpyruvate synthase, enolase, phosphoglycerolmutase, phosphoglycerate kinase, glyceraldehyde-3-phosphate dehydrogenase, triose phosphate isomerase, fructose-bisphosphate aldolase, phosphofructokinase, glucosephosphate isomerase, etc. Of these enzymes, one or more of CS, PEPC, and GDH is preferable, and all three are more preferable.

Examples of microorganisms belonging to the family Enterobacteriaceae which have been modified to enhance the expression of the citrate synthase gene, phosphoenolpyruvate carboxylase gene, and/or glutamate dehydrogenase gene using the methods described above are disclosed in U.S. Pat. Nos. 6,197,559 & 6,331,419, EP0999282.

Furthermore, microorganisms belonging to the family Enterobacteriaceae which have been modified to increase the activity of either or both of 6-phosphogluconate dehydratase or 2-keto-3-deoxy-6-phosphogluconate aldolase may also be used (EP1352966).

For production of L-glutamic acid, Enterobacteriaceae may be used in which the activity of an enzyme that catalyzes a reaction to produce a compound other than L-glutamic acid, or which directs a reaction to branch off from the biosynthesis pathway of L-glutamic acid, has been deleted or reduced. Examples of such enzymes include 2-oxoglutarate dehydrogenase, isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase, etc. Of these, it is especially preferable to reduce or delete the activity of 2-oxoglutarate dehydrogenase.

Methods for deleting or reducing the activity of 2-oxoglutarate dehydrogenase in a microorganism belonging to the family Enterobacteriaceae are described in U.S. Pat. No. 5,573,945, U.S. Pat. No. 6,197,559, and U.S. Pat. No. 6,331,419. Specifically, examples of microorganisms belonging to the family Enterobacteriaceae wherein the activity of 2-oxoglutarate dehydrogenase has been deleted or reduced include the following:

*Pantoea ananatis* AJ13601 (FERM BP-7207)
*Klebsiella planticola* AJ13410 strain (FERM BP-6617)
*Escherichia coli* AJ12949 (FERM BP-4881)

Examples of an L-histidine-producing bacterium include *Escherichia coli* FERM P-5038 and FERM P-5048. These strains contain a vector which contains genetic information involved in L-histidine biosynthesis (JP56-005099A). Other examples includes bacteria which have been transformed with the amino acid export gene Rht (EP1016710), and

*Escherichia coli* 80 which is resistant to sulfaguanidine, D,L-1,2,4-triazole-3-alanine, and streptomycin (VKPM B-7270, Russian Patent Publication No. 2119536), etc.

Microorganisms with enhanced expression of gene(s) encoding L-histidine biosynthesis pathway enzyme(s) may be used. Examples of such genes includes the genes encoding ATP phosphoribosyltransferase (hisG), phosphoribosyl AMP cyclohydrolase gene (hisI), phosphoribosyl-ATP pyrophosphohydrolase (hisIE), phosphoribosylformimino-5-aminoimidazole carboxamide ribotide isomerase (hisA), amidotransferase gene (hisH), histidinol phosphate aminotransferase (hisC), histidinol phosphatase (hisB), and histidinol dehydrogenase gene (hisD), etc.

The L-cysteine-producing bacteria include bacteria with reduced activity of cystathionine β-lyase (JP2003-169668A), and *Escherichia* bacteria that retain serine acetyltransferase, but with reduced or eliminated feedback inhibition by L-cysteine (JP11-155571A).

The L-proline-producing bacteria include *Escherichia coli* 702 (VKPMB-8011) which is resistant to 3,4-dehydroxyproline and azetidine-2-carboxylate, and the 702 ilvA strain (VKPMB-8012 strain) which is deficient in ilvA, and is derived from the strain 702 (JP2002-300874A).

Examples of L-arginine-producing bacteria include *Escherichia coli* mutant strains which are resistant to α-methylmethionine, p-fluorophenylalanine, D-arginine, arginine hydroxamic acid, S-(2-aminoethyl)-cysteine, α-methylserine, β-2-thienylalanine, or sulfaguanidine (see JP56-106598A), etc. The *Escherichia coli* 237 strain is an L-arginine-producing bacterium that has a mutant which is resistant to feedback inhibition by L-arginine and retains highly active N-acetyl glutamate synthase (Russian Patent Application No. 2000117677). This strain, numbered VKPM B-7925, was deposited with the Russian National Collection of Industrial Microorganisms (VKPM), GNII Genetika on Apr. 10, 2000, and converted to an international deposit under the Budapest Treaty on May 18, 2001. The *Escherichia coli* 382 strain, which is a derivative of the 237 strain and is an L-arginine-producing bacterium with improved acetic acid assimilating ability, may also be used (JP2002-017342A). The *Escherichia coli* 382 strain, numbered VKPM B-7926, was deposited with the Russian National Collection of Industrial Microorganisms (VKPM) on Apr. 10, 2000.

Also, for producing L-arginine, microorganisms with increased expression of gene(s) encoding enzyme(s) involved in L-arginine biosynthesis may be used. Examples of L-arginine biosynthesis enzymes are N-acetyl glutamate synthase (argA), N-acetyl-glutamyl-phosphate reductase (argC), ornithine acetyltransferase (argJ), N-acetyl glutamate kinase (argB), acetyl ornithine transaminase (argD), acetyl ornithine deacetylase (argE), ornithine carbamoyl transferase (argF), argininosuccinate synthase (argG), argininosuccinate lyase (argH), and carbamoyl phosphate synthase (carAB). After each enzyme name, the name of the gene encoding it is given in parentheses. A mutation of the N-acetyl glutamate synthase gene (argA) to remove L-arginine feedback inhibition by substitution of the amino acid sequence corresponding to positions 15 to 19 in the wild-type may be used (EP1170361).

The L-leucine-producing bacteria include *Escherichia coli* with an inactive ilvE gene, which encodes the branched-chain amino-acid transaminase, and enhanced activity of the aromatic amino acid transaminase encoded by the tyrB gene (EP1375655A), *Escherichia coli* H-9068 (ATCC21530) which is resistant to 4-azaleucine or 5,5,5-trifluoroleucine, *Escherichia coli* H-9070 (FERM BP-4704), *Escherichia coli* H-9072 (FERM BP-4706) (U.S. Pat. No. 5,744,331), *Escherichia coli* with desensitized isopropylmalate synthase feedback inhibition by L-leucine (EP1067191), *Escherichia coli* AJ11478 which is resistant to β-2 thienylalanine and β-hydroxyleucine (U.S. Pat. No. 5,763,231), and so on.

L-isoleucine-producing bacteria include a 6-dimethyl aminopurine-resistant *Escherichia coli* mutant strain (JP5-304969A), L-isoleucine hydroxamate-resistant *Escherichia coli* mutant strain (JP5-130882A), thiaisoleucine-resistant *Escherichia coli* mutant strain (JP5-130882A), DL-ethionine-resistant *Escherichia coli* mutant strain (JP5-130882A), and arginine hydroxamate-resistant mutant strain (JP5-130882A). Examples of the recombinant *Escherichia* bacteria are those in which the genes encoding the L-isoleucine biosynthesis enzymes threonine deaminase or acetohydroxy acid synthase have been strengthened by transformation with a plasmid (JP2-458A, JP2-42988A, JP8-47397), etc.

L-valine-producing bacteria include *Escherichia coli* VL1970 (U.S. Pat. No. 5,658,766), etc. Examples of L-valine-producing bacteria further include a mutant which requires lipoic acid for its growth and/or lacks $H^+$-ATPase (WO96/06926), and an *Escherichia* bacterium transformed with a DNA fragment containing the ilvGMEDA operon which expresses at least the ilvG, ilvM, ilvE, and ilvD genes. Since the expression of the ilvGMEDA operon is regulated (attenuated) by L-valine and/or L-isoleucine and/or L-leucine, the region required for attenuation should be removed or mutated in order to remove the suppression of the expression by L-valine (U.S. Pat. No. 5,998,178). The ilvGMEDA operon should not express the ilvA gene, which encodes threonine deaminase. *Escherichia coli* VL1970, in which the ileS17 mutation is present which removes the attenuation as described above, was deposited as Accession No. VKPM B-4411 at GNIIgenetika (Russian National Collection of Industrial Microorganisms (VKPM) Depositary, GNIIgenetika) (address: 1, Dorozhny Proezd., 1, 113545, Moscow, Russia).

Aside from a gene which encodes an inherent biosynthesis enzyme, a gene which is involved in sugar uptake, sugar metabolism (glycolytic system), and energy metabolism may be enhanced in the L-amino acid-producing bacteria used in the present invention.

Examples of the genes involved in sugar metabolism are genes which encode glycolytic enzymes or proteins which uptake sugar, such as genes encoding glucose-6-phosphate isomerase (pgi; WO01/02542), phosphoenolpyruvate synthase (pps; EP877090), phosphoglucomutase (pgm; WO03/04598), fructose-bisphosphate aldolase (fba; WO03/04664), pyruvate kinase (pykF; WO03/008609), transaldolase (talB; WO03/008611), fumarase (fum; WO01/02545), phosphoenolpyruvate synthase (pps; EP877090), the non-PTS sucrose uptake systems (csc; EP149911), and sucrose-assimilating genes (scrAB operon; WO90/04636).

Examples of the genes involved in energy metabolism include the transhydrogenase gene (pntAB; U.S. Pat. No. 5,830,716) and the cytochromoe bo type oxidase gene (cyoABCD; EP1070376).

A microorganism which has the ability to produce an L-amino acid may be modified, as described above, so as to increase the expression of one or more of the following genes: evgA, gadE, or ydeO, which are the genes encoding the transcription factor involved in the EvgAS two-component system. The ability to produce the target substance may be imparted after the modification to increase the expression of the evgA gene, gadE gene, or ydeO gene. Expression of the evgA gene, gadE gene, or ydeO gene may be increased by increasing the expression of the endogenous evgA gene, gadE gene, or ydeO gene through modification of the expression regulatory region, including promoter modification, as described later, or increasing the copy number of the evgA gene, gadE gene, or ydeO gene through introduction of a plasmid containing the evgA gene, gadE gene, or ydeO gene, or amplification of these genes on the chromosome of the bacterium, and so forth. Furthermore, a combination of these techniques may be employed.

The "EvgAS two-component system" means a pathway which activates transcription factors via EvgA-EvgA histidine-aspartate phosphorelation regulation. More specifically, the EvgS protein (SEQ ID NO: 26), which is a sensor kinase, autophosphorylates the histidine residue of this protein, and then transfers the phosphate group to aspartate residues specific to the EvgA protein (SEQ ID NO: 24), which is a response regulator and transcription factor. EvgA is activated by this phosphorylation and, as a result, regulates the transcription of many genes, as well as activating the transcription of the ydeO gene (SEQ ID NO: 29) that encodes the transcription factor YdeO protein (SEQ ID NO: 30) and/or the gadE gene (SEQ ID NO: 27) that encodes the transcription factor GadE protein (SEQ ID NO: 28) (J. Bacteriol. 184:6225-6234, 2002; Mol. Microbiol. 48:699-712, 2003). The YdeO protein also activates the transcription of the gadE gene. As a result of the EvgA and YdeO-activated transcription of the gadE gene, the expression of the GadE protein increases, and since it is a positive transcription factor, it amplifies the transcription of other genes (Microbiology. 150:61-72, 2004; J Bacteriol. 186:7378-89, 2004). Therefore, "the transcription factor involved in the EvgAS two-component regulator" as used herein refers to the EvgA protein, GadE protein, or YdeO protein.

The "sensor kinase" is a protein which senses an environmental factor, such as a ligand, phosphorylates its own histidine residues using ATP, and then delivers this phosphate group to a response regulator. The "response regulator" is a protein which conveys the information within cells after being activated by phosphorylating the specific aspartate from the sensor kinase. In many cases, it is a transcription factor.

The improvement in the expression of the gene encoding the EvgA protein, GadE protein, or YdeO protein (hereafter, the evgA, gadE, or ydeO genes) when comparing it to the parent strain, for example, a wild-type strain or non-modified strain, can be confirmed by comparing the amount of mRNA with that in the wild-type or non-modified strain. Northern hybridization and Reverse-Transcriptase PCR (RT-PCR) can be used to confirm the amount of expression. (Sambrook, J., and Russell, D. W. Molecular Cloning A Laboratory Manual/Third Edition. New York: Cold Spring Harbor Laboratory Press (2001)). The degree of the increase in enzymatic activity is not limited as long as the activity is increased as compared to that in the wild-type or non-modified strain, but it is advantageous, for example, for it to be 1.5 or more times, preferably 2 or more times, or more preferably 3 or more times that of the wild-type or non-modified strain. An increase in the enzymatic activity can be confirmed if the target protein amount is increased relative to that of the non-modified or wild-type strain. This can be detected, for instance, by Western blot using an antibody. (Sambrook, J., and Russell, D. W. Molecular Cloning A Laboratory Manual/Third Edition. New York: Cold Spring Harbor Laboratory Press (2001)).

The "transcription factor" indicates a transcription factor of a gene in which the expression is controlled by the EvgSA two-component regulator, and corresponds to the EvgA protein, GadE protein, and YdeO protein. These proteins positively regulate the transcription of the gene encoding various metabolic enzymes which are under the control of the EvgSA two-component regulator. For example, the transcription of the gnd gene that encodes 6-phosphogluconate dehydrogenase (GND) or the purA gene that encodes adenylosuccinate synthase is activated by the transcription factor of the EvgSA two-component regulator. That is, by improving the amount of the EvgA, GadE, or YdeO proteins that is produced compared to the wild-type strain or non-modified strain, the transcription amount of the EvgAS two-component regulator-controlled gene increases. The activity of the transcription factor can be measured using the electrophoretic mobility shift assay, which measures the ligation with DNA, or the transcription activity can be measured in vitro (Sambrook, J., and Russell, D. W. Molecular Cloning A Laboratory Manual/Third Edition. New York: Cold Spring Harbor Laboratory Press (2001)).

The evgA gene can be isolated or derived from (native to) an *Escherichia* bacterium and its homologs. For example, the evgA gene of *Escherichia coli* (SEQ ID NO: 23) encodes a protein having the amino acid sequence of SEQ ID NO: 24. (GenBank Accession No. NP_416870 [gi:16130301]).

Homologs of the evgA gene are derived from other microorganisms which have a high similarity in structure to the *Escherichia* evgA gene, improve the ability to produce an L-amino acid, and exhibit transcription factor activity when introduced into the host. Examples of evgA homologs are the evgA genes isolated or derived from (native to) the genera *Salmonella, Shigella*, and *Yersinia*, etc. These genes are registered at GenBank. Furthermore, based on the homology with the genes given in the above examples, evgA genes may be cloned from coryneform bacteria, such as *Corynebacterium glutamicum, Brevibacterium lactofermentum*, etc.; the bacteria of the genus *Pseudomonas*, such as *Pseudomonas aeruginosa*, etc.; bacteria of the genus *Mycobacterium*, such as *Mycobacterium tuberculosis*, etc.; and bacteria of the genus *Bacillus*. Genes having different names are acceptable as long as they are highly homologous with the *Escherichia* evgA gene. For example, evgA gene homologs include a gene cloned from the synthetic oligonucleotides of SEQ ID NOS: 17 and 18.

The nucleotide sequences of the evgA gene homologs can be obtained by searching for a gene with high homology from a known database, based on the above-mentioned sequence information. The homology of the amino acid sequences and nucleotide sequences can be determined using, for instance, Karlin and Altschul's BLAST algorithm (Pro. Natl. Acad. Sci. USA, 90, 5873 (1993)) or FASTA (Methods Enzymol., 183, 63 (1990)). Based on this BLAST algorithm, programs called BLASTN or BLASTX have been developed (see http://www.ncbi.nih.gov/BLAST/).

The gadE gene can be isolated or derived from (native to) *Escherichia* bacteria and its homologs. An example of gadE gene of *Escherichia coli* includes the gene (SEQ ID NO: 27) which encodes the protein having the amino acid sequence of SEQ ID NO: 28. (GenBank Accession No. NP_417969 [gi:16131384]).

The homologs of the gadE gene are, as with the evgA gene homologs described above, genes which are derived from other microorganisms which have high similarity in structure to the *Escherichia* gadE gene, improve the ability to produce an L-amino acid, and exhibit transcription factor activity when introduced into the host. The gadE gene homologs include a gene cloned from the synthetic oligonucleotides of SEQ ID NOS: 19 and 20.

The ydeO gene can be isolated or derived from (native to) Escherichia bacterium and its homologs. An example of ydeO gene of Escherichia coli includes a gene (SEQ ID NO: 27) which encodes the protein having the amino acid sequence of SEQ ID NO: 28. (GenBank Accession No. NP_417969 [gi:16131384]).

The homologs of the ydeO gene are, as with the ydeO gene homologs described above, genes which are derived from other microorganisms which have high similarity in structure to the ydeO gene of a bacterium of the genus Escherichia, improve the ability to produce L-amino acid, and exhibit transcription factor activity when introduced into the host. The ydeO gene homologs include a gene cloned from the synthetic oligonucleotides of SEQ ID NOS: 21 and 22.

The evgA, gadE, or ydeO genes are not limited to the wild-type genes, and as long as the function of the encoded protein, i.e., the transcription factor activity, is not impaired, the proteins encoded by these genes can also include mutant or artificially modified products. Such products may have a sequence which includes one or several amino acid substitutions, deletions, insertions, additions, or the like, at one or more positions in the amino acid sequence of SEQ ID NO: 24, 28, or 30. Here, the term "several" differs depending on the position of the amino acid residues in the stereostructure of the protein or the type of the amino acid. Specifically, this number can be 1 to 20, preferably 1 to 10, and more preferably 1 to 5. The above substitutions, deletions, insertions, or additions are conservative mutations that preserve transcription factor activity. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Specific examples of substitutions that are considered to be conservative include: substitution of Ala with Ser or Thr; substitution of Arg with Gln, His, or Lys; substitution of Asn with Glu, Gln, Lys, His, or Asp; substitution of Asp with Asn, Glu, or Gln; substitution of Cys with Ser or Ala; substitution of Gln with Asn, Glu, Lys, His, Asp, or Arg; substitution of Glu with Gly, Asn, Gln, Lys, or Asp; substitution of Gly with Pro; substitution of His with Asn, Lys, Gln, Arg, or Tyr; substitution of Ile with Leu, Met, Val, or Phe; substitution of Leu with Ile, Met, Val, or Phe; substitution of Lys with Asn, Glu, Gln, His, or Arg; substitution of Met with Ile, Leu, Val, or Phe; substitution of Phe with Trp, Tyr, Met, Ile, or Leu; substitution of Ser with Thr or Ala; substitution of Thr with Ser or Ala; substitution of Trp with Phe or Tyr; substitution of Tyr with His, Phe, or Trp; and substitution of Val with Met, Ile, or Leu. Substitutions, deletions, insertions, additions, or inversions and the like of the amino acids described above include naturally occurring mutations (mutant or variant) as a result in differences in species, or individual differences of microorganisms that express the evgA, gadE, and ydeO genes. Such genes can be obtained by modifying the nucleotide sequences shown in SEQ ID NOS: 23, 25, and 29 using, for example, site-directed mutagenesis, so that the site-specific amino acid residue in the protein encoded includes substitutions, deletions, insertions, or additions.

Moreover, the evgA, gadE, or ydeO genes include sequences which encode a transcription factor that has at least 80%, preferably at least 90%, more preferably at least 95% or even more preferably at least 97% homology with the entire amino acid sequences of SEQ NOS. 26, 30, or 32, respectively. Also, the evgA, gadE, or ydeO genes also include sequences in which codons are substituted with equivalent codons that are more readily utilized by the host into which these genes are respectively introduced. Likewise, as long as the evgA, gadE, or ydeO gene product maintains the function of the transcription factor, its N terminal or C terminal may be extended or removed. For example, 50 or less, preferably 20 or less, more preferably 10 or less, and even more preferably 5 or less amino acid residues may be extended or removed. More specifically, a gene which encodes a protein having from 5 to 50 amino acids of SEQ ID NOS:24, 18, or 30 extended or removed from the N terminal, and/or the C terminal may be used.

Also, variants of the genes can be obtained by conventional mutation treatments of the microorganism, such as in vitro mutation of the evgA, gadE, or ydeO genes using hydroxylamine, or the use of ultraviolet light or a known mutation agent, such as N-methyl-N'-nitro-N-nitrosoguanidine (NTG) or Ethyl Methyl Sulfonate (EMS). Whether or not these genes encode a protein that has transcription factor activity can be confirmed, for example, by expressing these genes in the appropriate cells, and investigating if transcription factor activity is present.

The evgA, gadE, or ydeO genes can also hybridize under stringent conditions with a nucleotide sequence complementary to the nucleotide sequence of SEQ ID NO: 23, 27, or 29, respectively, or with a probe prepared from these sequences, and which encodes proteins having transcription activity. Here, the term "stringent conditions" refers to conditions under which so-called specific hybrids are formed and nonspecific hybrids are not formed. Although it is difficult to clearly express such conditions in numbers, these conditions include when highly homologous fragments of DNA, for example, DNAs having homology no less than 70%, hybridizes each other and DNAs having homology lower than the above do not hybridize each other. Alternatively, stringent conditions are exemplified by washing once or preferably two to three times, at a temperature and salt concentration of, for example, 60° C., 1×SSC, 0.1% SDS, preferably 0.1× SSC, 0.1% SDS, and more preferably, 68° C., 0.1×SSC, 0.1% SDS.

As a probe, a nucleotide sequence of SEQ ID NO:23, 27 or 29 or a part of these sequences may also be used. Such a probe can be prepared employing PCR in which a DNA fragment containing one of these nucleotide sequences is used as the template, with an oligonucleotide prepared based on the nucleotide sequence of SEQ ID NO: 23, 27, or 29 as the primer. For example, when a DNA fragment of a length of about 300 bp is used as the probe, the washing conditions for the hybridization are 50° C., 2×SSC, and 0.1% SDS.

The expression of the evgA, gadE, or ydeO gene can be enhanced by employing, for example, genetic recombination techniques to increase the number of copies of the gene(s) in the cell. For example, a DNA fragment containing the evgA, gadE, or ydeO gene is ligated with a vector, preferably a multicopy type vector, which is able to function in the host microorganism. The microorganism is then transformed with this recombinant DNA.

When the evgA, gadE, or ydeO gene of Escherichia coli is used, these genes can be obtained by PCR (PCR: polymerase chain reaction; see White, T. J. et al., Trends Genet. 5, 185 (1989)) in which the genomic DNA of Escherichia coli is used as the template, and a primer is prepared based on the nucleotide sequence of SEQ ID NO: 22, 27, or 29, for example, the primers shown in SEQ ID NOS: 17 and 18 for the evgA gene, the primers shown in SEQ ID NOS: 19 and 20 for the gadE gene, or the primers shown in SEQ ID NOS: 21 and 22 for the ydeO gene. The evgA, gadE, and ydeO genes of other microorganisms belonging to the family Enterobacteriaceae can also be obtained from known evgA, gadE, and ydeO genes in those microorganisms or evgA, gadE, and ydeO genes in microorganisms of other species, or the genomic DNA or genomic DNA library of microorganisms, using PCR wherein primers are prepared based on other sequence information of the transcription factor, or the hybridization method wherein the probe is prepared based on the above-mentioned sequence information. Incidentally, the genomic DNA can be prepared from DNA donor microorganisms. For example, Saito and Miura's method, etc., (see H. Saito and K. Miura, Biochem. Biophys. Acta, 72, 619 (1963), Seibutsu Kogaku Jikkensho [Bioengineering Experiments], edited by The Society of Biotechnology, Japan, pp. 97-98, Baifukan, 1992), may be used.

Next, the recombinant DNA is prepared by ligating the PCR-amplified evgA, gadE, or ydeO gene with a DNA vector capable of functioning in the cells of the host microorganism. The chosen vector should be autonomously replicable in the cells of the host microorganism. Examples of autonomously replicable vectors for $Escherichia\ coli$ include pUC19, pUC18, pHSG299, pHSG399, pHSG398, pACYC184, (pHSG and pACYC are available from Takara Bio Inc.), RSF1010, pBR322, and pMW219 (pMW is available from Nippon Gene Co., Ltd.), pSTV29 (available from Takara Bio Inc.), etc.

Recombinant DNA prepared as described above may be introduced to a microorganism in accordance with known transformation methods. For example, the permeability of the DNA may be increased by treating the recipient bacteria with calcium chloride, as reported with regards to $Escherichia\ coli$ K-12 (Mandel, M. and Higa, A., J. Mol. Biol., 53, 159 (1970)). Another method is to introduce the DNA after preparing competent cells from the cells at the growth phase, as reported with regards to $Bacillus\ subtilis$ (Duncan, C. H., Wilson, G. A. and Young, F. E., Gene, 1, 153 (1977)). Also, another method is to change the host microorganism, as known for $Bacillus\ subtilis$, actinomycetes and yeast, into the protoplast or spheroplast state. Cells in this state can easily take up the recombinant DNA (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75 1929 (1978)).

The copy number of the evgA, gadE, or ydeO gene can be increased by integrating multiple copies of the evgA, gadE, or ydeO gene as described above onto the genomic DNA of the microorganism. This can be performed by homologous recombination using a target sequence which is present in multiple copies on the genomic DNA, such as repetitive DNA and inverted repeats present on the ends of transposable elements. Also, these genes may be ligated in tandem, with the evgA, gadE, or ydeO gene existing on the genome or incorporated in multiple copies into unnecessary genes on the genome. These genes can be introduced using a temperature-sensitive vector or integration vector.

As disclosed in JP2-109985A, it is also possible to incorporate the evgA, gadE, or ydeO gene into a transposon, and transfer it so that multiple copies of the gene are integrated into the chromosomal DNA. Integration of the evgA, gadE, or ydeO gene into the genome can be confirmed by Southern hybridization using a probe having a part of the evgA, gadE, or ydeO gene.

Aside from increasing the copy number of the gene described above, expression of the evgA, gadE, or ydeO gene can also be enhanced employing the methods described in WO00/18935. These method include, for example, substituting the expression regulatory sequence such as a promoter of the evgA, gadE, or ydeO gene, etc., on the genomic DNA or plasmid with a stronger one, creating a consensus sequence of the −35, −10 regions of each gene, amplifying a regulator which can enhance the expression of the evgA, gadE, or ydeO gene, and deleting or weakening a regulator which would decrease the expression of the evgA, gadE, or ydeO gene. For example, the lac promoter, trp promoter, trc promoter, tac promoter, araBA promoter, lambda phage PR promoter, PL promoter, tet promoter, T7 promoter, φ10 promoter, etc., are all known as strong promoters. It is also possible to introduce a nucleotide substitution, etc., into the promoter region or SD region of the evgA, gadE, or ydeO gene so to increase the promoter strength. Examples of methods for evaluating the strength of promoters and examples of strong promoters are described in articles by Goldstein et al. (Prokaryotic promoters in biotechnology. Biotechnol. Annu. Rev., 1, 105-128 (1995)), etc. Furthermore, substitution of several nucleotides in the spacer region between the ribosome binding site (RBS) and the start codon, particularly in the sequence immediately upstream of the start codon, is known to have a strong effect on mRNA translation efficiency. The expression regulatory region such as a promoter etc. of the evgA, gadE, or ydeO gene, can be identified by a promoter-probe vector and gene analysis software such as GENETYX, etc. Expression of the evgA, gadE, or ydeO gene can be enhanced by substitutions or modifications of these promoters. Expression regulatory sequences can be substituted, for example, by employing temperature-sensitive plasmids or the Red-driven integration method (WO2005/010175).

A mutation which increases transcription of a gene whose expression is regulated by the evgA, gadE, or ydeO gene may also be introduced into the evgA, gadE, or ydeO gene. Examples of mutations which increase the activity of the protein encoded by the evgA, gadE, or ydeO gene are a mutation of the promoter sequence, which increases the transcription amount of the evgA, gadE, or ydeO gene, and a mutation within the encoded region of the gene, which increases the specific activity of the transcription.

The protein encoded by the evgA, gadE, or ydeO gene is activated by histidine kinase EvgS. Therefore, in expression of the evgA, gadE, or ydeO gene may be increased in the host microorganism by increasing the expression of the evgS gene that encodes EvgS. The evgS gene includes the evgS gene derived or isolated from an $Escherichia$ bacterium and its homologs. For example, the evgS gene of $Escherichia\ coli$ is exemplified by a gene (SEQ ID NO: 25) that encodes a protein having the amino acid sequence of SEQ ID NO: 26. (GenBank Accession No. NP_417969 [gi:16131384]).

The homologs of the evgS gene include those which are derived from other microorganisms, have high similarity in structure to the $Escherichia$ evgS gene, improve the ability to produce an L-amino acid, and exhibit transcription factor activity when introduced into the host. Examples of evgS homologs include evgS genes of the genera $Salmonella$, $Shigella$, and $Yersinia$ registered at GenBank. Furthermore, based on the homology with the genes given in the above examples, evgS genes may be cloned from coryneform bacteria, such as $Corynebacterium\ glutamicum$, $Brevibacterium\ lactofermentum$, etc.; bacteria of the genus $Pseudomonas$, such as $Pseudomonas\ aeruginosa$, etc.; bacteria of the genus $Mycobacterium$, such as $Mycobacterium\ tuberculosis$, etc.; and bacteria of the genus *Bacillus*. Ones with different gene names are acceptable as long as they are highly homologous with the evgS of the bacteria of the genus *Escherichia*. For example, in *Escherichia coli*, the evgS gene forms an operon with the evgA gene, and can be obtained along with the evgA gene by PCR using the synthetic oligonucleotides of SEQ ID NOS: 17 and 18. With other microorganisms, it is expected that these genes can be obtained likewise using the oligonucleotides of SEQ ID NOS: 17 and 18.

The evgS gene is not limited to a wild-type gene and may include a variant evgS gene as long as the function of the protein, i.e., the transcription factor activity, is not impaired. Such a variant may include a mutant or artificially modified protein having a sequence including one or several amino acid substitutions, deletions, insertions, additions, or the like at one or more positions in the amino acid sequence of SEQ ID NO: 26, i.e., a protein that has conservative mutation. The terms "several" and "conservative mutation" are the same as those described above regarding the evgA gene, gadE gene, and ydeO gene.

The expression of evgS can be increased using the same method as used for the evgA, gadE, and ydeO genes as described above.

The expression of the evgA, gadE, or ydeO gene can be increased using one of the same method or different methods may be used for each gene.

2. Method for Producing L-Amino Acid

The method for producing L-amino acid of the present invention includes the steps of culturing the microorganism in a medium, producing and accumulating the L-amino acid in said medium or in the cells of the microorganism, and collecting the L-amino acid from said medium or the cells.

Conventional mediums typically used in the fermentation and production of L-amino acids using microorganisms may be used. That is, an ordinary medium containing a carbon source, nitrogen source, inorganic ions, and other organic components as needed may be used. Carbon sources include a sugar such as glucose, sucrose, lactose, galactose, fructose, a starch hydrolysase, etc., an alcohol such as glycerol, solbitol, etc., an organic acid such as fumaric acid, citric acid, succinic acid, etc. Of these, glucose, fructose, and sucrose may be advantageously used. Nitrogen sources include an inorganic ammonium salt such as ammonium sulfate, ammonium chloride, ammonium phosphate, etc., an organic nitrogen such as a soybean hydrolysate, etc., ammonia gas, ammonia water, etc. As the organic micronutrient source, it is advantageous that the medium include an appropriate amount of the required substances, such as vitamin B1, L-homoserine, etc., or yeast extract, etc. In addition to these, according to necessity, small amounts of potassium phosphate, magnesium sulfate, iron ions, manganese ions, etc., can be added. The medium may be either natural or synthetic as long as it contains a carbon source, nitrogen source, inorganic ions, and, as needed, other organic micronutrients.

An amino acid which improves the growth of a microorganism or productivity of target substance may be added to the medium. For example, it is advantageous that L-threonine, L-homoserine or L-isoleucine is added for L-lysine fermentation. L-isoleucine, L-lysine, L-glutamic acid or L-homoserine is added for L-threonine fermentation, and L-phenylalanine or L-tyrosine or the like is added for L-tryptophan fermentation. The concentration of the L-amino acid is around 0.01-10 g/L.

The culture should be performed under aerobic conditions for 1-7 days at a temperature of 24° C.-37° C., with a pH of 5-9. To adjust the pH, an inorganic or organic acidic or alkali substance, and ammonia gas and the like may be used. L-amino acids can be collected from the fermentation broth using a combination of a conventional ion-exchange resin method, precipitation method, and other known methods. If the L-amino acid accumulates inside the cells, the cells can be disrupted by ultrasonication, etc. Then, cell debris can be removed by centrifugal separation to obtain the supernatant, from which the L-amino acid can be recollected using an ion-exchange resin method, etc.

EXAMPLES

The present invention will be explained more specifically below with reference to the following non limiting Examples.

Reference Example 1

Construction of L-Tryptophan-Producing Bacteria 1-1. Introduction of the serA Gene The phosphoglycerate dehydrogenase gene (serA) is present on the plasmid pGH5 (WO9408031) and was inserted into the genome of a bacterium using the transposon Mud. Plasmid pCE1134 (JP2-109985A) which contains MudII1734 was digested with BamHI to remove a DNA fragment containing the lac operon, the termini were blunt-ended, and a SmaI linker was inserted. This plasmid was redigested with SmaI, and self-closed to form a circular plasmid named pMu1134. A DNA fragment containing serA was excised from plasmid pGH5 by cleaving with ScaI and SalI, and the termini of the fragment were blunt-ended. Then the fragment was inserted into the SmaI site of the above described pMu1134. Thus, the plasmid pMudserA with Mud containing the pGH5-derived serA gene (named MudserA) was constructed.

The L-tryptophan-producing bacterial strain SV164 (WO9408031), which is desensitized to anthranilate synthase was used to obtain the bacterial strain L1 in which MudserA was transferred onto the genome using acquisition of kanamycin resistance as an index. From the results of a Southern hybridization experiment, it was determined that there was only one location where the MudserA was inserted in the L1 strain. Also, with the cloning of a genomic DNA fragment containing MudserA by PCR and the determination of its nucleotide sequence, it was determined that the insertion was at the position No. 240, 950 on the *E. coli* K-12 genome (GenBank Accession No. U00096).

1-2. Introduction of the Trp Operon

Next, the copy number of the trp operon was increased by inserting the trp operon into the genome using a transposon. The trp operon genes were excised from the plasmid pGX100. pGX100 was constructed by inserting a DNA fragment derived from *E. coli* MTR#2 (U.S. Pat. No. 4,371,614) into the plasmid pBR313. *E. coli* MTR#2 has a desensitized trpE gene. A DNA fragment containing the approximately 7.6 kb trp operon can be excised from the plasmid by cleaving with XhoI and SmaI. A DNA fragment containing the trp operon was excised from pGX100 by cleaving with XhoI and SmaI, and the termini of the fragment were blunt-ended. Then, the fragment was inserted into the SmaI site of the above-described pCE1134. The same DNA fragment containing the trp operon can also be cloned directly from the *E. coli* MTR#2 strain genomic DNA, employing PCR, using the primers SEQ ID NOS: 1 and 2. As described above, plasmid pMudtrpG' lac was constructed. This plasmid contains Mud into which the trp operon genes derived from the MTR#2 strain had been inserted (named MudtrpG' lac).

Prior to increasing the copy number of MudtrpG' lac by inserting MudtrpG' lac into the genome, the host strain was made lactose-assimilation deficient for the purpose of using complementation of lactose-assimilating ability as a selection marker for the strain. The ilvG gene of the L-threonine-producing bacterium VKPM B-3996 (U.S. Pat. No. 5,175,107) was P1-transduced into the L1 strain to render it L-valine resistant (See WO2005/103228). The P1 transduction was conducted and transductants were spread on an M9 minimum medium (4 g/L glucose, 12.8 g/L Na$_2$HPO$_4$.7H2O, 3 g/L KH$_2$PO4, 0.5 g/L NaCl, 1 g/L NH$_4$Cl, 5 mM MgSO$_4$, 0.1 mM CaCl$_2$, 1 mg/L thiamine, 20 mg/l L-Phe, 20 mg/L L-Tyr, 20 mg/L L-Met, 3 mg/L pyridoxine, 20 mg/L L-Val, 20 mg/L tetracycline), and a colonies resistant to valine were obtained, and named L1ValR.

lacZ98::Tn10 was P1-transduced into L1ValR from the ME8581 strain (HfrH (valS←uxuAB):lacZ98::Tn10 relA1 thi-1, deposited at the National Institute of Genetics), with Tn10-derived tetracycline resistance as the indicator. The strain obtained was lactose-assimilation deficient, as expected. Next, in order to obtain a strain with deficient lactose-assimilating ability, but without Tn10, a tetracycline-sensitive strain 14-1-lac-tets was obtained from the transduced strains through the replica method. The lactose-assimilating ability was still deficient in the 14-1-lac-tets strain. When confirming the Tn10 status of the strain by Southern hybridization, no band hybridizing with the tet gene was detected, but a band hybridizing with the IS10 region of Tn10 was detected. Therefore, it was determined that IS10 remains on the lacZ gene.

Using pMudtrpG' lac and the 14-1-lac-tets strain, bacterial strain No. 202 in which MudtrpG' lac was transferred onto the genome was obtained, with complementation of lactose-assimilating ability as the indicator. If the inserted transposon, or the gene on transposon, tends to drop off from the transposon-inserted strain, a subculture may be performed in a nutrient-rich medium to select a bacterial strain which stably retains kanamycin resistance, lactose-assimilating ability, etc. As a result of Southern hybridization, it was determined that there was only one location where MudtrpG' lac was inserted into the No. 202 strain. Also, with the cloning of a genomic DNA fragment containing MudtrpG' lac by PCR and the determination of its nucleotide sequence, it was determined that the insertion was at the position No. 530,249 on the *E. coli* K-12 genome (GenBank Accession No. U00096).

Next, the scrK, scrY, scrA, scrB, and scrR genes, which are involved in sucrose assimilation, were introduced into No. 202 by P1 transduction, and the resulting bacterial strain was designated No. 202 scr (see WO90/04636).

1-3. Construction of a Plasmid for Disrupting iclR

The iclR fragment was amplified by PCR using Pyrobest DNA Polymerase (Takara Shuzo) according to the attached instruction manual. For the PCR reaction, oligonucleotides of SEQ ID NOS: 3 and 4 were used as the primers, with the W3110 genome extracted using an RNA/DNA maxi Kit (QIAGEN) as the template. After the PCR, the amplified DNA fragment was purified using Wizard PCR Preps (Promega). The purified DNA fragment was digested with restriction endonucleases EcoRI and Hind III (Takara Shuzo), then underwent phenol chloroform treatment and ethanol precipitation to obtain purified DNA. This fragment and pUC18 (Takara Shuzo), which was digested with the same enzymes and then purified, were ligated using DNA ligation Kit Ver. 2 (Takara Shuzo). With this ligation reaction solution, the JM109 competent cells (Takara Shuzo) were transformed, and then spread onto an LB agar plate containing 50 µg/mL ampicillin (Amp) (Meiji Seika) (LB+Amp plate), and colonies were selected at 37° C. The colonies were cultured in a test tube using an LB medium containing 50 µg/mL Amp at 37° C., and the plasmid was extracted using the automatic plasmid extractor PI-50 (Kurabo).

The obtained plasmid pUCiclR was digested with restriction endonuclease EcoO65I (Takara Shuzo), blunt-ended, and ligated using a BKL kit (Takara Shuzo). With the ligation reaction solution, JM109 was transformed, and colonies were selected as described above, and the plasmid was extracted. The obtained plasmid was digested with EcoRI and HindIII, purified, and ligated with the temperature-sensitive plasmid pTS1, which had been digested with the same enzymes and purified. pTS1 was obtained by replacing a PstI-HindIII fragment of pMAN031 (see J. Bacteriol. 162, 1196-1202 (1985), FIG. 1) with a PstI-HindIII fragment of pBR322 (Takara Shuzo). JM109 was transformed with the ligation reaction solution, and colonies were selected on the LB+Amp plate at 30° C. The colonies were cultured at 30° C. in a test tube using LB medium containing 50 µg/mL Amp, and the plasmid was extracted as described above. The plasmid which generates a fragment with an expected length by digestion with EcoRI and HindIII was designated as the iclR disrupting plasmid pTSΔiclR.

1-4. Obtaining an iclR-Disrupted Strain

No. 202 scr was transformed with pTSΔiclR, and colonies were selected on the LB+Amp plate at 30° C. After liquid culture was performed overnight at 30° C., the culture was diluted by $10^{-3}$ and spread on the LB+Amp plate, and the colonies were selected at 42° C. Specifically, the culture was spread on the LB+Amp plate and cultured at 30° C., cells which covered ⅛ of the plate were suspended in a 2 mL LB medium, and cultured with shaking for 4-5 hours at 42° C. The cells diluted by $10^{-5}$ were spread on the LB plate and colonies were obtained. Of these, one hundred colonies were spread on the LB plate and LB+Amp plate, respectively, and their growth was confirmed, and by which the Amp sensitivity and resistance were confirmed. Amp-sensitive strains were examined by colony PCR using the oligonucleotides of SEQ ID NOS: 3 and 4 as the primers. As a result, an iclR-deficient strain (No. 202ΔiclR) in which an amplified fragment could not be cut with EcoO65I was obtained.

Example 1

Construction of a Plasmid for Enhancing the Expression of the evgAS, gadE, and ydeO Genes 1-1. Construction of a Plasmid for Enhancing the Expression of the evgA and evgS Genes The entire nucleotide sequence of the genome of *Escherichia coli* (*Escherichia coli* K-12 strain) has been reported (Science, 277, 1453-1474 (1997)), and it is known that evgAS forms an operon structure. Based on the nucleotide sequences of the evgAS genes (GenBank Accession Nos. AAC75428 and AAC75429) which were reported in the above report, the 5' primer SEQ ID NO:17 having a HindIII site, and the 3' primer SEQ ID NO:18 having an EcoRI site were synthesized. Using these primers, PCR was performed with the genomic DNA of the *Escherichia coli* W3110 strain as the template, and the amplified product was treated with restriction endonucleases HindIII and EcoRI to obtain a fragment containing the evgAS genes. The purified PCR product was ligated to vector pMW118 (Nippon Gene Co., Ltd.) which had been digested with HindIII and EcoRI, thus constructing the plasmid pMW-evgAS for amplifying the evgAS operon.

1-2. Construction of a Plasmid for Enhancing the Expression of gadE

The entire nucleotide sequence of the genome of *Escherichia coli* (*Escherichia coli* K-12 strain) has been reported (Science, 277, 1453-1474 (1997)). Based on the nucleotide sequence of the gadE gene (GenBank Accession No. AAC76537) which was reported in the above report, the 5' primer SEQ ID NO:19 having a BamHI site, and the 3' primer SEQ ID NO:20 having a HindII site were synthesized. Using these primers, PCR was performed with the genomic DNA of the *Escherichia coli* W3110 strain as the template, and the amplified product was treated with restriction endonucleases HindIII and BamHI to obtain a fragment containing the gadE gene. The purified PCR product was ligated to vector pMW118 (Nippon Gene Co., Ltd.), which had been digested with HindIII and BamHI, thus constructing the plasmid pMW-gadE for amplifying gadE.

1-3. Construction of a Plasmid for Enhancing ydeO

The entire nucleotide sequence of the genome of *Escherichia coli* (*Escherichia coli* K-12 strain) has been reported (Science, 277, 1453-1474 (1997)). Based on the nucleotide sequence of the ydeO gene (GenBank Accession No. AAC74572) which was reported in the above report, in the 5' primer SEQ ID NO:21 having a HindIII site, and the 3' primer SEQ ID NO:22 having a EcoRI site were synthesized. Using these primers, PCR was performed with the genomic DNA of the *Escherichia coli* W3110 strain as the template, and the amplified product was treated with restriction endonucleases HindIII and EcoRI to obtain a fragment containing the ydeO gene. The purified PCR product was ligated to vector pMW118 (Nippon Gene Co., Ltd.), which had been digested with HindIII and EcoRI, thus constructing the plasmid pMW-ydeO for amplifying ydeO.

Example 2

Effect of evgAS, ydeO, and gadE Gene Amplification on an L-Tryptophan-Producing Strain of a Bacterium of the Genus *Escherichia*

The L-tryptophan-producing strain No. 202ΔiclR constructed in Reference Example 1 was transformed with each of the gadE-amplifying plasmid pMW-gadE, evgAS-amplifying plasmid pMW-evgAS, and the ydeO-amplifying plasmid pMW-ydeO created in Example 1, thus obtaining ampicillin-resistant strains. After confirming that these plasmids had been introduced, the strain with the gadE-amplifying plasmid pMW-gadE was designated No. 202ΔiclR/gadE, the strain with the evgAS-amplifying plasmid pMW-evgAS was designated No. 202ΔiclR/evgAS, and the strain with the ydeO-amplifying plasmid pMW-ydeO was designated No. 202ΔiclR/ydeO.

evgAS, ydeO, or gadE may be amplified in the same manner using known L-tryptophan-producing bacteria other than the No. 202ΔiclR strain.

The above-described strains were cultured in LB medium containing 50 mg/L ampicillin at 37° C. until the OD600 became approx. 0.6. An equal volume of 40% glycerol solution was added to the culture broth, stirred, and then appropriate amounts were dispensed and stored at −80° C. to make the glycerol stock.

After melting the glycerol stocks of these strains, 100 mL of each was homogeneously spread onto an L plate containing 50 mg/L ampicillin, and the plate was incubated at 37° C. for 24 hours. Approx. ⅛ of the cells on the plate were inoculated into a 20 mL fermentation medium with 50 mL ampicillin in a 500 mL Sakaguchi flask, and cultured at 37° C. for 48 hours using a reciprocal shaking incubator. After the culture, the amount of L-tryptophan which had accumulated in the medium was measured using an amino acid-analyzer L-8500 (Hitachi). The medium composition used for the culture was as follows.

L-Tryptophan-Producing Medium:

| | |
|---|---|
| Glucose | 40 g/L |
| $(NH_4)_2SO_4$ | 15 g/L |
| $KH_2PO_4$ | 1.5 g/L |
| $MgSO_4 \cdot 7H_2O$ | 0.3 g/L |
| $FeSO_4 \cdot 7H_2O$ | 0.01 g/L |
| $MnSO_4 \cdot 7H_2O$ | 0.01 g/L |
| Yeast Extract | 2.0 g/L |
| ThiaminHCl | 0.005 g/L |
| Pyridoxine | 0.03 g/L |
| L-Met | 0.05 g/L |
| L-Phe | 0.1 g/L |
| L-Tyr | 0.1 g/L |
| $CaCO_3$ | 30 g/L |

Adjusted to pH 7.0 with KOH, autoclaved at 120° C. for 20 min. Glucose and $MgSO_4 \cdot 7H_2O$ were mixed and sterilized separately from other components. $CaCO_3$ was added after dry-heat sterilization.

The OD600 and L-tryptophan accumulation at the 48th hour are shown in Table 1.

TABLE 1

Effect of evgAS, ydeO, and gadE amplification on Trp-producing bacteria No.202ΔiclR

| Strain | OD (600 nm) | Trp concentration (g/l) |
|---|---|---|
| No.202ΔiclR | 7.0 | 7.2 |
| No.202ΔiclR/evgAS | 7.2 | 7.6 |
| No.202ΔiclR/ydeO | 7.0 | 7.4 |
| No.202ΔiclR/gadE | 7.4 | 7.5 |

No. 202ΔiclR/evgAS, No. 202ΔiclR/ydeO, and No. 202ΔiclR/gadE, which are the evgAS, ydeO, and gadE gene-amplified strains, respectively, each indicated an increase in the accumulation of L-tryptophan as compared to the control No. 202ΔiclR.

Example 3

Effect of evgAS, ydeO, and gadE Amplification on an L-Threonine-Producing Strain of a Bacterium of the Genus *Escherichia*

*Escherichia coli* VKPM B-5318 strain (see EP0593792) was used as an L-threonine-producing strain of a bacterium of the genus *Escherichia*

The VKPM B-5318 strain was transformed with each of the gadE-amplifying plasmid pMW-gadE, evgAS-amplifying plasmid pMW-evgAS, and the ydeO-amplifying plasmid pMW-ydeO constructed in Example 1, thus obtaining ampicillin-resistant strains. After confirming that these plasmids had been introduced, the strain with the gadE-amplifying plasmid pMW-gadE was designated B5318/gadE, the strain with the evgAS-amplifying plasmid pMW-evgAS was designated B5318/evgAS, and the strain with the ydeO-amplifying plasmid pMW-ydeO was designated B5318/ydeO.

evgAS, ydeO, or gadE may be amplified in the same manner using other known L-threonine-producing bacteria.

The above-described strains were cultured in LB medium containing 50 mg/L ampicillin at 37° C. until the OD600 became approx. 0.6. An equal volume of 40% glycerol solution was added to the culture broth, stirred, and then appropriate amounts were dispensed and stored at −80° C. to make the glycerol stock.

After melting the glycerol stocks of these strains, 100 mL of each was homogeneously spread onto an L plate containing 50 mg/L ampicillin, and the plate was incubated at 37° C. for 24 hours. Approx. ⅛ of the cells on the plate were inoculated into a 20 mL fermentation medium described below with 50 mL ampicillin in a 500 mL Sakaguchi flask, and cultured at 37° C. for 48 hours using a reciprocal shaking incubator. After the culture, the amount of L-threonine which had accumulated in the medium was measured using an amino acid-analyzer L-8500 (Hitachi). The medium composition used for the culture was as follows.

L-Threonine-Producing Medium:

| | |
|---|---|
| Glucose | 40 g/L |
| $(NH_4)_2SO_4$ | 16 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast Extract | 2.0 g/L |
| $CaCO_3$ (Japanese Pharmacopoeia) | 30 g/L |

Adjusted to pH 7.0 with KOH, autoclaved at 120° C. for 20 min. Glucose and $MgSO_4 \cdot 7H_2O$ were mixed and sterilized separately. $CaCO_3$ was added after dry-heat sterilization.

The OD600 and L-threonine accumulation at the 48th hour are shown in Table 2.

TABLE 2

Effect of evgAS, ydeO, and gadE amplification on

| Strain | OD (600 nm) | Thr concentration (g/l) |
|---|---|---|
| B5318 | 8.1 | 6.7 |
| B5318/evgAS | 8.1 | 6.9 |
| B5318/ydeO | 7.9 | 7.0 |
| B5318/gadE | 8.4 | 7.2 |

B5318/evgAS, B5318/ydeO, and B5318/gadE, which are the evgAS, ydeO, and gadE gene-amplified strains, each indicated an increase in the accumulation of L-threonine compared to the control VKPM B-5318.

Example 4

Construction of an L-Lysine-Producing Bacterium 4-1. Construction of a Strain in which the cadA and ldcC Genes that Encode Lysine Decarboxylase are Disrupted First, a strain which does not produce lysine decarboxylase was constructed. Lysine decarboxylase isozymes are encoded by the cadA gene (GenBank Accession No. NP_418555. SEQ ID NO: 31) and the ldcC gene (GenBank Accession No. NP_414728. SEQ ID NO: 33) (see WO96/17930). The WC196 strain (see WO96/17930), which is an AEC (S-(2-aminoethyl)-cysteine)-resistant strain, was used as the parent strain to construct the Escherichia coli L-lysine-producing strain.

The cadA and ldcC genes encoding lysine decarboxylase were deleted using a method called "Red-driven integration", which was initially developed by Datsenko and Wanner (Proc. Natl. Acad. Sci. USA. 97. 6640-6645 (2000)), and a λ phage excision system (J. Bacteriol. 184. 5200-5203 (2002)). According to the "Red-driven integration" method, a gene-disrupted strain can be constructed in a single step by employing a PCR product obtained by using primers for which a part of the target gene was designed at the 5' terminus and a part of the antibiotic-resistant gene was designed at the 3'terminus. Furthermore, in combination with the λ phage excision system, the antibiotic-resistant gene integrated into the gene-disrupted strain can be removed (JP2005-058227A).

4-2. Disruption of the cadA Gene

Plasmid pMW118-attL-Cm-attR (WO2005/010175) was used as the PCR template. pMW118-attL-Cm-attR is a plasmid wherein the attL and attR genes, which are the attachment sites of the λ phage, and the cat gene, which is an antibiotic-resistant gene, have been inserted into pMW118 (Takara Bio Inc.) in the following order: attL-cat-attR.

PCR was conducted using the primers SEQ ID NOS: 35 and 36, wherein each of the primers has a sequence corresponding to each ends of attL and attR at the 3' end, and has a sequence corresponding to a part of the target cadA gene at the 5' end.

The PCR product was purified using agarose gel, then introduced by electroporation to an Escherichia coli WC1-96 strain containing the plasmid pKD46, which has a temperature-sensitive replication origin. Plasmid pKD46 (Proc. Natl. Acad. Sci. USA. 97. 6640-6645 (2000)) contains the λ phage DNA fragments, which total 2154 bases, and include the genes (γ, β, exo genes) that encode Red recombinase in the λ Red homologous recombination system controlled by the arabinose-induced ParaB promoter (GenBank/EMBL Accession No. J02459, 31088th-33241st).

Competent cells for electroporation were prepared as follows. That is, an Escherichia coli WC1-96 strain cultured overnight at 30° C. in an LB medium containing 100 mg/L ampicillin was diluted 100 times in a 5 mL SOB medium containing ampicillin (20 mg/L) and L-arabinose (1 mM) (Molecular Cloning: Lab Manual $2^{nd}$ edition, Sambrook, J., et al., Cold Spring Harbor Laboratory Press (1989)). The diluted suspension was aerated at 30° C. until the OD600 reached approx. 0.6, and then the suspension was concentrated 100 times and washed three times with 10% glycerol to prepare it for electroporation. Electroporation was performed using 70 μL competent cells and approx. 100 ng PCR product. 1 mL SOC medium (Molecular Cloning: Lab Manual $2^{nd}$ edition, Sambrook, J., et al., Cold Spring Harbor Laboratory Press (1989)) was added to the post-electroporation cells, and cultured at 37° C. for 2.5 hours, then cultured on a plate medium of L-agar containing Cm (chloramphenicol) (25 mg/L) at 37° C., thus selecting the Cm-resistant recombinant. Next, to remove the pKD46 plasmid, the recombinant was subcultured twice on an L-agar medium containing Cm at 42° C., the ampicillin resistance of the colony obtained was tested, and an ampicillin-sensitive strain from which the pKD46 was omitted was obtained.

Deletion of the cadA gene in the mutant identified by the chloramphenicol-resistant gene was confirmed using the PCR. The cadA deficient strain obtained was designated WC196ΔcadA::att-cat.

Next, to remove the att-cat gene in the cadA gene, a helper plasmid, pMW-intxis-ts (WO2005/010175) was used. pMW-intxis-ts is a plasmid which contains a gene that encodes λ phage integrase (Int) and a gene that encodes excisionase (Xis).

The competent cells of the WC196ΔcadA::att-cat strain obtained as described above were prepared, transformed with helper plasmid pMW-intxis-ts, and cultured on a plate medium of L-agar containing 50 mg/L ampicillin at 30° C., thus selecting the ampicillin-resistant strain.

Next, to remove the pMW-intxis-ts plasmid, the ampicillin-resistant transformant was subcultured twice on an L-agar medium at 42° C. The ampicillin and chloramphenicol resistance of the colony were tested, and a chloramphenicol and ampicillin-sensitive strain from which the att-cat and pMW-intxis-ts were removed was obtained. This strain was designated WC196ΔcadA.

4-3. Disruption of the ldcC Gene in the WC196ΔcadA Strain

The ldcC gene in the WC196ΔcadA strain was deleted by the technique described above, using primers SEQ ID NOS: 37 and 38. Thus, WC196ΔcadAΔldcC, which is a cadA, ldcC-disrupted strain, was obtained.

Example 5

Effect of evgAS Amplification on an L-Lysine-Producing Strain of an *Escherichia* Bacterium 5-1. Introduction of Lysine-Producing Plasmid into the WC196ΔcadAΔldcC Strain The WC196ΔcadAΔldcC strain was transformed with the lysine-producing plasmid pCAB1 which contains the dapA, dapB, and lysC genes (WO01/53459), to obtain the WC196ΔcadAΔldcC/pCAB1 strain (WC196LC/pCAB1).

The WC196LC/pCAB1 strain was transformed with the evgAS-amplifying plasmid pMW-evgAS, created in Example 1, thus obtaining an ampicillin-resistant strain. After confirming that the desired plasmid had been introduced, the evgAS-amplifying plasmid pMW-evgAS-introduced strain was designated WC196LC/pCAB1/evgAS.

evgAS may be amplified in the same manner using other known L-lysine-producing bacteria.

The strains created as above were cultured in LB medium containing 25 mL streptomycin and 50 mg/L ampicillin at 37° C. until the OD600 became approx. 0.6. An equal volume of 40% glycerol solution was added to the culture broth, stirred, and then appropriate amounts were dispensed and stored at −80° C. to make the glycerol stock.

5-2. Lysine-Producing Culture

After melting the glycerol stocks of these strains, 100 mL of each was homogeneously spread onto an L plate containing 50 mg/L ampicillin, and the plate was incubated at 37° C. for 24 hours. Approx. ⅛ of the cells on the plate obtained were inoculated into a 20 mL fermentation medium described below with 50 mL ampicillin in a 500 mL Sakaguchi flask, and cultured at 37° C. for 48 hours using reciprocal shaking. After the culture, the amount of L-lysine which had accumulated in the medium was measured using a Biotech-analyzer AS210 (Sakura Seiki). The medium composition used for the culture was as follows.

L-Lysine-Producing Medium:

| | |
|---|---|
| Glucose | 40 g/L |
| $(NH_4)_2SO_4$ | 16 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Yeast Extract | 2.0 g/L |
| $CaCO_3$ (Japanese Pharmacopoeia) | 30 g/L |

Adjusted to pH 7.0 with KOH, autoclaved at 120° C. for 20 min. Glucose and $MgSO_4 \cdot 7H_2O$ were mixed and sterilized separately. $CaCO_3$ was added after dry-heat sterilization.

The OD600 and L-lysine accumulation at the 48th hour are shown in Table 3.

TABLE 3

Effect of evgAS amplification on lysine-producing bacterium WC196LC/pCAB1

| strains | OD (600 nm) | Lys concentration (g/l) |
|---|---|---|
| WC196LC/pCAB1 | 7.3 | 14.3 |
| WC196LC/pCAB1/evgAS | 7.5 | 15.3 |

WC196LC/pCAB1/evgAS, which is the evgAS gene-amplified strain, indicated a significant increase in the accumulation of L-lysine compared to the control WC196LC/pCAB1.

Example 6

Effect of gadE Amplification on an L-Lysine-Producing Strain of an *Escherichia* Bacterium 6-1. Construction of an L-Lysine-Producing Strain in which the gadE Gene has been Enhanced A gadE gene fragment was excised from the plasmid pMW-gadE, which contains the gadE gene of the *Escherichia coli* W3110 strain created in Example 1, and the fragment was ligated with vector pUC18 (Takara Shuzo) and digested with HindIII and BamHI, thus constructing the gadE-amplifying plasmid pUC-gadE.

The WC196LC/pCAB1 strain was transformed with the above-mentioned pUC-gadE, thus obtaining an ampicillin-resistant strain. After confirming that the desired plasmid had been introduced, the strain with the gadE-amplifying plasmid pUC-gadE was designated WC196LC/pCAB1/pUC-gadE.

evgAS, ydeO, or gadE may be amplified in the same manner using other known L-lysine-producing bacteria. Amplification of these genes may be performed in any order or combination.

The strains created as above were cultured in LB medium containing 25 mg/L streptomycin and 50 mg/L ampicillin at 37° C. until the OD600 reached approx. 0.6. An equal volume of a 40% glycerol solution was added to the culture broth, stirred, and then appropriate amounts were dispensed and stored at −80° C. to make the glycerol stock.

6-2. Lysine-Producing Culture

After melting the glycerol stocks of these strains, 100 mL of each was homogeneously spread onto an L plate containing 25 mg/L streptomycin and 50 mg/L ampicillin, and the plate was incubated at 37° C. for 24 hours. Approx. ⅛ of the cells on the plate were inoculated into a 20 mL fermentation medium described below with 25 mg/L streptomycin and 50 mL ampicillin in a 500 mL Sakaguchi flask, and cultured at 37° C. for 48 hours using a reciprocal shaking incubator. After the culture, the amount of L-lysine which had accumulated in the medium was measured using a Biotech-analyzer AS210 (Sakura Seiki). The medium composition used for the culture was as follows.

L-Lysine-Producing Medium:

| | |
|---|---|
| Glucose or Fructose | 40 g/L |
| $(NH_4)_2SO_4$ | 16 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 7H_2O$ | 0.01 g/L |
| Isoleucine | 0.1 g/L |
| Yeast Extract | 2.0 g/L |
| $CaCO_3$ (Japanese Pharmacopoeia) | 30 g/L |

Adjusted to pH 7.0 with KOH, autoclaved at 120° C. for 20 min. Glucose and $MgSO_4.7H_2O$ were mixed and sterilized separately. $CaCO_3$ was added after dry-heat sterilization.

The OD600 and L-lysine accumulated at the 48th hour are shown in Table 4.

TABLE 4

Effect of gadE amplification on lysine-producing bacterium WC196LC/pCAB1 in glucose culture and fructose culture

| Strain | Carbon source | OD (600 nm) | L-lysine concentration (g/l) |
|---|---|---|---|
| WC196LC/pCAB1 | Glucose | 8.8 | 8.9 |
| WC196LC/pCAB1/pUCgadE | Glucose | 8.6 | 9.2 |
| WC196LC/pCAB1 | Fructose | 7.4 | 9.1 |
| WC196LC/pCAB1/pUCgadE | Fructose | 7.3 | 10.1 |

The gadE gene-amplified strain WC196LC/pCAB1/pUCgadE produced an increase in the accumulation of L-lysine in both glucose and fructose cultures compared to the control WC196LC/pCAB1, and in particular, a significant increase in the accumulation of L-lysine in the fructose culture was observed.

INDUSTRIAL APPLICABILITY

By using the microorganism of the present invention, L-amino acids can be efficiently produced by fermentation, specifically, L-lysine, L-threonine.

EXPLANATION OF SEQUENCE LISTING

SEQ ID NO: 1: primer for amplifying trp operon
SEQ ID NO: 2: primer for amplifying trp operon
SEQ ID NO: 3: primer for amplifying iclR gene
SEQ ID NO: 4: primer for amplifying iclR gene
SEQ ID NO: 5: nucleotide sequence of the iclR gene
SEQ ID NO: 6: sequence of an amino acid encoded by the iclR gene
SEQ ID NO: 7: nucleotide sequence of the aceA gene
SEQ ID NO: 8: sequence of an amino acid encoded by the aceA gene
SEQ ID NO: 9: nucleotide sequence of the aceB gene
SEQ ID NO: 10: sequence of an amino acid encoded by the aceB gene
SEQ ID NO: 11: nucleotide sequence of the aceK gene
SEQ ID NO: 12: sequence of an amino acid encoded by the aceK gene
SEQ ID NO: 13: nucleotide sequence of the trpA gene
SEQ ID NO: 14: sequence of an amino acid encoded by the trpA gene
SEQ ID NO: 15: nucleotide sequence of the trpB gene
SEQ ID NO: 16: sequence of an amino acid encoded by the trpB gene
SEQ ID NO: 17: primer for amplifying evgAS operon
SEQ ID NO: 18: primer for amplifying evgAS operon
SEQ ID NO: 19: primer for amplifying gadE gene
SEQ ID NO: 20: primer for amplifying gadE gene
SEQ ID NO: 21: primer for amplifying ydeO gene
SEQ ID NO: 22: primer for amplifying ydeO gene
SEQ ID NO: 23: nucleotide sequence of the evgA gene
SEQ ID NO: 24: amino acid sequence of EvgA
SEQ ID NO: 25: nucleotide sequence of the evgS gene
SEQ ID NO: 26: amino acid sequence of EvgS
SEQ ID NO: 27: nucleotide sequence of the gadE gene
SEQ ID NO: 28: amino acid sequence of GadE
SEQ ID NO: 29: nucleotide sequence of the ydeO gene
SEQ ID NO: 30: amino acid sequence of YdeO
SEQ ID NO: 31: nucleotide sequence of the cadA gene
SEQ ID NO: 32: sequence of an amino acid encoded by the cadA gene
SEQ ID NO: 33: nucleotide sequence of the ldcC gene
SEQ ID NO: 34: sequence of an amino acid encoded by the ldcC gene
SEQ ID NO: 35: PCR primer for disrupting the cadA gene
SEQ ID NO: 36: PCR primer for disrupting the cadA gene
SEQ ID NO: 37: PCR primer for disrupting the ldc gene
SEQ ID NO: 38: PCR primer for disrupting the ldc gene While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an L-amino acid comprising:

A) culturing in a medium a bacterium of the family Enterobacteriaceae which has an ability to produce an L-amino acid and which has been modified to increase the expression of a gene selected from the group consisting of evgA, gadE, ydeO, and combinations thereof, B) producing and accumulating the L-amino acid in the medium, and C) collecting the L-amino acid from the medium, wherein expression of said gene(s) is/are increased by a method selected from the group consisting of:

a) increasing the copy number of said gene(s), b) modifying an expression regulatory sequence of said gene(s), c) modifying the bacterium so that the expression of an evgS gene that encodes a sensor kinase is increased by a method selected from the group consisting of:

i) increasing the copy number of the evgS gene, ii) modifying the expression regulatory sequence of the evgS gene, and iii) combinations thereof; and d) combinations thereof, and wherein said L-amino acid is selected from the group consisting of a basic amino acid, a hydroxymonoaminocarboxylic acid, and an aromatic amino acid, wherein the basic amino acid is selected from the group consisting of L-lysine, L-ornithine, L-arginine, L-histidine, and L-citrulline;

wherein the hydroxymonoaminocarboxylic acid is selected from the group consisting of L-threonine and L-serine; and wherein the aromatic amino acid is selected from the group consisting of L-tryptophan, L-phenylalanine, and L-tyrosine.

2. The method according to claim 1, wherein the evgA gene is selected from the group consisting of:

(a) a DNA comprising the nucleotide sequence of SEQ ID NO: 23, and (b) a DNA which hybridizes with:

i) a nucleotide sequence complementary to the nucleotide sequence of SEQ ID NO: 23, or ii) a probe prepared from the nucleotide sequence in i) under stringent conditions, and which encodes a protein having transcription factor activity.

3. The method according to claim 1, wherein the gadE gene is selected from the group consisting of:

(a) a DNA comprising the nucleotide sequence of SEQ ID NO: 27, and (b) a DNA which hybridizes with:

i) a nucleotide sequence complementary to the nucleotide sequence of SEQ ID NO: 27 or ii) a probe prepared from the nucleotide sequence in i) under stringent conditions, and which encodes a protein having transcription factor activity.

4. The method according to claim 1, wherein the ydeO gene is selected from the group consisting of:

(a) a DNA comprising the nucleotide sequence of SEQ ID NO: 29, and (b) a DNA which hybridizes with:

i) a nucleotide sequence complementary to the nucleotide sequence of SEQ ID NO: 29 or ii) a probe prepared from the nucleotide sequence in i) under stringent conditions, and which encodes a protein having transcription factor activity.

5. The method according to claim 1, wherein the evgS gene is selected from the group consisting of:

(a) a DNA comprising the nucleotide sequence of SEQ ID NO: 25, and (b) a DNA which hybridizes with:

i) a nucleotide sequence complementary to the nucleotide sequence of SEQ ID NO: 25, or ii) a probe prepared from the nucleotide sequence in i) under stringent conditions, and which encodes a protein having phosphotransfer activity.

6. The method according to claim 1, wherein the evgA gene encodes a protein selected from the group consisting of:

(a) a protein comprising the amino acid sequence of SEQ ID NO: 24, and (b) a protein comprising the amino acid sequence of SEQ ID NO: 24, but which includes one or more amino acid substitutions, deletions, insertions, additions, or inversions and has transcription factor activity.

7. The method according to claim 1, wherein the gadE gene encodes a protein selected from the group consisting of:

(a) a protein comprising the amino acid sequence of SEQ ID NO: 28, and (b) a protein comprising the amino acid sequence of SEQ ID NO: 28, but which includes one or more amino acid substitutions, deletions, insertions, additions, or inversions and has transcription factor activity.

8. The method according to claim 1, wherein the ydeO gene encodes a protein selected from the group consisting of:

(a) a protein comprising the amino acid sequence of SEQ ID NO: 30, (b) a protein comprising the amino acid sequence of SEQ ID NO: 30, but which includes one or more amino acid substitutions, deletions, insertions, additions, or inversions and has transcription factor activity.

9. The method according to claim 1, wherein the evgS gene encodes a protein selected from the group consisting of:
   (a) a protein comprising the amino acid sequence of SEQ ID NO: 26,
   (b) a protein comprising the amino acid sequence of SEQ ID NO: 26, but which includes one or more substitutions, deletions, insertions, additions, or inversions and has phosphotransfer activity.

10. The method according to claim 1 wherein the bacterium is a member of the genera selected from the group consisting of *Escherichia, Enterobacter, Pantoea, Klebsiella*, and *Serratia*.

11. The method according to claim 1 wherein the L-amino acid is selected from the group consisting of L-lysine, L-threonine, L-tryptophan, and combinations thereof.

* * * * *

SEQUENCE LISTING

```
<160> NUMBER OF SEQ ID NOS: 38

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
```

```
gggttaattg tttttctgcg                                               20
```

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2

```
cgcatctcga ctgcacggtg                                               20
```

<210> SEQ ID NO 3
<211> LENGTH: 27
<212> TYPE: DNA
<213> ORGANISM: Artificial
<220> FEATURE:
<223> OTHER INFORMATION: primer

<400> SEQUENCE: 3

```
gccgaattca agtgtgtgaa gtgtatg                                       27
```

<210> SEQ ID NO 4
<211> LENGTH: 27
<212> TYPE: DNA
<213> ORGANISM: Artificial
<220> FEATURE:
<223> OTHER INFORMATION: primer

<400> SEQUENCE: 4

```
gccaagcttc cgacacgctc aacccag                                       27
```

<210> SEQ ID NO 5
<211> LENGTH: 864
<212> TYPE: DNA
<213> ORGANISM: Escherichia coli
<220> FEATURE:
<221> NAME/KEY: CDS
<222> LOCATION: (1)..(864)

<400> SEQUENCE: 5

```
atg aaa atg att tcc acg ata cag aaa aaa gag act gtc atg gtc gca    48
Met Lys Met Ile Ser Thr Ile Gln Lys Lys Glu Thr Val Met Val Ala
1               5                   10                  15 ccc att ccc gcg aaa cgc ggc aga aaa ccc gcc gtt gcc acc gca cca    96
Pro Ile Pro Ala Lys Arg Gly Arg Lys Pro Ala Val Ala Thr Ala Pro
                20                  25                  30 gcg act gga cag gtt cag tct tta acg cgt ggc ctg aaa tta ctg gag   144
Ala Thr Gly Gln Val Gln Ser Leu Thr Arg Gly Leu Lys Leu Leu Glu
            35                  40                  45 tgg att gcc gaa tcc aat ggc agt gtg gca ctc acg gaa ctg gcg caa   192
Trp Ile Ala Glu Ser Asn Gly Ser Val Ala Leu Thr Glu Leu Ala Gln
        50                  55                  60 caa gcc ggg tta ccc aat tcc acg acc cac cgc ctg cta acc acg atg   240
Gln Ala Gly Leu Pro Asn Ser Thr Thr His Arg Leu Leu Thr Thr Met
65                  70                  75                  80 caa cag cag ggt ttc gtg cgt cag gtt ggc gaa ctg gga cat tgg gca   288
Gln Gln Gln Gly Phe Val Arg Gln Val Gly Glu Leu Gly His Trp Ala
                85                  90                  95 atc ggc gca cat gcc ttt atg gtc ggc agc agc ttt ctc cag agc cgt   336
Ile Gly Ala His Ala Phe Met Val Gly Ser Ser Phe Leu Gln Ser Arg
                100                 105                 110 aat ttg tta gcg att gtt cac cct atc ctg cgc aat cta atg gaa gag   384
Asn Leu Leu Ala Ile Val His Pro Ile Leu Arg Asn Leu Met Glu Glu
```

```
tct ggc gaa acg gtc aat atg gcg gtg ctt gat caa agc gat cac gaa    432
Ser Gly Glu Thr Val Asn Met Ala Val Leu Asp Gln Ser Asp His Glu
    130                 135                 140 gcg att att atc gac cag gta cag tgt acg cat ctg atg cga atg tcc    480
Ala Ile Ile Ile Asp Gln Val Gln Cys Thr His Leu Met Arg Met Ser
145                 150                 155                 160 gcg cct atc ggc ggt aaa ttg ccg atg cac gct tcc ggt gcg ggt aaa    528
Ala Pro Ile Gly Gly Lys Leu Pro Met His Ala Ser Gly Ala Gly Lys
                165                 170                 175 gcc ttt tta gcc caa ctg agc gaa gaa cag gtg acg aag ctg ctg cac    576
Ala Phe Leu Ala Gln Leu Ser Glu Glu Gln Val Thr Lys Leu Leu His
            180                 185                 190 cgc aaa ggg tta cat gcc tat acc cac gca acg ctg gtg tct cct gtg    624
Arg Lys Gly Leu His Ala Tyr Thr His Ala Thr Leu Val Ser Pro Val
        195                 200                 205 cat tta aaa gaa gat ctc gcc caa acg cgc aaa cgg ggt tat tca ttt    672
His Leu Lys Glu Asp Leu Ala Gln Thr Arg Lys Arg Gly Tyr Ser Phe
    210                 215                 220 gac gat gag gaa cat gca ctg ggg cta cgt tgc ctt gca gcg tgt att    720
Asp Asp Glu Glu His Ala Leu Gly Leu Arg Cys Leu Ala Ala Cys Ile
225                 230                 235                 240 ttc gat gag cac cgt gaa ccg ttt gcc gca att tct att tcc gga ccg    768
Phe Asp Glu His Arg Glu Pro Phe Ala Ala Ile Ser Ile Ser Gly Pro
                245                 250                 255 att tca cgt att acc gat gac cgc gtg acc gag ttt ggc gcg atg gtg    816
Ile Ser Arg Ile Thr Asp Asp Arg Val Thr Glu Phe Gly Ala Met Val
            260                 265                 270 att aaa gcg gcg aag gaa gtg acg ctg gcg tac ggt gga atg cgc tga    864
Ile Lys Ala Ala Lys Glu Val Thr Leu Ala Tyr Gly Gly Met Arg
        275                 280                 285
```

<210> SEQ ID NO 6
<211> LENGTH: 287
<212> TYPE: PRT
<213> ORGANISM: Escherichia coli

<400> SEQUENCE: 6

```
Met Lys Met Ile Ser Thr Ile Gln Lys Lys Glu Thr Val Met Val Ala
1               5                   10                  15

Pro Ile Pro Ala Lys Arg Gly Arg Lys Pro Ala Val Ala Thr Ala Pro
            20                  25                  30

Ala Thr Gly Gln Val Gln Ser Leu Thr Arg Gly Leu Lys Leu Leu Glu
        35                  40                  45

Trp Ile Ala Glu Ser Asn Gly Ser Val Ala Leu Thr Glu Leu Ala Gln
    50                  55                  60

Gln Ala Gly Leu Pro Asn Ser Thr Thr His Arg Leu Leu Thr Thr Met
65                  70                  75                  80

Gln Gln Gln Gly Phe Val Arg Gln Val Gly Glu Leu Gly His Trp Ala
                85                  90                  95

Ile Gly Ala His Ala Phe Met Val Gly Ser Ser Phe Leu Gln Ser Arg
            100                 105                 110

Asn Leu Leu Ala Ile Val His Pro Ile Leu Arg Asn Leu Met Glu Glu
        115                 120                 125

Ser Gly Glu Thr Val Asn Met Ala Val Leu Asp Gln Ser Asp His Glu
    130                 135                 140

Ala Ile Ile Ile Asp Gln Val Gln Cys Thr His Leu Met Arg Met Ser
145                 150                 155                 160
```

```
Ala Pro Ile Gly Gly Lys Leu Pro Met His Ala Ser Gly Ala Gly Lys
            165                 170                 175

Ala Phe Leu Ala Gln Leu Ser Glu Glu Gln Val Thr Lys Leu Leu His
        180                 185                 190

Arg Lys Gly Leu His Ala Tyr Thr His Ala Thr Leu Val Ser Pro Val
            195                 200                 205

His Leu Lys Glu Asp Leu Ala Gln Thr Arg Lys Arg Gly Tyr Ser Phe
        210                 215                 220

Asp Asp Glu Glu His Ala Leu Gly Leu Arg Cys Leu Ala Ala Cys Ile
225                 230                 235                 240

Phe Asp Glu His Arg Glu Pro Phe Ala Ala Ile Ser Ile Ser Gly Pro
                245                 250                 255

Ile Ser Arg Ile Thr Asp Asp Arg Val Thr Glu Phe Gly Ala Met Val
            260                 265                 270

Ile Lys Ala Ala Lys Glu Val Thr Leu Ala Tyr Gly Gly Met Arg
        275                 280                 285

<210> SEQ ID NO 7
<211> LENGTH: 1305
<212> TYPE: DNA
<213> ORGANISM: Escherichia coli
<220> FEATURE:
<221> NAME/KEY: CDS
<222> LOCATION: (1)..(1305)

<400> SEQUENCE: 7 atg aaa acc cgt aca caa caa att gaa gaa tta cag aaa gag tgg act      48
Met Lys Thr Arg Thr Gln Gln Ile Glu Glu Leu Gln Lys Glu Trp Thr
1               5                   10                  15 caa ccg cgt tgg gaa ggc att act cgc cca tac agt gcg gaa gat gtg     96
Gln Pro Arg Trp Glu Gly Ile Thr Arg Pro Tyr Ser Ala Glu Asp Val
            20                  25                  30 gtg aaa tta cgc ggt tca gtc aat cct gaa tgc acg ctg gcg caa ctg    144
Val Lys Leu Arg Gly Ser Val Asn Pro Glu Cys Thr Leu Ala Gln Leu
        35                  40                  45 ggc gca gcg aaa atg tgg cgt ctg ctg cac ggt gag tcg aaa aaa ggc    192
Gly Ala Ala Lys Met Trp Arg Leu Leu His Gly Glu Ser Lys Lys Gly
    50                  55                  60 tac atc aac agc ctc ggc gca ctg act ggc ggt cag gcg ctg caa cag    240
Tyr Ile Asn Ser Leu Gly Ala Leu Thr Gly Gly Gln Ala Leu Gln Gln
65                  70                  75                  80 gcg aaa gcg ggt att gaa gca gtc tat ctg tcg gga tgg cag gta gcg    288
Ala Lys Ala Gly Ile Glu Ala Val Tyr Leu Ser Gly Trp Gln Val Ala
                85                  90                  95 gcg gac gct aac ctg gcg gcc agc atg tat ccg gat cag tcg ctc tat    336
Ala Asp Ala Asn Leu Ala Ala Ser Met Tyr Pro Asp Gln Ser Leu Tyr
            100                 105                 110 ccg gca aac tcg gtg cca gct gtg gtg gag cgg atc aac aac acc ttc    384
Pro Ala Asn Ser Val Pro Ala Val Val Glu Arg Ile Asn Asn Thr Phe
        115                 120                 125 cgt cgt gcc gat cag atc caa tgg tcc gcg ggc att gag ccg ggc gat    432
Arg Arg Ala Asp Gln Ile Gln Trp Ser Ala Gly Ile Glu Pro Gly Asp
    130                 135                 140 ccg cgc tat gtc gat tac ttc ctg ccg atc gtt gcc gat gcg gaa gcc    480
Pro Arg Tyr Val Asp Tyr Phe Leu Pro Ile Val Ala Asp Ala Glu Ala
145                 150                 155                 160 ggt ttt ggc ggt gtc ctg aat gcc ttt gaa ctg atg aaa gcg atg att    528
Gly Phe Gly Gly Val Leu Asn Ala Phe Glu Leu Met Lys Ala Met Ile
                165                 170                 175
```

```
gaa gcc ggt gca gcg gca gtt cac ttc gaa gat cag ctg gcg tca gtg      576
Glu Ala Gly Ala Ala Ala Val His Phe Glu Asp Gln Leu Ala Ser Val
            180                 185                 190 aag aaa tgc ggt cac atg ggc ggc aaa gtt tta gtg cca act cag gaa      624
Lys Lys Cys Gly His Met Gly Gly Lys Val Leu Val Pro Thr Gln Glu
        195                 200                 205 gct att cag aaa ctg gtc gcg gcg cgt ctg gca gct gac gtg acg ggc      672
Ala Ile Gln Lys Leu Val Ala Ala Arg Leu Ala Ala Asp Val Thr Gly
    210                 215                 220 gtt cca acc ctg ctg gtt gcc cgt acc gat gct gat gcg gcg gat ctg      720
Val Pro Thr Leu Leu Val Ala Arg Thr Asp Ala Asp Ala Ala Asp Leu
225                 230                 235                 240 atc acc tcc gat tgc gac ccg tat gac agc gaa ttt att acc ggc gag      768
Ile Thr Ser Asp Cys Asp Pro Tyr Asp Ser Glu Phe Ile Thr Gly Glu
                245                 250                 255 cgt acc agt gaa ggc ttc ttc cgt act cat gcg ggc att gag caa gcg      816
Arg Thr Ser Glu Gly Phe Phe Arg Thr His Ala Gly Ile Glu Gln Ala
            260                 265                 270 atc agc cgt ggc ctg gcg tat gcg cca tat gct gac ctg gtc tgg tgt      864
Ile Ser Arg Gly Leu Ala Tyr Ala Pro Tyr Ala Asp Leu Val Trp Cys
        275                 280                 285 gaa acc tcc acg ccg gat ctg gaa ctg gcg cgt cgc ttt gca caa gct      912
Glu Thr Ser Thr Pro Asp Leu Glu Leu Ala Arg Arg Phe Ala Gln Ala
    290                 295                 300 atc cac gcg aaa tat ccg ggc aaa ctg ctg gct tat aac tgc tcg ccg      960
Ile His Ala Lys Tyr Pro Gly Lys Leu Leu Ala Tyr Asn Cys Ser Pro
305                 310                 315                 320 tcg ttc aac tgg cag aaa aac ctc gac gac aaa act att gcc agc ttc     1008
Ser Phe Asn Trp Gln Lys Asn Leu Asp Asp Lys Thr Ile Ala Ser Phe
                325                 330                 335 cag cag cag ctg tcg gat atg ggc tac aag ttc cag ttc atc acc ctg     1056
Gln Gln Gln Leu Ser Asp Met Gly Tyr Lys Phe Gln Phe Ile Thr Leu
            340                 345                 350 gca ggt atc cac agc atg tgg ttc aac atg ttt gac ctg gca aac gcc     1104
Ala Gly Ile His Ser Met Trp Phe Asn Met Phe Asp Leu Ala Asn Ala
        355                 360                 365 tat gcc cag ggc gag ggt atg aag cac tac gtt gag aaa gtg cag cag     1152
Tyr Ala Gln Gly Glu Gly Met Lys His Tyr Val Glu Lys Val Gln Gln
    370                 375                 380 ccg gaa ttt gcc gcc gcg aaa gat ggc tat acc ttc gta tct cac cag     1200
Pro Glu Phe Ala Ala Ala Lys Asp Gly Tyr Thr Phe Val Ser His Gln
385                 390                 395                 400 cag gaa gtg ggt aca ggt tac ttc gat aaa gtg acg act att att cag     1248
Gln Glu Val Gly Thr Gly Tyr Phe Asp Lys Val Thr Thr Ile Ile Gln
                405                 410                 415 ggc ggc acg tct tca gtc acc gcg ctg acc ggc tcc act gaa gaa tcg     1296
Gly Gly Thr Ser Ser Val Thr Ala Leu Thr Gly Ser Thr Glu Glu Ser
            420                 425                 430 cag ttc taa                                                          1305
Gln Phe <210> SEQ ID NO 8
<211> LENGTH: 434
<212> TYPE: PRT
<213> ORGANISM: Escherichia coli

<400> SEQUENCE: 8

Met Lys Thr Arg Thr Gln Gln Ile Glu Glu Leu Gln Lys Glu Trp Thr
1               5                   10                  15
```

-continued

```
Gln Pro Arg Trp Glu Gly Ile Thr Arg Pro Tyr Ser Ala Glu Asp Val
             20                  25                  30

Val Lys Leu Arg Gly Ser Val Asn Pro Glu Cys Thr Leu Ala Gln Leu
         35                  40                  45

Gly Ala Ala Lys Met Trp Arg Leu Leu His Gly Glu Ser Lys Lys Gly
     50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                 85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380

Pro Glu Phe Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe
```

<210> SEQ ID NO 9
<211> LENGTH: 1602
<212> TYPE: DNA
<213> ORGANISM: Escherichia coli
<220> FEATURE:
<221> NAME/KEY: CDS
<222> LOCATION: (1)..(1602)

<400> SEQUENCE: 9

| | | | | | | | | | | | | | | | | |
|---|---|---|---|---|---|---|---|---|---|---|---|---|---|---|---|---|
| atg | act | gaa | cag | gca | aca | aca | acc | gat | gaa | ctg | gct | ttc | aca | agg | ccg | 48 |
| Met | Thr | Glu | Gln | Ala | Thr | Thr | Thr | Asp | Glu | Leu | Ala | Phe | Thr | Arg | Pro | |
| 1 | | | | 5 | | | | | 10 | | | | | 15 | | |
| tat | ggc | gag | cag | gag | aag | caa | att | ctt | act | gcc | gaa | gcg | gta | gaa | ttt | 96 |
| Tyr | Gly | Glu | Gln | Glu | Lys | Gln | Ile | Leu | Thr | Ala | Glu | Ala | Val | Glu | Phe | |
| | | | 20 | | | | | 25 | | | | | 30 | | | |
| ctg | act | gag | ctg | gtg | acg | cat | ttt | acg | cca | caa | cgc | aat | aaa | ctt | ctg | 144 |
| Leu | Thr | Glu | Leu | Val | Thr | His | Phe | Thr | Pro | Gln | Arg | Asn | Lys | Leu | Leu | |
| | 35 | | | | | 40 | | | | | 45 | | | | | |
| gca | gcg | cgc | att | cag | cag | cag | caa | gat | att | gat | aac | gga | acg | ttg | cct | 192 |
| Ala | Ala | Arg | Ile | Gln | Gln | Gln | Gln | Asp | Ile | Asp | Asn | Gly | Thr | Leu | Pro | |
| 50 | | | | | 55 | | | | | 60 | | | | | | |
| gat | ttt | att | tcg | gaa | aca | gct | tcc | att | cgc | gat | gct | gat | tgg | aaa | att | 240 |
| Asp | Phe | Ile | Ser | Glu | Thr | Ala | Ser | Ile | Arg | Asp | Ala | Asp | Trp | Lys | Ile | |
| 65 | | | | | 70 | | | | | 75 | | | | | 80 | |
| cgc | ggg | att | cct | gcg | gac | tta | gaa | gac | cgc | cgc | gta | gag | ata | act | ggc | 288 |
| Arg | Gly | Ile | Pro | Ala | Asp | Leu | Glu | Asp | Arg | Arg | Val | Glu | Ile | Thr | Gly | |
| | | | | 85 | | | | | 90 | | | | | 95 | | |
| ccg | gta | gag | cgc | aag | atg | gtg | atc | aac | gcg | ctc | aac | gcc | aat | gtg | aaa | 336 |
| Pro | Val | Glu | Arg | Lys | Met | Val | Ile | Asn | Ala | Leu | Asn | Ala | Asn | Val | Lys | |
| | | | 100 | | | | | 105 | | | | | 110 | | | |
| gtc | ttt | atg | gcc | gat | ttc | gaa | gat | tca | ctg | gca | cca | gac | tgg | aac | aaa | 384 |
| Val | Phe | Met | Ala | Asp | Phe | Glu | Asp | Ser | Leu | Ala | Pro | Asp | Trp | Asn | Lys | |
| | | 115 | | | | | 120 | | | | | 125 | | | | |
| gtg | atc | gac | ggg | caa | att | aac | ctg | cgt | gat | gcg | gtt | aac | ggc | acc | atc | 432 |
| Val | Ile | Asp | Gly | Gln | Ile | Asn | Leu | Arg | Asp | Ala | Val | Asn | Gly | Thr | Ile | |
| | 130 | | | | | 135 | | | | | 140 | | | | | |
| agt | tac | acc | aat | gaa | gca | ggc | aaa | att | tac | cag | ctc | aag | ccc | aat | cca | 480 |
| Ser | Tyr | Thr | Asn | Glu | Ala | Gly | Lys | Ile | Tyr | Gln | Leu | Lys | Pro | Asn | Pro | |
| 145 | | | | | 150 | | | | | 155 | | | | | 160 | |
| gcg | gtt | ttg | att | tgt | cgg | gta | cgc | ggt | ctg | cac | ttg | ccg | gaa | aaa | cat | 528 |
| Ala | Val | Leu | Ile | Cys | Arg | Val | Arg | Gly | Leu | His | Leu | Pro | Glu | Lys | His | |
| | | | | 165 | | | | | 170 | | | | | 175 | | |
| gtc | acc | tgg | cgt | ggt | gag | gca | atc | ccc | ggc | agc | ctg | ttt | gat | ttt | gcg | 576 |
| Val | Thr | Trp | Arg | Gly | Glu | Ala | Ile | Pro | Gly | Ser | Leu | Phe | Asp | Phe | Ala | |
| | | | 180 | | | | | 185 | | | | | 190 | | | |
| ctc | tat | ttc | ttc | cac | aac | tat | cag | gca | ctg | ttg | gca | aag | ggc | agt | ggt | 624 |
| Leu | Tyr | Phe | Phe | His | Asn | Tyr | Gln | Ala | Leu | Leu | Ala | Lys | Gly | Ser | Gly | |
| | 195 | | | | | 200 | | | | | 205 | | | | | |
| ccc | tat | ttc | tat | ctg | ccg | aaa | acc | cag | tcc | tgg | cag | gaa | gcg | gcc | tgg | 672 |
| Pro | Tyr | Phe | Tyr | Leu | Pro | Lys | Thr | Gln | Ser | Trp | Gln | Glu | Ala | Ala | Trp | |
| 210 | | | | | 215 | | | | | 220 | | | | | | |
| tgg | agc | gaa | gtc | ttc | agc | tat | gca | gaa | gat | cgc | ttt | aat | ctg | ccg | cgc | 720 |
| Trp | Ser | Glu | Val | Phe | Ser | Tyr | Ala | Glu | Asp | Arg | Phe | Asn | Leu | Pro | Arg | |
| 225 | | | | | 230 | | | | | 235 | | | | | 240 | |
| ggc | acc | atc | aag | gcg | acg | ttg | ctg | att | gaa | acg | ctg | ccc | gcc | gtg | ttc | 768 |
| Gly | Thr | Ile | Lys | Ala | Thr | Leu | Leu | Ile | Glu | Thr | Leu | Pro | Ala | Val | Phe | |
| | | | | 245 | | | | | 250 | | | | | 255 | | |
| cag | atg | gat | gaa | atc | ctt | cac | gcg | ctg | cgt | gac | cat | att | gtt | ggt | ctg | 816 |
| Gln | Met | Asp | Glu | Ile | Leu | His | Ala | Leu | Arg | Asp | His | Ile | Val | Gly | Leu | |
| | | | | | 260 | | | | | 265 | | | | | 270 | |

```
aac tgc ggt cgt tgg gat tac atc ttc agc tat atc aaa acg ttg aaa      864
Asn Cys Gly Arg Trp Asp Tyr Ile Phe Ser Tyr Ile Lys Thr Leu Lys
            275                 280                 285 aac tat ccc gat cgc gtc ctg cca gac aga cag gca gtg acg atg gat      912
Asn Tyr Pro Asp Arg Val Leu Pro Asp Arg Gln Ala Val Thr Met Asp
        290                 295                 300 aaa cca ttc ctg aat gct tac tca cgc ctg ttg att aaa acc tgc cat      960
Lys Pro Phe Leu Asn Ala Tyr Ser Arg Leu Leu Ile Lys Thr Cys His
305                 310                 315                 320 aaa cgc ggt gct ttt gcg atg ggc ggc atg gcg gcg ttt att ccg agc     1008
Lys Arg Gly Ala Phe Ala Met Gly Gly Met Ala Ala Phe Ile Pro Ser
                325                 330                 335 aaa gat gaa gag cac aat aac cag gtg ctc aac aaa gta aaa gcg gat     1056
Lys Asp Glu Glu His Asn Asn Gln Val Leu Asn Lys Val Lys Ala Asp
            340                 345                 350 aaa tcg ctg gaa gcc aat aac ggt cac gat ggc aca tgg atc gct cac     1104
Lys Ser Leu Glu Ala Asn Asn Gly His Asp Gly Thr Trp Ile Ala His
        355                 360                 365 cca ggc ctt gcg gac acg gca atg gcg gta ttc aac gac att ctc ggc     1152
Pro Gly Leu Ala Asp Thr Ala Met Ala Val Phe Asn Asp Ile Leu Gly
370                 375                 380 tcc cgt aaa aat cag ctt gaa gtg atg cgc gaa caa gac gcg ccg att     1200
Ser Arg Lys Asn Gln Leu Glu Val Met Arg Glu Gln Asp Ala Pro Ile
385                 390                 395                 400 act gcc gat cag ctg ctg gca cct tgt gat ggt gaa cgc acc gaa gaa     1248
Thr Ala Asp Gln Leu Leu Ala Pro Cys Asp Gly Glu Arg Thr Glu Glu
                405                 410                 415 ggt atg cgc gcc aac att cgc gtg gct gtg cag tac atc gaa gcg tgg     1296
Gly Met Arg Ala Asn Ile Arg Val Ala Val Gln Tyr Ile Glu Ala Trp
            420                 425                 430 atc tct ggc aac ggc tgt gtg ccg att tat ggc ctg atg gaa gat gcg     1344
Ile Ser Gly Asn Gly Cys Val Pro Ile Tyr Gly Leu Met Glu Asp Ala
        435                 440                 445 gcg acg gct gaa att tcc cgt acc tcg atc tgg cag tgg atc cat cat     1392
Ala Thr Ala Glu Ile Ser Arg Thr Ser Ile Trp Gln Trp Ile His His
450                 455                 460 caa aaa acg ttg agc aat ggc aaa ccg gtg acc aaa gcc ttg ttc cgc     1440
Gln Lys Thr Leu Ser Asn Gly Lys Pro Val Thr Lys Ala Leu Phe Arg
465                 470                 475                 480 cag atg ctg ggc gaa gag atg aaa gtc att gcc agc gaa ctg ggc gaa     1488
Gln Met Leu Gly Glu Glu Met Lys Val Ile Ala Ser Glu Leu Gly Glu
                485                 490                 495 gaa cgt ttc tcc cag ggg cgt ttt gac gat gcc gca cgc ttg atg gaa     1536
Glu Arg Phe Ser Gln Gly Arg Phe Asp Asp Ala Ala Arg Leu Met Glu
            500                 505                 510 cag atc acc act tcc gat gag tta att gat ttc ctg acc ctg cca ggc     1584
Gln Ile Thr Thr Ser Asp Glu Leu Ile Asp Phe Leu Thr Leu Pro Gly
        515                 520                 525 tac cgc ctg tta gcg taa                                              1602
Tyr Arg Leu Leu Ala
    530

<210> SEQ ID NO 10
<211> LENGTH: 533
<212> TYPE: PRT
<213> ORGANISM: Escherichia coli

<400> SEQUENCE: 10

Met Thr Glu Gln Ala Thr Thr Thr Asp Glu Leu Ala Phe Thr Arg Pro
1               5                   10                  15
```

```
Tyr Gly Glu Gln Glu Lys Gln Ile Leu Thr Ala Glu Ala Val Glu Phe
             20                  25                  30
Leu Thr Glu Leu Val Thr His Phe Thr Pro Gln Arg Asn Lys Leu Leu
         35                  40                  45
Ala Ala Arg Ile Gln Gln Gln Asp Ile Asp Asn Gly Thr Leu Pro
 50                  55                  60
Asp Phe Ile Ser Glu Thr Ala Ser Ile Arg Asp Ala Asp Trp Lys Ile
 65                  70                  75                  80
Arg Gly Ile Pro Ala Asp Leu Glu Asp Arg Val Glu Ile Thr Gly
                 85                  90                  95
Pro Val Glu Arg Lys Met Val Ile Asn Ala Leu Asn Ala Asn Val Lys
                100                 105                 110
Val Phe Met Ala Asp Phe Glu Asp Ser Leu Ala Pro Asp Trp Asn Lys
         115                 120                 125
Val Ile Asp Gly Gln Ile Asn Leu Arg Asp Ala Val Asn Gly Thr Ile
130                 135                 140
Ser Tyr Thr Asn Glu Ala Gly Lys Ile Tyr Gln Leu Lys Pro Asn Pro
145                 150                 155                 160
Ala Val Leu Ile Cys Arg Val Arg Gly Leu His Leu Pro Glu Lys His
                165                 170                 175
Val Thr Trp Arg Gly Glu Ala Ile Pro Gly Ser Leu Phe Asp Phe Ala
             180                 185                 190
Leu Tyr Phe Phe His Asn Tyr Gln Ala Leu Leu Ala Lys Gly Ser Gly
         195                 200                 205
Pro Tyr Phe Tyr Leu Pro Lys Thr Gln Ser Trp Gln Glu Ala Ala Trp
             210                 215                 220
Trp Ser Glu Val Phe Ser Tyr Ala Glu Asp Arg Phe Asn Leu Pro Arg
225                 230                 235                 240
Gly Thr Ile Lys Ala Thr Leu Leu Ile Glu Thr Leu Pro Ala Val Phe
                245                 250                 255
Gln Met Asp Glu Ile Leu His Ala Leu Arg Asp His Ile Val Gly Leu
             260                 265                 270
Asn Cys Gly Arg Trp Asp Tyr Ile Phe Ser Tyr Ile Lys Thr Leu Lys
         275                 280                 285
Asn Tyr Pro Asp Arg Val Leu Pro Asp Arg Gln Ala Val Thr Met Asp
         290                 295                 300
Lys Pro Phe Leu Asn Ala Tyr Ser Arg Leu Leu Ile Lys Thr Cys His
305                 310                 315                 320
Lys Arg Gly Ala Phe Ala Met Gly Gly Met Ala Ala Phe Ile Pro Ser
                325                 330                 335
Lys Asp Glu Glu His Asn Asn Gln Val Leu Asn Lys Val Lys Ala Asp
             340                 345                 350
Lys Ser Leu Glu Ala Asn Asn Gly His Asp Gly Thr Trp Ile Ala His
         355                 360                 365
Pro Gly Leu Ala Asp Thr Ala Met Ala Val Phe Asn Asp Ile Leu Gly
         370                 375                 380
Ser Arg Lys Asn Gln Leu Glu Val Met Arg Glu Gln Asp Ala Pro Ile
385                 390                 395                 400
Thr Ala Asp Gln Leu Leu Ala Pro Cys Asp Gly Glu Arg Thr Glu Glu
                405                 410                 415
Gly Met Arg Ala Asn Ile Arg Val Ala Val Gln Tyr Ile Glu Ala Trp
             420                 425                 430
```

```
Ile Ser Gly Asn Gly Cys Val Pro Ile Tyr Gly Leu Met Glu Asp Ala
            435                 440                 445

Ala Thr Ala Glu Ile Ser Arg Thr Ser Ile Trp Gln Trp Ile His His
    450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510

Gln Ile Thr Thr Ser Asp Glu Leu Ile Asp Phe Leu Thr Leu Pro Gly
        515                 520                 525

Tyr Arg Leu Leu Ala
        530
```

<210> SEQ ID NO 11
<211> LENGTH: 1737
<212> TYPE: DNA
<213> ORGANISM: Escherichia coli
<220> FEATURE:
<221> NAME/KEY: CDS
<222> LOCATION: (1)..(1737)

<400> SEQUENCE: 11

```
atg ccg cgt ggc ctg gaa tta ttg att gct caa acc att ttg caa ggc       48
Met Pro Arg Gly Leu Glu Leu Leu Ile Ala Gln Thr Ile Leu Gln Gly
1               5                   10                  15 ttc gat gct cag tat ggt cga ttc ctc gaa gtg acc tcc ggt gcg cag       96
Phe Asp Ala Gln Tyr Gly Arg Phe Leu Glu Val Thr Ser Gly Ala Gln
                20                  25                  30 cag cgt ttc gaa cag gcc gac tgg cat gct gtc cag cag gcg atg aaa      144
Gln Arg Phe Glu Gln Ala Asp Trp His Ala Val Gln Gln Ala Met Lys
            35                  40                  45 aac cgt atc cat ctt tac gat cat cac gtt ggt ctg gtc gtg gag caa      192
Asn Arg Ile His Leu Tyr Asp His His Val Gly Leu Val Val Glu Gln
        50                  55                  60 ctg cgc tgc att act aac ggc caa agt acg gac gcg gca ttt tta cta      240
Leu Arg Cys Ile Thr Asn Gly Gln Ser Thr Asp Ala Ala Phe Leu Leu
65                  70                  75                  80 cgt gtt aaa gag cat tac acc cgg ctg ttg ccg gat tac ccg cgc ttc      288
Arg Val Lys Glu His Tyr Thr Arg Leu Leu Pro Asp Tyr Pro Arg Phe
                85                  90                  95 gag att gcg gag agc ttt ttt aac tcc gtg tac tgt cgg tta ttt gac      336
Glu Ile Ala Glu Ser Phe Phe Asn Ser Val Tyr Cys Arg Leu Phe Asp
                100                 105                 110 cac cgc tcg ctt act ccc gag cgg ctt ttt atc ttt agc tct cag cca      384
His Arg Ser Leu Thr Pro Glu Arg Leu Phe Ile Phe Ser Ser Gln Pro
            115                 120                 125 gag cgc cgc ttt cgt acc att ccc cgc ccg ctg gcg aaa gac ttt cac      432
Glu Arg Arg Phe Arg Thr Ile Pro Arg Pro Leu Ala Lys Asp Phe His
        130                 135                 140 ccc gat cac ggc tgg gaa tct cta ctg atg cgc gtt atc agc gac cta      480
Pro Asp His Gly Trp Glu Ser Leu Leu Met Arg Val Ile Ser Asp Leu
145                 150                 155                 160 ccg ctg cgc ctg cgc tgg cag aat aaa agc cgt gac atc cat tac att      528
Pro Leu Arg Leu Arg Trp Gln Asn Lys Ser Arg Asp Ile His Tyr Ile
                165                 170                 175 att cgc cat ctg acg gaa acg ctg ggg aca gac aac ctc gcg gaa agt      576
Ile Arg His Leu Thr Glu Thr Leu Gly Thr Asp Asn Leu Ala Glu Ser
                180                 185                 190
```

-continued

| | | |
|---|---|---|
| cat tta cag gtg gcg aac gaa ctg ttt tac cgc aat aaa gcc gcc tgg<br>His Leu Gln Val Ala Asn Glu Leu Phe Tyr Arg Asn Lys Ala Ala Trp<br>        195                     200                   205 | | 624 |
| ctg gta ggc aaa ctg atc aca cct tcc ggc aca ttg cca ttt ttg ctg<br>Leu Val Gly Lys Leu Ile Thr Pro Ser Gly Thr Leu Pro Phe Leu Leu<br>        210                     215                   220 | | 672 |
| ccg atc cac cag acg gac gac ggc gag tta ttt att gat acc tgc ctg<br>Pro Ile His Gln Thr Asp Asp Gly Glu Leu Phe Ile Asp Thr Cys Leu<br>225                   230                   235                   240 | | 720 |
| acg acg acc gcc gaa gcg agc att gtt ttt ggc ttt gcg cgt tct tat<br>Thr Thr Thr Ala Glu Ala Ser Ile Val Phe Gly Phe Ala Arg Ser Tyr<br>                   245                   250                   255 | | 768 |
| ttt atg gtt tat gcg ccg ctg ccc gca gcg ctg gtc gag tgg cta cgg<br>Phe Met Val Tyr Ala Pro Leu Pro Ala Ala Leu Val Glu Trp Leu Arg<br>        260                     265                   270 | | 816 |
| gaa att ctg cca ggt aaa acc acc gct gaa ttg tat atg gct atc ggc<br>Glu Ile Leu Pro Gly Lys Thr Thr Ala Glu Leu Tyr Met Ala Ile Gly<br>                   275                   280                   285 | | 864 |
| tgc cag aag cac gcc aaa acc gaa agc tac cgc gaa tat ctc gtt tat<br>Cys Gln Lys His Ala Lys Thr Glu Ser Tyr Arg Glu Tyr Leu Val Tyr<br>        290                     295                   300 | | 912 |
| cta cag ggc tgt aat gag cag ttc att gaa gcg ccg ggt att cgt gga<br>Leu Gln Gly Cys Asn Glu Gln Phe Ile Glu Ala Pro Gly Ile Arg Gly<br>305                   310                   315                   320 | | 960 |
| atg gtg atg ttg gtg ttt acg ctg ccg ggc ttt gat cgg gta ttc aaa<br>Met Val Met Leu Val Phe Thr Leu Pro Gly Phe Asp Arg Val Phe Lys<br>                   325                   330                   335 | | 1008 |
| gtc atc aaa gac agg ttc gcg ccg cag aaa gag atg tct gcc gct cac<br>Val Ile Lys Asp Arg Phe Ala Pro Gln Lys Glu Met Ser Ala Ala His<br>        340                     345                   350 | | 1056 |
| gtt cgt gcc tgc tat caa ctg gtg aaa gag cac gat cgc gtg ggc cga<br>Val Arg Ala Cys Tyr Gln Leu Val Lys Glu His Asp Arg Val Gly Arg<br>                 355                   360                   365 | | 1104 |
| atg gcg gac acc cag gag ttt gaa aac ttt gtg ctg gag aag cgg cat<br>Met Ala Asp Thr Gln Glu Phe Glu Asn Phe Val Leu Glu Lys Arg His<br>        370                     375                   380 | | 1152 |
| att tcc ccg gca tta atg gaa tta ctg ctt cag gaa gca gcg gaa aaa<br>Ile Ser Pro Ala Leu Met Glu Leu Leu Leu Gln Glu Ala Ala Glu Lys<br>385                   390                   395                   400 | | 1200 |
| atc acc gat ctc ggc gaa caa att gtg att cgc cat ctt tat att gag<br>Ile Thr Asp Leu Gly Glu Gln Ile Val Ile Arg His Leu Tyr Ile Glu<br>                   405                   410                   415 | | 1248 |
| cgg cgg atg gtg ccg ctc aat atc tgg ctg gaa caa gtg gaa ggt cag<br>Arg Arg Met Val Pro Leu Asn Ile Trp Leu Glu Gln Val Glu Gly Gln<br>        420                     425                   430 | | 1296 |
| cag ttg cgc gac gcc att gaa gaa tac ggt aac gct att cgc cag ctt<br>Gln Leu Arg Asp Ala Ile Glu Glu Tyr Gly Asn Ala Ile Arg Gln Leu<br>                 435                   440                   445 | | 1344 |
| gcc gct gct aac att ttc cct ggc gac atg ctg ttt aaa aac ttc ggt<br>Ala Ala Ala Asn Ile Phe Pro Gly Asp Met Leu Phe Lys Asn Phe Gly<br>        450                     455                   460 | | 1392 |
| gtc acc cgt cac ggg cgt gtg gtt ttt tat gat tac gat gaa att tgc<br>Val Thr Arg His Gly Arg Val Val Phe Tyr Asp Tyr Asp Glu Ile Cys<br>465                   470                   475                   480 | | 1440 |
| tac atg acg gaa gtg aat ttc cgc gac atc ccg ccg cgc tat ccg<br>Tyr Met Thr Glu Val Asn Phe Arg Asp Ile Pro Pro Pro Arg Tyr Pro<br>                   485                   490                   495 | | 1488 |
| gaa gac gaa ctt gcc agc gaa ccg tgg tac agc gtc tcg ccg ggc gat<br>Glu Asp Glu Leu Ala Ser Glu Pro Trp Tyr Ser Val Ser Pro Gly Asp | | 1536 |

```
                500                 505                 510
gtt ttc ccg gaa gag ttt cgc cac tgg cta tgc gcc gac ccg cgt att      1584
Val Phe Pro Glu Glu Phe Arg His Trp Leu Cys Ala Asp Pro Arg Ile
        515                 520                 525 ggt ccg ctg ttt gaa gag atg cac gcc gac ctg ttc cgc gct gat tac      1632
Gly Pro Leu Phe Glu Glu Met His Ala Asp Leu Phe Arg Ala Asp Tyr
    530                 535                 540 tgg cgc gca cta caa aac cgc ata cgt gaa ggg cat gtg gaa gat gtt      1680
Trp Arg Ala Leu Gln Asn Arg Ile Arg Glu Gly His Val Glu Asp Val
545                 550                 555                 560 tat gcg tat cgg cgc agg caa aga ttt agc gta cgg tat ggg gag atg      1728
Tyr Ala Tyr Arg Arg Arg Gln Arg Phe Ser Val Arg Tyr Gly Glu Met
                565                 570                 575 ctt ttt tga                                                          1737
Leu Phe <210> SEQ ID NO 12
<211> LENGTH: 578
<212> TYPE: PRT
<213> ORGANISM: Escherichia coli

<400> SEQUENCE: 12

Met Pro Arg Gly Leu Glu Leu Ile Ala Gln Thr Ile Leu Gln Gly
1               5                   10                  15

Phe Asp Ala Gln Tyr Gly Arg Phe Leu Glu Val Thr Ser Gly Ala Gln
                20                  25                  30

Gln Arg Phe Glu Gln Ala Asp Trp His Ala Val Gln Gln Ala Met Lys
            35                  40                  45

Asn Arg Ile His Leu Tyr Asp His His Val Gly Leu Val Val Glu Gln
        50                  55                  60

Leu Arg Cys Ile Thr Asn Gly Gln Ser Thr Asp Ala Ala Phe Leu Leu
65                  70                  75                  80

Arg Val Lys Glu His Tyr Thr Arg Leu Leu Pro Asp Tyr Pro Arg Phe
                85                  90                  95

Glu Ile Ala Glu Ser Phe Phe Asn Ser Val Tyr Cys Arg Leu Phe Asp
                100                 105                 110

His Arg Ser Leu Thr Pro Glu Arg Leu Phe Ile Phe Ser Ser Gln Pro
            115                 120                 125

Glu Arg Arg Phe Arg Thr Ile Pro Arg Pro Leu Ala Lys Asp Phe His
        130                 135                 140

Pro Asp His Gly Trp Glu Ser Leu Leu Met Arg Val Ile Ser Asp Leu
145                 150                 155                 160

Pro Leu Arg Leu Arg Trp Gln Asn Lys Ser Arg Asp Ile His Tyr Ile
                165                 170                 175

Ile Arg His Leu Thr Glu Thr Leu Gly Thr Asp Asn Leu Ala Glu Ser
                180                 185                 190

His Leu Gln Val Ala Asn Glu Leu Phe Tyr Arg Asn Lys Ala Ala Trp
            195                 200                 205

Leu Val Gly Lys Leu Ile Thr Pro Ser Gly Thr Leu Pro Phe Leu Leu
        210                 215                 220

Pro Ile His Gln Thr Asp Asp Gly Glu Leu Phe Ile Asp Thr Cys Leu
225                 230                 235                 240

Thr Thr Thr Ala Glu Ala Ser Ile Val Phe Gly Phe Ala Arg Ser Tyr
                245                 250                 255

Phe Met Val Tyr Ala Pro Leu Pro Ala Ala Leu Val Glu Trp Leu Arg
                260                 265                 270
```

-continued

```
Glu Ile Leu Pro Gly Lys Thr Thr Ala Glu Leu Tyr Met Ala Ile Gly
        275                 280                 285

Cys Gln Lys His Ala Lys Thr Glu Ser Tyr Arg Glu Tyr Leu Val Tyr
290                 295                 300

Leu Gln Gly Cys Asn Glu Gln Phe Ile Glu Ala Pro Gly Ile Arg Gly
305                 310                 315                 320

Met Val Met Leu Val Phe Thr Leu Pro Gly Phe Asp Arg Val Phe Lys
                325                 330                 335

Val Ile Lys Asp Arg Phe Ala Pro Gln Lys Glu Met Ser Ala Ala His
                340                 345                 350

Val Arg Ala Cys Tyr Gln Leu Val Lys Glu His Asp Arg Val Gly Arg
            355                 360                 365

Met Ala Asp Thr Gln Glu Phe Glu Asn Phe Val Leu Glu Lys Arg His
370                 375                 380

Ile Ser Pro Ala Leu Met Glu Leu Leu Leu Gln Glu Ala Ala Glu Lys
385                 390                 395                 400

Ile Thr Asp Leu Gly Glu Gln Ile Val Ile Arg His Leu Tyr Ile Glu
                405                 410                 415

Arg Arg Met Val Pro Leu Asn Ile Trp Leu Glu Gln Val Glu Gly Gln
            420                 425                 430

Gln Leu Arg Asp Ala Ile Glu Glu Tyr Gly Asn Ala Ile Arg Gln Leu
        435                 440                 445

Ala Ala Ala Asn Ile Phe Pro Gly Asp Met Leu Phe Lys Asn Phe Gly
    450                 455                 460

Val Thr Arg His Gly Arg Val Val Phe Tyr Asp Tyr Asp Glu Ile Cys
465                 470                 475                 480

Tyr Met Thr Glu Val Asn Phe Arg Asp Ile Pro Pro Pro Arg Tyr Pro
                485                 490                 495

Glu Asp Glu Leu Ala Ser Glu Pro Trp Tyr Ser Val Ser Pro Gly Asp
            500                 505                 510

Val Phe Pro Glu Glu Phe Arg His Trp Leu Cys Ala Asp Pro Arg Ile
        515                 520                 525

Gly Pro Leu Phe Glu Glu Met His Ala Asp Leu Phe Arg Ala Asp Tyr
    530                 535                 540

Trp Arg Ala Leu Gln Asn Arg Ile Arg Glu Gly His Val Glu Asp Val
545                 550                 555                 560

Tyr Ala Tyr Arg Arg Arg Gln Arg Phe Ser Val Arg Tyr Gly Glu Met
                565                 570                 575

Leu Phe
```

```
<210> SEQ ID NO 13
<211> LENGTH: 807
<212> TYPE: DNA
<213> ORGANISM: Escherichia coli
<220> FEATURE:
<221> NAME/KEY: CDS
<222> LOCATION: (1)..(807)

<400> SEQUENCE: 13
```

```
atg gaa cgc tac gaa tct ctg ttt gcc cag ttg aag gag cgc aaa gaa    48
Met Glu Arg Tyr Glu Ser Leu Phe Ala Gln Leu Lys Glu Arg Lys Glu
1               5                   10                  15 ggc gca ttc gtt cct ttc gtc acg ctc ggt gat ccg ggc att gag cag    96
Gly Ala Phe Val Pro Phe Val Thr Leu Gly Asp Pro Gly Ile Glu Gln
            20                  25                  30
```

-continued

| | | |
|---|---|---|
| tca ttg aaa att atc gat acg cta att gaa gcc ggt gct gac gcg ctg<br>Ser Leu Lys Ile Ile Asp Thr Leu Ile Glu Ala Gly Ala Asp Ala Leu<br>35 40 45 | | 144 |
| gag tta ggc atc ccc ttc tcc gac cca ctg gcg gat ggc ccg acg att<br>Glu Leu Gly Ile Pro Phe Ser Asp Pro Leu Ala Asp Gly Pro Thr Ile<br>50 55 60 | | 192 |
| caa aac gcc act ctg cgc gcc ttt gcg gca ggt gtg act ccg gca caa<br>Gln Asn Ala Thr Leu Arg Ala Phe Ala Ala Gly Val Thr Pro Ala Gln<br>65 70 75 80 | | 240 |
| tgt ttt gaa atg ctg gca ctg att cgc cag aaa cac ccg acc att ccc<br>Cys Phe Glu Met Leu Ala Leu Ile Arg Gln Lys His Pro Thr Ile Pro<br>85 90 95 | | 288 |
| att ggc ctg ttg atg tat gcc aat ctg gtg ttt aac aaa ggc att gat<br>Ile Gly Leu Leu Met Tyr Ala Asn Leu Val Phe Asn Lys Gly Ile Asp<br>100 105 110 | | 336 |
| gag ttt tat gcc cag tgc gaa aaa gtc ggc gtc gat tcg gtg ctg gtt<br>Glu Phe Tyr Ala Gln Cys Glu Lys Val Gly Val Asp Ser Val Leu Val<br>115 120 125 | | 384 |
| gcc gat gtg cca gtt gaa gag tcc gcg ccc ttc cgc cag gcc gcg ttg<br>Ala Asp Val Pro Val Glu Glu Ser Ala Pro Phe Arg Gln Ala Ala Leu<br>130 135 140 | | 432 |
| cgt cat aat gtc gca cct atc ttc atc tgc ccg cca aat gcc gat gac<br>Arg His Asn Val Ala Pro Ile Phe Ile Cys Pro Pro Asn Ala Asp Asp<br>145 150 155 160 | | 480 |
| gac ctg ctg cgc cag ata gcc tct tac ggt cgt ggt tac acc tat ttg<br>Asp Leu Leu Arg Gln Ile Ala Ser Tyr Gly Arg Gly Tyr Thr Tyr Leu<br>165 170 175 | | 528 |
| ctg tca cga gca ggc gtg acc ggc gca gaa aac cgc gcc gcg tta ccc<br>Leu Ser Arg Ala Gly Val Thr Gly Ala Glu Asn Arg Ala Ala Leu Pro<br>180 185 190 | | 576 |
| ctc aat cat ctg gtt gcg aag ctg aaa gag tac aac gct gca cct cca<br>Leu Asn His Leu Val Ala Lys Leu Lys Glu Tyr Asn Ala Ala Pro Pro<br>195 200 205 | | 624 |
| ttg cag gga ttt ggt att tcc gcc ccg gat cag gta aaa gca gcg att<br>Leu Gln Gly Phe Gly Ile Ser Ala Pro Asp Gln Val Lys Ala Ala Ile<br>210 215 220 | | 672 |
| gat gca gga gct gcg ggc gcg att tct ggt tcg gcc att gtt aaa atc<br>Asp Ala Gly Ala Ala Gly Ala Ile Ser Gly Ser Ala Ile Val Lys Ile<br>225 230 235 240 | | 720 |
| atc gag caa cat att aat gag cca gag aaa atg ctg gcg gca ctg aaa<br>Ile Glu Gln His Ile Asn Glu Pro Glu Lys Met Leu Ala Ala Leu Lys<br>245 250 255 | | 768 |
| gtt ttt gta caa ccg atg aaa gcg gcg acg cgc agt taa<br>Val Phe Val Gln Pro Met Lys Ala Ala Thr Arg Ser<br>260 265 | | 807 |

<210> SEQ ID NO 14
<211> LENGTH: 268
<212> TYPE: PRT
<213> ORGANISM: Escherichia coli

<400> SEQUENCE: 14

Met Glu Arg Tyr Glu Ser Leu Phe Ala Gln Leu Lys Glu Arg Lys Glu
1               5                   10                  15

Gly Ala Phe Val Pro Phe Val Thr Leu Gly Asp Pro Gly Ile Glu Gln
            20                  25                  30

Ser Leu Lys Ile Ile Asp Thr Leu Ile Glu Ala Gly Ala Asp Ala Leu
        35                  40                  45

Glu Leu Gly Ile Pro Phe Ser Asp Pro Leu Ala Asp Gly Pro Thr Ile
    50                  55                  60

```
Gln Asn Ala Thr Leu Arg Ala Phe Ala Ala Gly Val Thr Pro Ala Gln
 65                  70                  75                  80

Cys Phe Glu Met Leu Ala Leu Ile Arg Gln Lys His Pro Thr Ile Pro
                 85                  90                  95

Ile Gly Leu Leu Met Tyr Ala Asn Leu Val Phe Asn Lys Gly Ile Asp
            100                 105                 110

Glu Phe Tyr Ala Gln Cys Glu Lys Val Gly Val Asp Ser Val Leu Val
        115                 120                 125

Ala Asp Val Pro Val Glu Ser Ala Pro Phe Arg Gln Ala Ala Leu
130                 135                 140

Arg His Asn Val Ala Pro Ile Phe Ile Cys Pro Pro Asn Ala Asp Asp
145                 150                 155                 160

Asp Leu Leu Arg Gln Ile Ala Ser Tyr Gly Arg Gly Tyr Thr Tyr Leu
                165                 170                 175

Leu Ser Arg Ala Gly Val Thr Gly Ala Glu Asn Arg Ala Ala Leu Pro
            180                 185                 190

Leu Asn His Leu Val Ala Lys Leu Lys Glu Tyr Asn Ala Ala Pro Pro
        195                 200                 205

Leu Gln Gly Phe Gly Ile Ser Ala Pro Asp Gln Val Lys Ala Ala Ile
    210                 215                 220

Asp Ala Gly Ala Ala Gly Ala Ile Ser Gly Ser Ala Ile Val Lys Ile
225                 230                 235                 240

Ile Glu Gln His Ile Asn Glu Pro Glu Lys Met Leu Ala Ala Leu Lys
                245                 250                 255

Val Phe Val Gln Pro Met Lys Ala Thr Arg Ser
            260                 265

<210> SEQ ID NO 15
<211> LENGTH: 1194
<212> TYPE: DNA
<213> ORGANISM: Escherichia coli
<220> FEATURE:
<221> NAME/KEY: CDS
<222> LOCATION: (1)..(1194)

<400> SEQUENCE: 15 atg aca aca tta ctt aac ccc tat ttt ggt gag ttt ggc ggc atg tac    48
Met Thr Thr Leu Leu Asn Pro Tyr Phe Gly Glu Phe Gly Gly Met Tyr
 1               5                  10                  15 gtg cca caa atc ctg atg cct gct ctg cgc cag ctg gaa gaa gct ttt    96
Val Pro Gln Ile Leu Met Pro Ala Leu Arg Gln Leu Glu Glu Ala Phe
             20                  25                  30 gtc agt gcg caa aaa gat cct gaa ttt cag gct cag ttc aac gac ctg   144
Val Ser Ala Gln Lys Asp Pro Glu Phe Gln Ala Gln Phe Asn Asp Leu
         35                  40                  45 ctg aaa aac tat gcc ggg cgt cca acc gcg ctg acc aaa tgc cag aac   192
Leu Lys Asn Tyr Ala Gly Arg Pro Thr Ala Leu Thr Lys Cys Gln Asn
     50                  55                  60 att aca gcc ggg acg aac acc acg ctg tat ctc aag cgt gaa gat ttg   240
Ile Thr Ala Gly Thr Asn Thr Thr Leu Tyr Leu Lys Arg Glu Asp Leu
 65                  70                  75                  80 ctg cac ggc ggc gcg cat aaa act aac cag gtg ctg ggg cag gcg ttg   288
Leu His Gly Gly Ala His Lys Thr Asn Gln Val Leu Gly Gln Ala Leu
                 85                  90                  95 ctg gcg aag cgg atg ggt aaa acc gaa atc atc gcc gaa acc ggt gcc   336
Leu Ala Lys Arg Met Gly Lys Thr Glu Ile Ile Ala Glu Thr Gly Ala
            100                 105                 110
```

| | | | | | | | | | | | | | | | | |
|---|---|---|---|---|---|---|---|---|---|---|---|---|---|---|---|---|
| ggt | cag | cat | ggc | gtg | gcg | tcg | gcc | ctt | gcc | agc | gcc | ctg | ctc | ggc | ctg | 384 |
| Gly | Gln | His | Gly | Val | Ala | Ser | Ala | Leu | Ala | Ser | Ala | Leu | Leu | Gly | Leu | |
| | | 115 | | | | 120 | | | | | 125 | | | | | |
| aaa | tgc | cgt | att | tat | atg | ggt | gcc | aaa | gac | gtt | gaa | cgc | cag | tcg | cct | 432 |
| Lys | Cys | Arg | Ile | Tyr | Met | Gly | Ala | Lys | Asp | Val | Glu | Arg | Gln | Ser | Pro | |
| | 130 | | | | | 135 | | | | | 140 | | | | | |
| aac | gtt | ttt | cgt | atg | cgc | tta | atg | ggt | gcg | gaa | gtg | atc | ccg | gtg | cat | 480 |
| Asn | Val | Phe | Arg | Met | Arg | Leu | Met | Gly | Ala | Glu | Val | Ile | Pro | Val | His | |
| 145 | | | | | 150 | | | | | 155 | | | | | 160 | |
| agc | ggt | tcc | gcg | acg | ctg | aaa | gat | gcc | tgt | aac | gag | gcg | ctg | cgc | gac | 528 |
| Ser | Gly | Ser | Ala | Thr | Leu | Lys | Asp | Ala | Cys | Asn | Glu | Ala | Leu | Arg | Asp | |
| | | | | 165 | | | | | 170 | | | | | 175 | | |
| tgg | tcc | ggt | agt | tac | gaa | acc | gcg | cac | tat | atg | ctg | ggc | acc | gca | gct | 576 |
| Trp | Ser | Gly | Ser | Tyr | Glu | Thr | Ala | His | Tyr | Met | Leu | Gly | Thr | Ala | Ala | |
| | | | 180 | | | | | 185 | | | | | 190 | | | |
| ggc | ccg | cat | cct | tat | ccg | acc | att | gtg | cgt | gag | ttt | cag | cgg | atg | att | 624 |
| Gly | Pro | His | Pro | Tyr | Pro | Thr | Ile | Val | Arg | Glu | Phe | Gln | Arg | Met | Ile | |
| | | 195 | | | | 200 | | | | | 205 | | | | | |
| ggc | gaa | gaa | acc | aaa | gcg | cag | att | ctg | gaa | aga | gaa | ggt | cgc | ctg | ccg | 672 |
| Gly | Glu | Glu | Thr | Lys | Ala | Gln | Ile | Leu | Glu | Arg | Glu | Gly | Arg | Leu | Pro | |
| 210 | | | | | 215 | | | | | 220 | | | | | | |
| gat | gcc | gtt | atc | gcc | tgt | gtt | ggc | ggc | ggt | tcg | aat | gcc | atc | ggc | atg | 720 |
| Asp | Ala | Val | Ile | Ala | Cys | Val | Gly | Gly | Gly | Ser | Asn | Ala | Ile | Gly | Met | |
| 225 | | | | | 230 | | | | | 235 | | | | | 240 | |
| ttt | gct | gat | ttc | atc | aat | gaa | acc | aac | gtc | ggc | ctg | att | ggt | gtg | gag | 768 |
| Phe | Ala | Asp | Phe | Ile | Asn | Glu | Thr | Asn | Val | Gly | Leu | Ile | Gly | Val | Glu | |
| | | | | 245 | | | | | 250 | | | | | 255 | | |
| cca | ggt | ggt | cac | ggt | atc | gaa | act | ggc | gag | cac | ggc | gca | ccg | cta | aaa | 816 |
| Pro | Gly | Gly | His | Gly | Ile | Glu | Thr | Gly | Glu | His | Gly | Ala | Pro | Leu | Lys | |
| | | | 260 | | | | | 265 | | | | | 270 | | | |
| cat | ggt | cgc | gtg | ggt | atc | tat | ttc | ggt | atg | aaa | gcg | ccg | atg | atg | caa | 864 |
| His | Gly | Arg | Val | Gly | Ile | Tyr | Phe | Gly | Met | Lys | Ala | Pro | Met | Met | Gln | |
| | | 275 | | | | 280 | | | | | 285 | | | | | |
| acc | gaa | gac | ggg | cag | att | gaa | gaa | tct | tac | tcc | atc | tcc | gcc | gga | ctg | 912 |
| Thr | Glu | Asp | Gly | Gln | Ile | Glu | Glu | Ser | Tyr | Ser | Ile | Ser | Ala | Gly | Leu | |
| 290 | | | | | 295 | | | | | 300 | | | | | | |
| gat | ttc | ccg | tct | gtc | ggc | cca | caa | cac | gcg | tat | ctt | aac | agc | act | gga | 960 |
| Asp | Phe | Pro | Ser | Val | Gly | Pro | Gln | His | Ala | Tyr | Leu | Asn | Ser | Thr | Gly | |
| 305 | | | | | 310 | | | | | 315 | | | | | 320 | |
| cgc | gct | gat | tac | gtg | tct | att | acc | gat | gat | gaa | gcc | ctt | gaa | gcc | ttc | 1008 |
| Arg | Ala | Asp | Tyr | Val | Ser | Ile | Thr | Asp | Asp | Glu | Ala | Leu | Glu | Ala | Phe | |
| | | | | 325 | | | | | 330 | | | | | 335 | | |
| aaa | acg | ctg | tgc | ctg | cac | gaa | ggg | atc | atc | ccg | gcg | ctg | gaa | tcc | tcc | 1056 |
| Lys | Thr | Leu | Cys | Leu | His | Glu | Gly | Ile | Ile | Pro | Ala | Leu | Glu | Ser | Ser | |
| | | | 340 | | | | | 345 | | | | | 350 | | | |
| cac | gcc | ctg | gcc | cat | gcg | ttg | aaa | atg | atg | cgc | gaa | aac | ccg | gat | aaa | 1104 |
| His | Ala | Leu | Ala | His | Ala | Leu | Lys | Met | Met | Arg | Glu | Asn | Pro | Asp | Lys | |
| | | 355 | | | | 360 | | | | | 365 | | | | | |
| gag | cag | cta | ctg | gtg | gtt | aac | ctt | tcc | ggt | cgc | ggc | gat | aaa | gac | atc | 1152 |
| Glu | Gln | Leu | Leu | Val | Val | Asn | Leu | Ser | Gly | Arg | Gly | Asp | Lys | Asp | Ile | |
| 370 | | | | | 375 | | | | | 380 | | | | | | |
| ttc | acc | gtt | cac | gat | att | ttg | aaa | gca | cga | ggg | gaa | atc | tga | | | 1194 |
| Phe | Thr | Val | His | Asp | Ile | Leu | Lys | Ala | Arg | Gly | Glu | Ile | | | | |
| 385 | | | | | 390 | | | | | 395 | | | | | | |

<210> SEQ ID NO 16
<211> LENGTH: 397
<212> TYPE: PRT
<213> ORGANISM: Escherichia coli

<400> SEQUENCE: 16

-continued

```
Met Thr Thr Leu Leu Asn Pro Tyr Phe Gly Glu Phe Gly Met Tyr
 1               5                  10                 15

Val Pro Gln Ile Leu Met Pro Ala Leu Arg Gln Leu Glu Glu Ala Phe
             20                  25                  30

Val Ser Ala Gln Lys Asp Pro Glu Phe Gln Ala Gln Phe Asn Asp Leu
         35                  40                  45

Leu Lys Asn Tyr Ala Gly Arg Pro Thr Ala Leu Thr Lys Cys Gln Asn
     50                  55                  60

Ile Thr Ala Gly Thr Asn Thr Thr Leu Tyr Leu Lys Arg Glu Asp Leu
 65                  70                  75                  80

Leu His Gly Gly Ala His Lys Thr Asn Gln Val Leu Gly Gln Ala Leu
                 85                  90                  95

Leu Ala Lys Arg Met Gly Lys Thr Glu Ile Ile Ala Glu Thr Gly Ala
             100                 105                 110

Gly Gln His Gly Val Ala Ser Ala Leu Ala Ser Ala Leu Leu Gly Leu
         115                 120                 125

Lys Cys Arg Ile Tyr Met Gly Ala Lys Asp Val Glu Arg Gln Ser Pro
     130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                 165                 170                 175

Trp Ser Gly Ser Tyr Glu Thr Ala His Tyr Met Leu Gly Thr Ala Ala
             180                 185                 190

Gly Pro His Pro Tyr Pro Thr Ile Val Arg Glu Phe Gln Arg Met Ile
         195                 200                 205

Gly Glu Glu Thr Lys Ala Gln Ile Leu Glu Arg Glu Gly Arg Leu Pro
     210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                 245                 250                 255

Pro Gly Gly His Gly Ile Glu Thr Gly Glu His Gly Ala Pro Leu Lys
             260                 265                 270

His Gly Arg Val Gly Ile Tyr Phe Gly Met Lys Ala Pro Met Met Gln
         275                 280                 285

Thr Glu Asp Gly Gln Ile Glu Glu Ser Tyr Ser Ile Ser Ala Gly Leu
     290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                 325                 330                 335

Lys Thr Leu Cys Leu His Glu Gly Ile Ile Pro Ala Leu Glu Ser Ser
             340                 345                 350

His Ala Leu Ala His Ala Leu Lys Met Met Arg Glu Asn Pro Asp Lys
         355                 360                 365

Glu Gln Leu Leu Val Val Asn Leu Ser Gly Arg Gly Asp Lys Asp Ile
     370                 375                 380

Phe Thr Val His Asp Ile Leu Lys Ala Arg Gly Glu Ile
385                 390                 395
```

<210> SEQ ID NO 17
<211> LENGTH: 44

```
<212> TYPE: DNA
<213> ORGANISM: Artificial
<220> FEATURE:
<223> OTHER INFORMATION: 5'-primer-evgAS

<400> SEQUENCE: 17
gggaattcac gcctgtagga ttagtaagaa gacttatagt gcca                44

<210> SEQ ID NO 18
<211> LENGTH: 44
<212> TYPE: DNA
<213> ORGANISM: Artificial
<220> FEATURE:
<223> OTHER INFORMATION: 3'-primer-evgAS

<400> SEQUENCE: 18
ggaagcttcc acatttgaac attgtgggag ccgctattta gtca                44

<210> SEQ ID NO 19
<211> LENGTH: 44
<212> TYPE: DNA
<213> ORGANISM: Artificial
<220> FEATURE:
<223> OTHER INFORMATION: 5'-primer-gadE

<400> SEQUENCE: 19
ggggatccaa agtgaacaaa gagttccgta agcgttgatg ctat                44

<210> SEQ ID NO 20
<211> LENGTH: 44
<212> TYPE: DNA
<213> ORGANISM: Artificial
<220> FEATURE:
<223> OTHER INFORMATION: 3'-primer-gadE

<400> SEQUENCE: 20
ggaagcttat gccagccatc aatttcagtt gcttatgtcc tgac                44

<210> SEQ ID NO 21
<211> LENGTH: 47
<212> TYPE: DNA
<213> ORGANISM: Artificial
<220> FEATURE:
<223> OTHER INFORMATION: 5'-primer-ydeO

<400> SEQUENCE: 21
ggaagcttaa cgcggggcag ggaatggctg ccccatttaa ttcttac             47

<210> SEQ ID NO 22
<211> LENGTH: 46
<212> TYPE: DNA
<213> ORGANISM: Artificial
<220> FEATURE:
<223> OTHER INFORMATION: 3'-primer-ydeO

<400> SEQUENCE: 22
gggaattcgc tgagtatttc agaaatgggt cgcattgcaa gagatc              46

<210> SEQ ID NO 23
<211> LENGTH: 615
<212> TYPE: DNA
<213> ORGANISM: Escherichia coli
<220> FEATURE:
<221> NAME/KEY: CDS
<222> LOCATION: (1)..(615)

<400> SEQUENCE: 23
```

```
atg aac gca ata att att gat gac cat cct ctt gct atc gca gca att        48
Met Asn Ala Ile Ile Ile Asp Asp His Pro Leu Ala Ile Ala Ala Ile
1               5                   10                  15 cgt aat tta ttg atc aaa aac gat att gaa atc tta gca gag ttg act        96
Arg Asn Leu Leu Ile Lys Asn Asp Ile Glu Ile Leu Ala Glu Leu Thr
            20                  25                  30 gaa ggc gga agt gcc gtt cag cgg gtg gaa aca ctt aag cct gat atc       144
Glu Gly Gly Ser Ala Val Gln Arg Val Glu Thr Leu Lys Pro Asp Ile
        35                  40                  45 gtc atc att gat gtc gat atc ccc gga gtt aac ggt atc cag gtg tta       192
Val Ile Ile Asp Val Asp Ile Pro Gly Val Asn Gly Ile Gln Val Leu
50                  55                  60 gaa acg ctg agg aag cgc caa tat agc gga att att att atc gtc tcc       240
Glu Thr Leu Arg Lys Arg Gln Tyr Ser Gly Ile Ile Ile Ile Val Ser
65                  70                  75                  80 gct aaa aat gac cat ttt tac ggg aaa cat tgt gct gat gct ggc gct       288
Ala Lys Asn Asp His Phe Tyr Gly Lys His Cys Ala Asp Ala Gly Ala
            85                  90                  95 aat ggt ttc gtg agt aaa aaa gaa ggc atg aac aat atc att gcg gct       336
Asn Gly Phe Val Ser Lys Lys Glu Gly Met Asn Asn Ile Ile Ala Ala
        100                 105                 110 att gaa gct gca aaa aat ggc tac tgc tat ttc ccc ttc tct ctc aac       384
Ile Glu Ala Ala Lys Asn Gly Tyr Cys Tyr Phe Pro Phe Ser Leu Asn
    115                 120                 125 cgg ttt gtt gga agt tta acg tcc gac cag caa aaa ctc gac tcc tta       432
Arg Phe Val Gly Ser Leu Thr Ser Asp Gln Gln Lys Leu Asp Ser Leu
130                 135                 140 tcg aaa caa gaa att agt gtc atg cgg tat att ctt gat ggc aag gat       480
Ser Lys Gln Glu Ile Ser Val Met Arg Tyr Ile Leu Asp Gly Lys Asp
145                 150                 155                 160 aat aat gac att gct gaa aaa atg ttc atc agc aac aaa act gtc agc       528
Asn Asn Asp Ile Ala Glu Lys Met Phe Ile Ser Asn Lys Thr Val Ser
                165                 170                 175 act tat aaa agt cgc ctg atg gaa aaa tta gaa tgt aaa tca ctg atg       576
Thr Tyr Lys Ser Arg Leu Met Glu Lys Leu Glu Cys Lys Ser Leu Met
            180                 185                 190 gat ctt tac aca ttc gca caa cgt aac aaa atc ggc taa                    615
Asp Leu Tyr Thr Phe Ala Gln Arg Asn Lys Ile Gly
        195                 200
```

<210> SEQ ID NO 24
<211> LENGTH: 204
<212> TYPE: PRT
<213> ORGANISM: Escherichia coli

<400> SEQUENCE: 24

```
Met Asn Ala Ile Ile Ile Asp Asp His Pro Leu Ala Ile Ala Ala Ile
1               5                   10                  15

Arg Asn Leu Leu Ile Lys Asn Asp Ile Glu Ile Leu Ala Glu Leu Thr
            20                  25                  30

Glu Gly Gly Ser Ala Val Gln Arg Val Glu Thr Leu Lys Pro Asp Ile
        35                  40                  45

Val Ile Ile Asp Val Asp Ile Pro Gly Val Asn Gly Ile Gln Val Leu
    50                  55                  60

Glu Thr Leu Arg Lys Arg Gln Tyr Ser Gly Ile Ile Ile Ile Val Ser
65                  70                  75                  80

Ala Lys Asn Asp His Phe Tyr Gly Lys His Cys Ala Asp Ala Gly Ala
                85                  90                  95
```

```
Asn Gly Phe Val Ser Lys Lys Glu Gly Met Asn Asn Ile Ile Ala Ala
                100                 105                 110

Ile Glu Ala Ala Lys Asn Gly Tyr Cys Tyr Phe Pro Phe Ser Leu Asn
            115                 120                 125

Arg Phe Val Gly Ser Leu Thr Ser Asp Gln Gln Lys Leu Asp Ser Leu
        130                 135                 140

Ser Lys Gln Glu Ile Ser Val Met Arg Tyr Ile Leu Asp Gly Lys Asp
145                 150                 155                 160

Asn Asn Asp Ile Ala Glu Lys Met Phe Ile Ser Asn Lys Thr Val Ser
                165                 170                 175

Thr Tyr Lys Ser Arg Leu Met Glu Lys Leu Glu Cys Lys Ser Leu Met
            180                 185                 190

Asp Leu Tyr Thr Phe Ala Gln Arg Asn Lys Ile Gly
        195                 200

<210> SEQ ID NO 25
<211> LENGTH: 3594
<212> TYPE: DNA
<213> ORGANISM: Escherichia coli
<220> FEATURE:
<221> NAME/KEY: CDS
<222> LOCATION: (1)..(3594)

<400> SEQUENCE: 25
```

| | | | | | | | | | | | | | | | | |
|---|---|---|---|---|---|---|---|---|---|---|---|---|---|---|---|---|
| atg | aag | ttt | tta | ccc | tat | att | ttt | ctt | ctc | tgt | tgt | ggt | ctt | tgg | tcg | 48 |
| Met | Lys | Phe | Leu | Pro | Tyr | Ile | Phe | Leu | Leu | Cys | Cys | Gly | Leu | Trp | Ser | |
| 1 | | | | 5 | | | | | 10 | | | | | 15 | | |
| acc | ata | agt | ttc | gca | gac | gaa | gat | tac | atc | gaa | tat | cgt | ggc | atc | agt | 96 |
| Thr | Ile | Ser | Phe | Ala | Asp | Glu | Asp | Tyr | Ile | Glu | Tyr | Arg | Gly | Ile | Ser | |
| | | | 20 | | | | | 25 | | | | | 30 | | | |
| agt | aac | aac | cgt | gtc | aca | ctt | gat | cca | cta | cgt | ctg | agc | aac | aag | gaa | 144 |
| Ser | Asn | Asn | Arg | Val | Thr | Leu | Asp | Pro | Leu | Arg | Leu | Ser | Asn | Lys | Glu | |
| | | 35 | | | | | 40 | | | | | 45 | | | | |
| tta | cgt | tgg | tta | gcg | agc | aaa | aaa | aat | ctt | gtg | att | gca | gta | cat | aag | 192 |
| Leu | Arg | Trp | Leu | Ala | Ser | Lys | Lys | Asn | Leu | Val | Ile | Ala | Val | His | Lys | |
| 50 | | | | | 55 | | | | | 60 | | | | | | |
| tcc | caa | acg | gct | acg | ttg | ttg | cat | acc | gat | tcg | cag | caa | cgg | gtt | cgt | 240 |
| Ser | Gln | Thr | Ala | Thr | Leu | Leu | His | Thr | Asp | Ser | Gln | Gln | Arg | Val | Arg | |
| 65 | | | | 70 | | | | | 75 | | | | | 80 | | |
| ggt | att | aat | gct | gat | tat | tta | aat | ctt | tta | aaa | aga | gcg | tta | aat | atc | 288 |
| Gly | Ile | Asn | Ala | Asp | Tyr | Leu | Asn | Leu | Leu | Lys | Arg | Ala | Leu | Asn | Ile | |
| | | | | 85 | | | | | 90 | | | | | 95 | | |
| aaa | tta | aca | ctc | cgg | gaa | tac | gca | gat | cat | caa | aaa | gca | atg | gac | gcg | 336 |
| Lys | Leu | Thr | Leu | Arg | Glu | Tyr | Ala | Asp | His | Gln | Lys | Ala | Met | Asp | Ala | |
| | | | 100 | | | | | 105 | | | | | 110 | | | |
| ctt | gca | gaa | ggt | gaa | gtc | gat | ata | gtg | tta | tca | cat | tta | gtt | act | tcg | 384 |
| Leu | Ala | Glu | Gly | Glu | Val | Asp | Ile | Val | Leu | Ser | His | Leu | Val | Thr | Ser | |
| | | 115 | | | | | 120 | | | | | 125 | | | | |
| ccg | cct | ctt | aat | aat | gac | att | gct | gca | acc | aaa | cca | ttg | ata | att | acc | 432 |
| Pro | Pro | Leu | Asn | Asn | Asp | Ile | Ala | Ala | Thr | Lys | Pro | Leu | Ile | Ile | Thr | |
| | | 130 | | | | | 135 | | | | | 140 | | | | |
| ttt | ccg | gcg | ctg | gta | acc | acc | ctt | cac | gac | tca | atg | cga | ccg | ctt | acc | 480 |
| Phe | Pro | Ala | Leu | Val | Thr | Thr | Leu | His | Asp | Ser | Met | Arg | Pro | Leu | Thr | |
| 145 | | | | | 150 | | | | | 155 | | | | | 160 | |
| tca | cca | aaa | cca | gta | aat | att | gct | cgg | gta | gca | aat | tac | ccc | cca | gac | 528 |
| Ser | Pro | Lys | Pro | Val | Asn | Ile | Ala | Arg | Val | Ala | Asn | Tyr | Pro | Pro | Asp | |
| | | | | 165 | | | | | 170 | | | | | 175 | | |
| gag | gta | att | cat | caa | tca | ttt | cca | aaa | gca | aca | att | atc | tct | ttt | aca | 576 |
| Glu | Val | Ile | His | Gln | Ser | Phe | Pro | Lys | Ala | Thr | Ile | Ile | Ser | Phe | Thr | |
| | | | 180 | | | | | 185 | | | | | 190 | | | |

```
aat tta tat cag gca tta gca tcc gtc tca gct ggg cac aat gat tac      624
Asn Leu Tyr Gln Ala Leu Ala Ser Val Ser Ala Gly His Asn Asp Tyr
        195                 200                 205 ttt att ggt agt aac atc att acc agc agt atg att tcc cgc tat ttc      672
Phe Ile Gly Ser Asn Ile Ile Thr Ser Ser Met Ile Ser Arg Tyr Phe
210                 215                 220 act cac tcc tta aat gta gtg aaa tat tat aac tcg ccg cgt caa tat      720
Thr His Ser Leu Asn Val Val Lys Tyr Tyr Asn Ser Pro Arg Gln Tyr
225                 230                 235                 240 aat ttt ttc ttg acc aga aaa gaa tct gtc att ctt aat gaa gta ctc      768
Asn Phe Phe Leu Thr Arg Lys Glu Ser Val Ile Leu Asn Glu Val Leu
                245                 250                 255 aat aga ttt gtt gat gct tta aca aat gaa gtt cgc tat gaa gta tca      816
Asn Arg Phe Val Asp Ala Leu Thr Asn Glu Val Arg Tyr Glu Val Ser
        260                 265                 270 caa aat tgg ctt gat aca gga aac ctg gcc ttt ctg aac aaa cca tta      864
Gln Asn Trp Leu Asp Thr Gly Asn Leu Ala Phe Leu Asn Lys Pro Leu
275                 280                 285 gaa ctc act gaa cat gaa aaa cag tgg att aag cag cat ccc aat tta      912
Glu Leu Thr Glu His Glu Lys Gln Trp Ile Lys Gln His Pro Asn Leu
290                 295                 300 aag gtg ctg gaa aat cct tac tcg ccc ccc tat tct atg acg gat gaa      960
Lys Val Leu Glu Asn Pro Tyr Ser Pro Pro Tyr Ser Met Thr Asp Glu
305                 310                 315                 320 aat ggc tcg gtt cgg ggc gtt atg ggg gac att ctt aat att att acc     1008
Asn Gly Ser Val Arg Gly Val Met Gly Asp Ile Leu Asn Ile Ile Thr
                325                 330                 335 ttg caa aca ggt tta aat ttt tct ccg atc acc gtt tca cac aat atc     1056
Leu Gln Thr Gly Leu Asn Phe Ser Pro Ile Thr Val Ser His Asn Ile
        340                 345                 350 cat gct gga aca cag ctt agc ccc gga gga tgg gat ata ata cct ggc     1104
His Ala Gly Thr Gln Leu Ser Pro Gly Gly Trp Asp Ile Ile Pro Gly
355                 360                 365 gct att tat agt gaa gat cga gaa aat aat gtt tta ttt gct gaa gcc     1152
Ala Ile Tyr Ser Glu Asp Arg Glu Asn Asn Val Leu Phe Ala Glu Ala
370                 375                 380 ttc ata aca acg cct tac gtt ttt gtc atg caa aaa gcg cct gac agt     1200
Phe Ile Thr Thr Pro Tyr Val Phe Val Met Gln Lys Ala Pro Asp Ser
385                 390                 395                 400 gaa caa aca tta aaa aaa gga atg aaa gtt gcc att cca tat tat tat     1248
Glu Gln Thr Leu Lys Lys Gly Met Lys Val Ala Ile Pro Tyr Tyr Tyr
                405                 410                 415 gag ctg cat tcg caa tta aaa gag atg tat ccg gag gtt gaa tgg ata     1296
Glu Leu His Ser Gln Leu Lys Glu Met Tyr Pro Glu Val Glu Trp Ile
        420                 425                 430 cag gtc gat aat gcc agc gct gca ttt cac aag gtt aag gaa ggt gaa     1344
Gln Val Asp Asn Ala Ser Ala Ala Phe His Lys Val Lys Glu Gly Glu
435                 440                 445 ctt gat gct ctg gtc gcg aca cag cta aat tcg cgt tac atg atc gat     1392
Leu Asp Ala Leu Val Ala Thr Gln Leu Asn Ser Arg Tyr Met Ile Asp
450                 455                 460 cat tac tat cct aat gaa ctt tat cat ttt ctt att cct ggc gtt ccg     1440
His Tyr Tyr Pro Asn Glu Leu Tyr His Phe Leu Ile Pro Gly Val Pro
465                 470                 475                 480 aat gca tcg ctt tcg ttc gct ttt cct cgc gga gaa ccg gaa ctt aag     1488
Asn Ala Ser Leu Ser Phe Ala Phe Pro Arg Gly Glu Pro Glu Leu Lys
                485                 490                 495 gat att att aat aaa gca ctg aat gca att ccc cca agc gaa gtt ctg     1536
Asp Ile Ile Asn Lys Ala Leu Asn Ala Ile Pro Pro Ser Glu Val Leu
```

-continued

```
                500                505                510
cgc ctg acg gaa aaa tgg att aaa atg ccc aat gtg acc att gac aca    1584
Arg Leu Thr Glu Lys Trp Ile Lys Met Pro Asn Val Thr Ile Asp Thr
        515                520                525 tgg gac cta tat agc gag caa ttt tat att gtt acg aca tta tcc gtt    1632
Trp Asp Leu Tyr Ser Glu Gln Phe Tyr Ile Val Thr Thr Leu Ser Val
530                535                540 tta tta gtt ggc agt agc ctt tta tgg gga ttc tac ctg tta cgc tca    1680
Leu Leu Val Gly Ser Ser Leu Leu Trp Gly Phe Tyr Leu Leu Arg Ser
545                550                555                560 gtt cgt cgt cgt aaa gtc att cag ggt gat tta gaa aac caa ata tca    1728
Val Arg Arg Arg Lys Val Ile Gln Gly Asp Leu Glu Asn Gln Ile Ser
                565                570                575 ttc cga aaa gca ctc tcg gat tcc tta ccg aat cca act tat gtt gta    1776
Phe Arg Lys Ala Leu Ser Asp Ser Leu Pro Asn Pro Thr Tyr Val Val
            580                585                590 aac tgg caa ggt aat gtc att agt cat aat agt gct ttt gaa cat tat    1824
Asn Trp Gln Gly Asn Val Ile Ser His Asn Ser Ala Phe Glu His Tyr
        595                600                605 ttc act gcg gat tac tac aaa aat gca atg tta cca tta gaa aac agt    1872
Phe Thr Ala Asp Tyr Tyr Lys Asn Ala Met Leu Pro Leu Glu Asn Ser
610                615                620 gac tca ccc ttt aaa gat gtt ttt tct aat gcg cat gaa gtc aca gca    1920
Asp Ser Pro Phe Lys Asp Val Phe Ser Asn Ala His Glu Val Thr Ala
625                630                635                640 gaa acg aaa gaa aat cga aca ata tac aca cag gta ttt gaa att gat    1968
Glu Thr Lys Glu Asn Arg Thr Ile Tyr Thr Gln Val Phe Glu Ile Asp
                645                650                655 aat ggc atc gag aaa aga tgc att aat cac tgg cat aca tta tgc aat    2016
Asn Gly Ile Glu Lys Arg Cys Ile Asn His Trp His Thr Leu Cys Asn
            660                665                670 ctt cct gca agt gac aat gca gta tat att tgt ggt tgg caa gat att    2064
Leu Pro Ala Ser Asp Asn Ala Val Tyr Ile Cys Gly Trp Gln Asp Ile
        675                680                685 act gaa acg cgt gat cta att aat gca ctc gag gta gaa aaa aat aaa    2112
Thr Glu Thr Arg Asp Leu Ile Asn Ala Leu Glu Val Glu Lys Asn Lys
690                695                700 gcg ata aag gct acc gta gca aaa agt cag ttt ctg gca acg atg agt    2160
Ala Ile Lys Ala Thr Val Ala Lys Ser Gln Phe Leu Ala Thr Met Ser
705                710                715                720 cac gaa ata aga aca cca ata agc tct att atg ggc ttc ctg gaa ctt    2208
His Glu Ile Arg Thr Pro Ile Ser Ser Ile Met Gly Phe Leu Glu Leu
                725                730                735 ctg tcg ggt tct ggt ctt agc aag gag caa cgg gtg gag gcg att tca    2256
Leu Ser Gly Ser Gly Leu Ser Lys Glu Gln Arg Val Glu Ala Ile Ser
            740                745                750 ctt gcc tac gcc acc gga caa tca ctc ctc ggc tta att ggt gaa atc    2304
Leu Ala Tyr Ala Thr Gly Gln Ser Leu Leu Gly Leu Ile Gly Glu Ile
        755                760                765 ctt gat gtc gac aaa att gaa tcg ggt aac tat caa ctt caa cca caa    2352
Leu Asp Val Asp Lys Ile Glu Ser Gly Asn Tyr Gln Leu Gln Pro Gln
770                775                780 tgg gtc gat atc cct act tta gtc cag aac act tgt cac tct ttc ggt    2400
Trp Val Asp Ile Pro Thr Leu Val Gln Asn Thr Cys His Ser Phe Gly
785                790                795                800 gcg att gct gca agc aaa tcg atc gca tta agt tgc agc agt acg ttt    2448
Ala Ile Ala Ala Ser Lys Ser Ile Ala Leu Ser Cys Ser Ser Thr Phe
                805                810                815 cct gaa cat tac ctg gtt aag atc gac cct cag gcg ttt aag cag gtc    2496
```

```
              Pro Glu His Tyr Leu Val Lys Ile Asp Pro Gln Ala Phe Lys Gln Val
                      820                 825                 830 tta tca aat tta ctg agt aat gct ctc aaa ttt acc acc gag ggg gca      2544
Leu Ser Asn Leu Leu Ser Asn Ala Leu Lys Phe Thr Thr Glu Gly Ala
            835                 840                 845 gta aaa att acg acc tcc ctg ggt cac att gat gac aac cac gct gtt      2592
Val Lys Ile Thr Thr Ser Leu Gly His Ile Asp Asp Asn His Ala Val
        850                 855                 860 atc aaa atg acg att atg gat tct gga agt gga tta tcg cag gaa gaa      2640
Ile Lys Met Thr Ile Met Asp Ser Gly Ser Gly Leu Ser Gln Glu Glu
865                 870                 875                 880 caa caa caa ctg ttt aaa cgc tac agc caa aca agt gca ggt cgt cag      2688
Gln Gln Gln Leu Phe Lys Arg Tyr Ser Gln Thr Ser Ala Gly Arg Gln
                885                 890                 895 caa aca ggt tct ggt tta ggc tta atg atc tgc aaa gaa tta att aaa      2736
Gln Thr Gly Ser Gly Leu Gly Leu Met Ile Cys Lys Glu Leu Ile Lys
            900                 905                 910 aat atg cag ggc gat ttg tca tta gaa agt cat cca ggc ata gga aca      2784
Asn Met Gln Gly Asp Leu Ser Leu Glu Ser His Pro Gly Ile Gly Thr
        915                 920                 925 aca ttt acg atc aca atc ccg gta gaa att agc cag caa gtg gcg act      2832
Thr Phe Thr Ile Thr Ile Pro Val Glu Ile Ser Gln Gln Val Ala Thr
930                 935                 940 gtc gag gca aaa gca gaa caa ccc atc aca cta cct gaa aag ttg agc      2880
Val Glu Ala Lys Ala Glu Gln Pro Ile Thr Leu Pro Glu Lys Leu Ser
945                 950                 955                 960 ata tta atc gcg gat gat cat ccg acc aac agg cta tta ctc aaa cgc      2928
Ile Leu Ile Ala Asp Asp His Pro Thr Asn Arg Leu Leu Leu Lys Arg
                965                 970                 975 cag cta aat cta tta gga tat gat gtt gat gaa gcc act gat ggt gtg      2976
Gln Leu Asn Leu Leu Gly Tyr Asp Val Asp Glu Ala Thr Asp Gly Val
            980                 985                 990 caa gcg cta cac aaa gtc agt atg  caa cat tat gat ctg  ctt att act    3024
Gln Ala Leu His Lys Val Ser Met  Gln His Tyr Asp Leu  Leu Ile Thr
        995                 1000                1005 gac gtt  aat atg ccg aat atg  gat ggt ttt gag ttg  act cgc aaa       3069
Asp Val  Asn Met Pro Asn Met  Asp Gly Phe Glu Leu  Thr Arg Lys
    1010                1015                 1020 ctc cgt  gag caa aat tct tcc  tta ccc atc tgg ggg  ctt aca gcc       3114
Leu Arg  Glu Gln Asn Ser Ser  Leu Pro Ile Trp Gly  Leu Thr Ala
1025                 1030                1035 aac gca  cag gct aac gaa cgt  gaa aaa ggg tta agt  tgc ggc atg       3159
Asn Ala  Gln Ala Asn Glu Arg  Glu Lys Gly Leu Ser  Cys Gly Met
     1040                1045                1050 aac tta  tgt ttg ttc aaa ccg  ttg acc ctg gat gta  ctg aaa aca       3204
Asn Leu  Cys Leu Phe Lys Pro  Leu Thr Leu Asp Val  Leu Lys Thr
1055                 1060                1065 cat tta  agt cag tta cac caa  gtt gcg cat att gca  cct cag tat       3249
His Leu  Ser Gln Leu His Gln  Val Ala His Ile Ala  Pro Gln Tyr
    1070                1075                1080 cgc cac  ctt gat atc gaa gcc  ctg aaa aat aat acg  gcg aac gat       3294
Arg His  Leu Asp Ile Glu Ala  Leu Lys Asn Asn Thr  Ala Asn Asp
1085                 1090                1095 cta caa  ctg atg cag gag att  ctc atg act ttc cag  cat gaa acg       3339
Leu Gln  Leu Met Gln Glu Ile  Leu Met Thr Phe Gln  His Glu Thr
    1100                1105                1110 cat aaa  gat cta ccc gct gcg  ttt caa gca cta gaa  gct ggc gat       3384
His Lys  Asp Leu Pro Ala Ala  Phe Gln Ala Leu Glu  Ala Gly Asp
1115                 1120                1125
```

| aac | aga | act | ttc | cat | cag | tgt | att | cat | cgc | atc | cac | ggt | gcg | gct | 3429 |
| Asn | Arg | Thr | Phe | His | Gln | Cys | Ile | His | Arg | Ile | His | Gly | Ala | Ala | |
| 1130 | | | | 1135 | | | | | 1140 | | | | | | |

| aac | atc | ctg | aat | ttg | caa | aag | ttg | att | aat | att | agc | cat | cag | tta | 3474 |
| Asn | Ile | Leu | Asn | Leu | Gln | Lys | Leu | Ile | Asn | Ile | Ser | His | Gln | Leu | |
| 1145 | | | | 1150 | | | | | 1155 | | | | | | |

| gaa | ata | aca | cct | gtt | tca | gat | gac | agt | aag | cct | gaa | att | ctt | cag | 3519 |
| Glu | Ile | Thr | Pro | Val | Ser | Asp | Asp | Ser | Lys | Pro | Glu | Ile | Leu | Gln | |
| 1160 | | | | 1165 | | | | | 1170 | | | | | | |

| ttg | ctg | aac | tct | gta | aaa | gaa | cac | att | gca | gag | ctg | gac | cag | gag | 3564 |
| Leu | Leu | Asn | Ser | Val | Lys | Glu | His | Ile | Ala | Glu | Leu | Asp | Gln | Glu | |
| 1175 | | | | 1180 | | | | | 1185 | | | | | | |

| att | gct | gtt | ttc | tgt | cag | aaa | aat | gac | taa | 3594 |
| Ile | Ala | Val | Phe | Cys | Gln | Lys | Asn | Asp | | |
| 1190 | | | | | 1195 | | | | | |

<210> SEQ ID NO 26
<211> LENGTH: 1197
<212> TYPE: PRT
<213> ORGANISM: Escherichia coli

<400> SEQUENCE: 26

| Met | Lys | Phe | Leu | Pro | Tyr | Ile | Phe | Leu | Leu | Cys | Cys | Gly | Leu | Trp | Ser |
|---|---|---|---|---|---|---|---|---|---|---|---|---|---|---|---|
| 1 | | | | 5 | | | | | 10 | | | | | 15 | |

| Thr | Ile | Ser | Phe | Ala | Asp | Glu | Asp | Tyr | Ile | Glu | Tyr | Arg | Gly | Ile | Ser |
| | | | 20 | | | | | 25 | | | | | 30 | | |

| Ser | Asn | Asn | Arg | Val | Thr | Leu | Asp | Pro | Leu | Arg | Leu | Ser | Asn | Lys | Glu |
| | | 35 | | | | | 40 | | | | | 45 | | | |

| Leu | Arg | Trp | Leu | Ala | Ser | Lys | Lys | Asn | Leu | Val | Ile | Ala | Val | His | Lys |
| | 50 | | | | | 55 | | | | | 60 | | | | |

| Ser | Gln | Thr | Ala | Thr | Leu | Leu | His | Thr | Asp | Ser | Gln | Gln | Arg | Val | Arg |
| 65 | | | | | 70 | | | | | 75 | | | | | 80 |

| Gly | Ile | Asn | Ala | Asp | Tyr | Leu | Asn | Leu | Lys | Arg | Ala | Leu | Asn | Ile | |
| | | | | 85 | | | | | 90 | | | | | 95 | |

| Lys | Leu | Thr | Leu | Arg | Glu | Tyr | Ala | Asp | His | Gln | Lys | Ala | Met | Asp | Ala |
| | | | 100 | | | | | 105 | | | | | 110 | | |

| Leu | Ala | Glu | Gly | Glu | Val | Asp | Ile | Val | Leu | Ser | His | Leu | Val | Thr | Ser |
| | | | 115 | | | | | 120 | | | | | 125 | | |

| Pro | Pro | Leu | Asn | Asn | Asp | Ile | Ala | Ala | Thr | Lys | Pro | Leu | Ile | Ile | Thr |
| | | 130 | | | | | 135 | | | | | 140 | | | |

| Phe | Pro | Ala | Leu | Val | Thr | Thr | Leu | His | Asp | Ser | Met | Arg | Pro | Leu | Thr |
| 145 | | | | | 150 | | | | | 155 | | | | | 160 |

| Ser | Pro | Lys | Pro | Val | Asn | Ile | Ala | Arg | Val | Ala | Asn | Tyr | Pro | Pro | Asp |
| | | | 165 | | | | | 170 | | | | | 175 | | |

| Glu | Val | Ile | His | Gln | Ser | Phe | Pro | Lys | Ala | Thr | Ile | Ser | Phe | Thr | |
| | | | 180 | | | | | 185 | | | | | 190 | | |

| Asn | Leu | Tyr | Gln | Ala | Leu | Ala | Ser | Val | Ser | Ala | Gly | His | Asn | Asp | Tyr |
| | | 195 | | | | | 200 | | | | | 205 | | | |

| Phe | Ile | Gly | Ser | Asn | Ile | Ile | Thr | Ser | Ser | Met | Ile | Ser | Arg | Tyr | Phe |
| | 210 | | | | | 215 | | | | | 220 | | | | |

| Thr | His | Ser | Leu | Asn | Val | Val | Lys | Tyr | Tyr | Asn | Ser | Pro | Arg | Gln | Tyr |
| 225 | | | | | 230 | | | | | 235 | | | | | 240 |

| Asn | Phe | Phe | Leu | Thr | Arg | Lys | Glu | Ser | Val | Ile | Leu | Asn | Glu | Val | Leu |
| | | | 245 | | | | | 250 | | | | | 255 | | |

| Asn | Arg | Phe | Val | Asp | Ala | Leu | Thr | Asn | Glu | Val | Arg | Tyr | Glu | Val | Ser |
| | | | 260 | | | | | 265 | | | | | 270 | | |

```
Gln Asn Trp Leu Asp Thr Gly Asn Leu Ala Phe Leu Asn Lys Pro Leu
            275                 280                 285
Glu Leu Thr Glu His Glu Lys Gln Trp Ile Lys Gln His Pro Asn Leu
        290                 295                 300
Lys Val Leu Glu Asn Pro Tyr Ser Pro Tyr Ser Met Thr Asp Glu
305                 310                 315                 320
Asn Gly Ser Val Arg Gly Val Met Gly Asp Ile Leu Asn Ile Ile Thr
                    325                 330                 335
Leu Gln Thr Gly Leu Asn Phe Ser Pro Ile Thr Val Ser His Asn Ile
                340                 345                 350
His Ala Gly Thr Gln Leu Ser Pro Gly Gly Trp Asp Ile Ile Pro Gly
            355                 360                 365
Ala Ile Tyr Ser Glu Asp Arg Glu Asn Asn Val Leu Phe Ala Glu Ala
        370                 375                 380
Phe Ile Thr Thr Pro Tyr Val Phe Val Met Gln Lys Ala Pro Asp Ser
385                 390                 395                 400
Glu Gln Thr Leu Lys Lys Gly Met Lys Val Ala Ile Pro Tyr Tyr Tyr
                    405                 410                 415
Glu Leu His Ser Gln Leu Lys Glu Met Tyr Pro Glu Val Glu Trp Ile
                420                 425                 430
Gln Val Asp Asn Ala Ser Ala Ala Phe His Lys Val Lys Glu Gly Glu
            435                 440                 445
Leu Asp Ala Leu Val Ala Thr Gln Leu Asn Ser Arg Tyr Met Ile Asp
        450                 455                 460
His Tyr Tyr Pro Asn Glu Leu Tyr His Phe Leu Ile Pro Gly Val Pro
465                 470                 475                 480
Asn Ala Ser Leu Ser Phe Ala Phe Pro Arg Gly Glu Pro Glu Leu Lys
                    485                 490                 495
Asp Ile Ile Asn Lys Ala Leu Asn Ala Ile Pro Pro Ser Glu Val Leu
                500                 505                 510
Arg Leu Thr Glu Lys Trp Ile Lys Met Pro Asn Val Thr Ile Asp Thr
            515                 520                 525
Trp Asp Leu Tyr Ser Glu Gln Phe Tyr Ile Val Thr Thr Leu Ser Val
        530                 535                 540
Leu Leu Val Gly Ser Ser Leu Leu Trp Gly Phe Tyr Leu Leu Arg Ser
545                 550                 555                 560
Val Arg Arg Arg Lys Val Ile Gln Gly Asp Leu Glu Asn Gln Ile Ser
                    565                 570                 575
Phe Arg Lys Ala Leu Ser Asp Ser Leu Pro Asn Pro Thr Tyr Val Val
                580                 585                 590
Asn Trp Gln Gly Asn Val Ile Ser His Asn Ser Ala Phe Glu His Tyr
            595                 600                 605
Phe Thr Ala Asp Tyr Tyr Lys Asn Ala Met Leu Pro Leu Glu Asn Ser
        610                 615                 620
Asp Ser Pro Phe Lys Asp Val Phe Ser Asn Ala His Glu Val Thr Ala
625                 630                 635                 640
Glu Thr Lys Glu Asn Arg Thr Ile Tyr Thr Gln Val Phe Glu Ile Asp
                    645                 650                 655
Asn Gly Ile Glu Lys Arg Cys Ile Asn His Trp His Thr Leu Cys Asn
                660                 665                 670
Leu Pro Ala Ser Asp Asn Ala Val Tyr Ile Cys Gly Trp Gln Asp Ile
            675                 680                 685
Thr Glu Thr Arg Asp Leu Ile Asn Ala Leu Glu Val Glu Lys Asn Lys
```

```
                690             695             700
Ala Ile Lys Ala Thr Val Ala Lys Ser Gln Phe Leu Ala Thr Met Ser
705             710             715             720

His Glu Ile Arg Thr Pro Ile Ser Ser Ile Met Gly Phe Leu Glu Leu
                725             730             735

Leu Ser Gly Ser Gly Leu Ser Lys Glu Gln Arg Val Glu Ala Ile Ser
            740             745             750

Leu Ala Tyr Ala Thr Gly Gln Ser Leu Leu Gly Leu Ile Gly Glu Ile
        755             760             765

Leu Asp Val Asp Lys Ile Glu Ser Gly Asn Tyr Gln Leu Gln Pro Gln
    770             775             780

Trp Val Asp Ile Pro Thr Leu Val Gln Asn Thr Cys His Ser Phe Gly
785             790             795             800

Ala Ile Ala Ala Ser Lys Ser Ile Ala Leu Ser Cys Ser Ser Thr Phe
                805             810             815

Pro Glu His Tyr Leu Val Lys Ile Asp Pro Gln Ala Phe Lys Gln Val
                820             825             830

Leu Ser Asn Leu Leu Ser Asn Ala Leu Lys Phe Thr Thr Glu Gly Ala
            835             840             845

Val Lys Ile Thr Thr Ser Leu Gly His Ile Asp Asp Asn His Ala Val
850             855             860

Ile Lys Met Thr Ile Met Asp Ser Gly Ser Gly Leu Ser Gln Glu Glu
865             870             875             880

Gln Gln Gln Leu Phe Lys Arg Tyr Ser Gln Thr Ser Ala Gly Arg Gln
                885             890             895

Gln Thr Gly Ser Gly Leu Gly Leu Met Ile Cys Lys Glu Leu Ile Lys
            900             905             910

Asn Met Gln Gly Asp Leu Ser Leu Glu Ser His Pro Gly Ile Gly Thr
        915             920             925

Thr Phe Thr Ile Thr Ile Pro Val Glu Ile Ser Gln Gln Val Ala Thr
    930             935             940

Val Glu Ala Lys Ala Glu Gln Pro Ile Thr Leu Pro Glu Lys Leu Ser
945             950             955             960

Ile Leu Ile Ala Asp Asp His Pro Thr Asn Arg Leu Leu Leu Lys Arg
                965             970             975

Gln Leu Asn Leu Leu Gly Tyr Asp Val Asp Glu Ala Thr Asp Gly Val
            980             985             990

Gln Ala Leu His Lys Val Ser Met Gln His Tyr Asp Leu Leu Ile Thr
        995             1000            1005

Asp Val Asn Met Pro Asn Met Asp Gly Phe Glu Leu Thr Arg Lys
    1010            1015            1020

Leu Arg Glu Gln Asn Ser Ser Leu Pro Ile Trp Gly Leu Thr Ala
    1025            1030            1035

Asn Ala Gln Ala Asn Glu Arg Glu Lys Gly Leu Ser Cys Gly Met
    1040            1045            1050

Asn Leu Cys Leu Phe Lys Pro Leu Thr Leu Asp Val Leu Lys Thr
    1055            1060            1065

His Leu Ser Gln Leu His Gln Val Ala His Ile Ala Pro Gln Tyr
    1070            1075            1080

Arg His Leu Asp Ile Glu Ala Leu Lys Asn Asn Thr Ala Asn Asp
    1085            1090            1095

Leu Gln Leu Met Gln Glu Ile Leu Met Thr Phe Gln His Glu Thr
    1100            1105            1110
```

| His | Lys | Asp | Leu | Pro | Ala | Ala | Phe | Gln | Ala | Leu | Glu | Ala | Gly | Asp |
|  | 1115 |  |  |  | 1120 |  |  |  | 1125 |  |  |  |  |  |

| Asn | Arg | Thr | Phe | His | Gln | Cys | Ile | His | Arg | Ile | His | Gly | Ala | Ala |
|  | 1130 |  |  |  | 1135 |  |  |  | 1140 |  |  |  |  |  |

| Asn | Ile | Leu | Asn | Leu | Gln | Lys | Leu | Ile | Asn | Ile | Ser | His | Gln | Leu |
|  | 1145 |  |  |  | 1150 |  |  |  | 1155 |  |  |  |  |  |

| Glu | Ile | Thr | Pro | Val | Ser | Asp | Asp | Ser | Lys | Pro | Glu | Ile | Leu | Gln |
|  | 1160 |  |  |  | 1165 |  |  |  | 1170 |  |  |  |  |  |

| Leu | Leu | Asn | Ser | Val | Lys | Glu | His | Ile | Ala | Glu | Leu | Asp | Gln | Glu |
|  | 1175 |  |  |  | 1180 |  |  |  | 1185 |  |  |  |  |  |

| Ile | Ala | Val | Phe | Cys | Gln | Lys | Asn | Asp |
|  | 1190 |  |  |  | 1195 |  |  |  |

<210> SEQ ID NO 27
<211> LENGTH: 528
<212> TYPE: DNA
<213> ORGANISM: Escherichia coli
<220> FEATURE:
<221> NAME/KEY: CDS
<222> LOCATION: (1)..(528)

<400> SEQUENCE: 27

```
atg att ttt ctc atg acg aaa gat tct ttt ctt tta cag ggc ttt tgg      48
Met Ile Phe Leu Met Thr Lys Asp Ser Phe Leu Leu Gln Gly Phe Trp
1               5                   10                  15 cag ttg aaa gat aat cac gaa atg ata aaa atc aat tcc ctg tca gag      96
Gln Leu Lys Asp Asn His Glu Met Ile Lys Ile Asn Ser Leu Ser Glu
            20                  25                  30 atc aaa aaa gta ggc aat aaa ccc ttc aag gtt atc att gat acc tat     144
Ile Lys Lys Val Gly Asn Lys Pro Phe Lys Val Ile Ile Asp Thr Tyr
        35                  40                  45 cac aat cat atc ctt gat gaa gaa gcg att aaa ttt ctg gag aaa tta     192
His Asn His Ile Leu Asp Glu Glu Ala Ile Lys Phe Leu Glu Lys Leu
    50                  55                  60 gat gcc gag aga att att gtt ttg gca cct tat cac atc agt aaa cta     240
Asp Ala Glu Arg Ile Ile Val Leu Ala Pro Tyr His Ile Ser Lys Leu
65                  70                  75                  80 aaa gct aaa gcg cct att tat ttt gtt agc cgc aaa gaa agt atc aaa     288
Lys Ala Lys Ala Pro Ile Tyr Phe Val Ser Arg Lys Glu Ser Ile Lys
                85                  90                  95 aat ctt ctt gag att act tat ggt aaa cac ttg ccc cat aag aat tca     336
Asn Leu Leu Glu Ile Thr Tyr Gly Lys His Leu Pro His Lys Asn Ser
            100                 105                 110 caa tta tgt ttt tca cat aat cag ttc aaa att atg caa ctg att ctg     384
Gln Leu Cys Phe Ser His Asn Gln Phe Lys Ile Met Gln Leu Ile Leu
        115                 120                 125 aaa aat aaa aat gaa agc aat atc acg tcg acg ctc aat att tcg caa     432
Lys Asn Lys Asn Glu Ser Asn Ile Thr Ser Thr Leu Asn Ile Ser Gln
    130                 135                 140 caa aca tta aag att cag aaa ttc aac att atg tac aag ctg aaa cta     480
Gln Thr Leu Lys Ile Gln Lys Phe Asn Ile Met Tyr Lys Leu Lys Leu
145                 150                 155                 160 aga cgt atg agc gac atc gtc acc ctg ggt atc aca tct tat ttt tag     528
Arg Arg Met Ser Asp Ile Val Thr Leu Gly Ile Thr Ser Tyr Phe
                165                 170                 175
```

<210> SEQ ID NO 28
<211> LENGTH: 175
<212> TYPE: PRT
<213> ORGANISM: Escherichia coli -continued

<400> SEQUENCE: 28

Met Ile Phe Leu Met Thr Lys Asp Ser Phe Leu Leu Gln Gly Phe Trp
1               5                   10                  15

Gln Leu Lys Asp Asn His Glu Met Ile Lys Ile Asn Ser Leu Ser Glu
            20                  25                  30

Ile Lys Lys Val Gly Asn Lys Pro Phe Lys Val Ile Ile Asp Thr Tyr
        35                  40                  45

His Asn His Ile Leu Asp Glu Glu Ala Ile Lys Phe Leu Glu Lys Leu
    50                  55                  60

Asp Ala Glu Arg Ile Ile Val Leu Ala Pro Tyr His Ile Ser Lys Leu
65                  70                  75                  80

Lys Ala Lys Ala Pro Ile Tyr Phe Val Ser Arg Lys Glu Ser Ile Lys
                85                  90                  95

Asn Leu Leu Glu Ile Thr Tyr Gly Lys His Leu Pro His Lys Asn Ser
            100                 105                 110

Gln Leu Cys Phe Ser His Asn Gln Phe Lys Ile Met Gln Leu Ile Leu
        115                 120                 125

Lys Asn Lys Asn Glu Ser Asn Ile Thr Ser Thr Leu Asn Ile Ser Gln
130                 135                 140

Gln Thr Leu Lys Ile Gln Lys Phe Asn Ile Met Tyr Lys Leu Lys Leu
145                 150                 155                 160

Arg Arg Met Ser Asp Ile Val Thr Leu Gly Ile Thr Ser Tyr Phe
                165                 170                 175

<210> SEQ ID NO 29
<211> LENGTH: 762
<212> TYPE: DNA
<213> ORGANISM: Escherichia coli
<220> FEATURE:
<221> NAME/KEY: CDS
<222> LOCATION: (1)..(762)

<400> SEQUENCE: 29

```
atg tcg ctc gtt tgt tct gtt ata ttt att cat cat gcc ttc aac gct      48
Met Ser Leu Val Cys Ser Val Ile Phe Ile His His Ala Phe Asn Ala
1               5                   10                  15 aac att tta gat aaa gat tac gcc ttc tct gac ggc gag atc ctg atg      96
Asn Ile Leu Asp Lys Asp Tyr Ala Phe Ser Asp Gly Glu Ile Leu Met
            20                  25                  30 gta gat aac gct gtt cgt acg cat ttt gaa cct tat gag cgg cat ttt     144
Val Asp Asn Ala Val Arg Thr His Phe Glu Pro Tyr Glu Arg His Phe
        35                  40                  45 aaa gag atc gga ttt act gaa aat acc att aaa aaa tat cta caa tgc     192
Lys Glu Ile Gly Phe Thr Glu Asn Thr Ile Lys Lys Tyr Leu Gln Cys
    50                  55                  60 act aac atc cag aca gtg acg gtg cct gtt cct gcg aag ttt tta cgt     240
Thr Asn Ile Gln Thr Val Thr Val Pro Val Pro Ala Lys Phe Leu Arg
65                  70                  75                  80 gct tca aat gta ccg act gga ttg ctt aat gaa atg att gct tat ctc     288
Ala Ser Asn Val Pro Thr Gly Leu Leu Asn Glu Met Ile Ala Tyr Leu
                85                  90                  95 aac tcg gaa gaa cgc aat cat cat aat ttt tca gaa ctt ttg ctt ttt     336
Asn Ser Glu Glu Arg Asn His His Asn Phe Ser Glu Leu Leu Leu Phe
            100                 105                 110 tct tgc ctg tct att ttt gcc gca tgc aaa ggt ttc att aca cta tta     384
Ser Cys Leu Ser Ile Phe Ala Ala Cys Lys Gly Phe Ile Thr Leu Leu
        115                 120                 125
```

```
act aac ggt gtg cta tcc gtt tct ggg aaa gtg aga aat att gtc aac    432
Thr Asn Gly Val Leu Ser Val Ser Gly Lys Val Arg Asn Ile Val Asn
        130                 135                 140 atg aag ccg gcg cac cca tgg aag ctg aaa gat att tgt gac tgc ctg    480
Met Lys Pro Ala His Pro Trp Lys Leu Lys Asp Ile Cys Asp Cys Leu
145                 150                 155                 160 tac atc agt gaa agc ctg ttg aag aaa aaa ctt aag caa gag caa acg    528
Tyr Ile Ser Glu Ser Leu Leu Lys Lys Lys Leu Lys Gln Glu Gln Thr
                165                 170                 175 aca ttc tca cag att ctt tta gat gca aga atg cag cac gca aaa aat    576
Thr Phe Ser Gln Ile Leu Leu Asp Ala Arg Met Gln His Ala Lys Asn
            180                 185                 190 ttg ata cgc gta gaa ggt tca gtc aat aaa att gcc gaa caa tgt ggt    624
Leu Ile Arg Val Glu Gly Ser Val Asn Lys Ile Ala Glu Gln Cys Gly
        195                 200                 205 tat gcc agt aca tct tat ttt att tat gcg ttc cgc aaa cat ttc ggc    672
Tyr Ala Ser Thr Ser Tyr Phe Ile Tyr Ala Phe Arg Lys His Phe Gly
    210                 215                 220 aac agt ccg aag aga gtt tct aag gag tac cgt tgt caa agt cac acg    720
Asn Ser Pro Lys Arg Val Ser Lys Glu Tyr Arg Cys Gln Ser His Thr
225                 230                 235                 240 ggt atg aat acg ggc aac acg atg aat gct tta gct att tga           762
Gly Met Asn Thr Gly Asn Thr Met Asn Ala Leu Ala Ile
                245                 250
```

<210> SEQ ID NO 30
<211> LENGTH: 253
<212> TYPE: PRT
<213> ORGANISM: Escherichia coli

<400> SEQUENCE: 30

```
Met Ser Leu Val Cys Ser Val Ile Phe Ile His His Ala Phe Asn Ala
1               5                   10                  15

Asn Ile Leu Asp Lys Asp Tyr Ala Phe Ser Asp Gly Glu Ile Leu Met
            20                  25                  30

Val Asp Asn Ala Val Arg Thr His Phe Glu Pro Tyr Glu Arg His Phe
        35                  40                  45

Lys Glu Ile Gly Phe Thr Glu Asn Thr Ile Lys Lys Tyr Leu Gln Cys
    50                  55                  60

Thr Asn Ile Gln Thr Val Thr Val Pro Val Pro Ala Lys Phe Leu Arg
65                  70                  75                  80

Ala Ser Asn Val Pro Thr Gly Leu Leu Asn Glu Met Ile Ala Tyr Leu
                85                  90                  95

Asn Ser Glu Glu Arg Asn His His Asn Phe Ser Glu Leu Leu Leu Phe
            100                 105                 110

Ser Cys Leu Ser Ile Phe Ala Ala Cys Lys Gly Phe Ile Thr Leu Leu
        115                 120                 125

Thr Asn Gly Val Leu Ser Val Ser Gly Lys Val Arg Asn Ile Val Asn
    130                 135                 140

Met Lys Pro Ala His Pro Trp Lys Leu Lys Asp Ile Cys Asp Cys Leu
145                 150                 155                 160

Tyr Ile Ser Glu Ser Leu Leu Lys Lys Lys Leu Lys Gln Glu Gln Thr
                165                 170                 175

Thr Phe Ser Gln Ile Leu Leu Asp Ala Arg Met Gln His Ala Lys Asn
            180                 185                 190

Leu Ile Arg Val Glu Gly Ser Val Asn Lys Ile Ala Glu Gln Cys Gly
        195                 200                 205
```

```
Tyr Ala Ser Thr Ser Tyr Phe Ile Tyr Ala Phe Arg Lys His Phe Gly
    210                 215                 220

Asn Ser Pro Lys Arg Val Ser Lys Glu Tyr Arg Cys Gln Ser His Thr
225                 230                 235                 240

Gly Met Asn Thr Gly Asn Thr Met Asn Ala Leu Ala Ile
                245                 250

<210> SEQ ID NO 31
<211> LENGTH: 2148
<212> TYPE: DNA
<213> ORGANISM: Escherichia coli
<220> FEATURE:
<221> NAME/KEY: CDS
<222> LOCATION: (1)..(2145)

<400> SEQUENCE: 31 atg aac gtt att gca ata ttg aat cac atg ggg gtt tat ttt aaa gaa      48
Met Asn Val Ile Ala Ile Leu Asn His Met Gly Val Tyr Phe Lys Glu
1               5                   10                  15 gaa ccc atc cgt gaa ctt cat cgc gcg ctt gaa cgt ctg aac ttc cag      96
Glu Pro Ile Arg Glu Leu His Arg Ala Leu Glu Arg Leu Asn Phe Gln
            20                  25                  30 att gtt tac ccg aac gac cgt gac gac tta tta aaa ctg atc gaa aac     144
Ile Val Tyr Pro Asn Asp Arg Asp Asp Leu Leu Lys Leu Ile Glu Asn
        35                  40                  45 aat gcg cgt ctg tgc ggc gtt att ttt gac tgg gat aaa tat aat ctc     192
Asn Ala Arg Leu Cys Gly Val Ile Phe Asp Trp Asp Lys Tyr Asn Leu
    50                  55                  60 gag ctg tgc gaa gaa att agc aaa atg aac gag aac ctg ccg ttg tac     240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg     288
Ala Phe Ala Asn Thr Tyr Ser Thr Leu Asp Val Ser Leu Asn Asp Leu
                85                  90                  95 cgt tta cag att agc ttc ttt gaa tat gcg ctg ggt gct gct gaa gat     336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att     384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa     432
Leu Pro Pro Leu Thr Lys Ala Leu Phe Lys Tyr Val Arg Glu Gly Lys
    130                 135                 140 tat act ttc tgt act cct ggt cac atg ggc ggt act gca ttc cag aaa     480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg     528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat     576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt     624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac     672
Asn Ala Asp Arg Ser Tyr Met Val Thr Asn Gly Thr Ser Thr Ala Asn
    210                 215                 220 aaa att gtt ggt atg tac tct gct cca gca ggc agc acc att ctg att     720
Lys Ile Val Gly Met Tyr Ser Ala Pro Ala Gly Ser Thr Ile Leu Ile
225                 230                 235                 240
```

| | | |
|---|---|---|
| gac cgt aac tgc cac aaa tcg ctg acc cac ctg atg atg agc gat<br>Asp Arg Asn Cys His Lys Ser Leu Thr His Leu Met Met Ser Asp<br>245 250 255 | | 768 |
| gtt acg cca atc tat ttc cgc ccg acc cgt aac gct tac ggt att ctt<br>Val Thr Pro Ile Tyr Phe Arg Pro Thr Arg Asn Ala Tyr Gly Ile Leu<br>260 265 270 | | 816 |
| ggt ggt atc cca cag agt gaa ttc cag cac gct acc att gct aag cgc<br>Gly Gly Ile Pro Gln Ser Glu Phe Gln His Ala Thr Ile Ala Lys Arg<br>275 280 285 | | 864 |
| gtg aaa gaa aca cca aac gca acc tgg ccg gta cat gct gta att acc<br>Val Lys Glu Thr Pro Asn Ala Thr Trp Pro Val His Ala Val Ile Thr<br>290 295 300 | | 912 |
| aac tct acc tat gat ggt ctg ctg tac aac acc gac ttc atc aag aaa<br>Asn Ser Thr Tyr Asp Gly Leu Leu Tyr Asn Thr Asp Phe Ile Lys Lys<br>305 310 315 320 | | 960 |
| aca ctg gat gtg aaa tcc atc cac ttt gac tcc gcg tgg gtg cct tac<br>Thr Leu Asp Val Lys Ser Ile His Phe Asp Ser Ala Trp Val Pro Tyr<br>325 330 335 | | 1008 |
| acc aac ttc tca ccg att tac gaa ggt aaa tgc ggt atg agc ggt ggc<br>Thr Asn Phe Ser Pro Ile Tyr Glu Gly Lys Cys Gly Met Ser Gly Gly<br>340 345 350 | | 1056 |
| cgt gta gaa ggg aaa gtg att tac gaa acc cag tcc act cac aaa ctg<br>Arg Val Glu Gly Lys Val Ile Tyr Glu Thr Gln Ser Thr His Lys Leu<br>355 360 365 | | 1104 |
| ctg gcg gcg ttc tct cag gct tcc atg atc cac gtt aaa ggt gac gta<br>Leu Ala Ala Phe Ser Gln Ala Ser Met Ile His Val Lys Gly Asp Val<br>370 375 380 | | 1152 |
| aac gaa gaa acc ttt aac gaa gcc tac atg atg cac acc acc act tct<br>Asn Glu Glu Thr Phe Asn Glu Ala Tyr Met Met His Thr Thr Thr Ser<br>385 390 395 400 | | 1200 |
| ccg cac tac ggt atc gtg gcg tcc act gaa acc gct gcg gcg atg atg<br>Pro His Tyr Gly Ile Val Ala Ser Thr Glu Thr Ala Ala Ala Met Met<br>405 410 415 | | 1248 |
| aaa ggc aat gca ggt aag cgt ctg atc aac ggt tct att gaa cgt gcg<br>Lys Gly Asn Ala Gly Lys Arg Leu Ile Asn Gly Ser Ile Glu Arg Ala<br>420 425 430 | | 1296 |
| atc aaa ttc cgt aaa gag atc aaa cgt ctg aga acg gaa tct gat ggc<br>Ile Lys Phe Arg Lys Glu Ile Lys Arg Leu Arg Thr Glu Ser Asp Gly<br>435 440 445 | | 1344 |
| tgg ttc ttt gat gta tgg cag ccg gat cat atc gat acg act gaa tgc<br>Trp Phe Phe Asp Val Trp Gln Pro Asp His Ile Asp Thr Thr Glu Cys<br>450 455 460 | | 1392 |
| tgg ccg ctg cgt tct gac agc acc tgg cac ggc ttc aaa aac atc gat<br>Trp Pro Leu Arg Ser Asp Ser Thr Trp His Gly Phe Lys Asn Ile Asp<br>465 470 475 480 | | 1440 |
| aac gag cac atg tat ctt gac ccg atc aaa gtc acc ctg ctg act ccg<br>Asn Glu His Met Tyr Leu Asp Pro Ile Lys Val Thr Leu Leu Thr Pro<br>485 490 495 | | 1488 |
| ggg atg gaa aaa gac ggc acc atg agc gac ttt ggt att ccg gcc agc<br>Gly Met Glu Lys Asp Gly Thr Met Ser Asp Phe Gly Ile Pro Ala Ser<br>500 505 510 | | 1536 |
| atc gtg gcg aaa tac ctc gac gaa cat ggc atc gtt gtt gag aaa acc<br>Ile Val Ala Lys Tyr Leu Asp Glu His Gly Ile Val Val Glu Lys Thr<br>515 520 525 | | 1584 |
| ggt ccg tat aac ctg ctg ttc ctg ttc agc atc ggt atc gat aag acc<br>Gly Pro Tyr Asn Leu Leu Phe Leu Phe Ser Ile Gly Ile Asp Lys Thr<br>530 535 540 | | 1632 |
| aaa gca ctg agc ctg ctg cgt gct ctg act gac ttt aaa cgt gcg ttc<br>Lys Ala Leu Ser Leu Leu Arg Ala Leu Thr Asp Phe Lys Arg Ala Phe | | 1680 |

```
gac ctg aac ctg cgt gtg aaa aac atg ctg ccg tct ctg tat cgt gaa    1728
Asp Leu Asn Leu Arg Val Lys Asn Met Leu Pro Ser Leu Tyr Arg Glu
            565                 570                 575 gat cct gaa ttc tat gaa aac atg cgt att cag gaa ctg gct cag aat    1776
Asp Pro Glu Phe Tyr Glu Asn Met Arg Ile Gln Glu Leu Ala Gln Asn
        580                 585                 590 atc cac aaa ctg att gtt cac cac aat ctg ccg gat ctg atg tat cgc    1824
Ile His Lys Leu Ile Val His His Asn Leu Pro Asp Leu Met Tyr Arg
    595                 600                 605 gca ttt gaa gtg ctg ccg acg atg gta atg act ccg tat gct gca ttc    1872
Ala Phe Glu Val Leu Pro Thr Met Val Met Thr Pro Tyr Ala Ala Phe
610                 615                 620 cag aaa gag ctg cac ggt atg acc gaa gaa gtt tac ctc gac gaa atg    1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt    1968
Val Gly Arg Ile Asn Ala Asn Met Ile Leu Pro Tyr Pro Pro Gly Val
            645                 650                 655 cct ctg gta atg ccg ggt gaa atg atc acc gaa gaa agc cgt ccg gtt    2016
Pro Leu Val Met Pro Gly Glu Met Ile Thr Glu Glu Ser Arg Pro Val
        660                 665                 670 ctg gag ttc ctg cag atg ctg tgt gaa atc ggc gct cac tat ccg ggc    2064
Leu Glu Phe Leu Gln Met Leu Cys Glu Ile Gly Ala His Tyr Pro Gly
    675                 680                 685 ttt gaa acc gat att cac ggt gca tac cgt cag gct gat ggc cgc tat    2112
Phe Glu Thr Asp Ile His Gly Ala Tyr Arg Gln Ala Asp Gly Arg Tyr
690                 695                 700 acc gtt aag gta ttg aaa gaa gaa agc aaa aaa taa                    2148
Thr Val Lys Val Leu Lys Glu Glu Ser Lys Lys
705                 710                 715

<210> SEQ ID NO 32
<211> LENGTH: 715
<212> TYPE: PRT
<213> ORGANISM: Escherichia coli

<400> SEQUENCE: 32

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160
```

```
Ser Pro Val Gly Ser Leu Phe Tyr Asp Phe Gly Pro Asn Thr Met
            165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
                195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
                275                 280                 285

Val Lys Glu Thr Pro Asn Ala Thr Trp Pro Val His Ala Val Ile Thr
                290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
                340                 345                 350

Arg Val Glu Gly Lys Val Ile Tyr Glu Thr Gln Ser Thr His Lys Leu
                355                 360                 365

Leu Ala Ala Phe Ser Gln Ala Ser Met Ile His Val Lys Gly Asp Val
                370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
                435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
                515                 520                 525

Gly Pro Tyr Asn Leu Leu Phe Leu Phe Ser Ile Gly Ile Asp Lys Thr
                530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575
```

```
Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 33
<211> LENGTH: 2142
<212> TYPE: DNA
<213> ORGANISM: Escherichia coli
<220> FEATURE:
<221> NAME/KEY: CDS
<222> LOCATION: (1)..(2139)

<400> SEQUENCE: 33 atg aac atc att gcc att atg gga ccg cat ggc gtc ttt tat aaa gat        48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag        96
Glu Pro Ile Lys Glu Leu Glu Ser Ala Leu Val Ala Gln Gly Phe Gln
                20                  25                  30 att atc tgg cca caa aac agc gtt gat ttg ctg aaa ttt atc gag cat       144
Ile Ile Trp Pro Gln Asn Ser Val Asp Leu Leu Lys Phe Ile Glu His
            35                  40                  45 aac cct cga att tgc ggc gtg att ttt gac tgg gat gag tac agt ctc       192
Asn Pro Arg Ile Cys Gly Val Ile Phe Asp Trp Asp Glu Tyr Ser Leu
        50                  55                  60 gat tta tgt agc gat atc aat cag ctt aat gaa tat ctc ccg ctt tat       240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg       288
Ala Phe Ile Asn Thr His Ser Thr Met Asp Val Ser Val Gln Asp Met
                85                  90                  95 cgg atg gcg ctc tgg ttt ttt gaa tat gcg ctg ggg cag gcg gaa gat       336
Arg Met Ala Leu Trp Phe Phe Glu Tyr Ala Leu Gly Gln Ala Glu Asp
                100                 105                 110 atc gcc att cgt atg cgt cag tac acc gac gaa tat ctt gat aac att       384
Ile Ala Ile Arg Met Arg Gln Tyr Thr Asp Glu Tyr Leu Asp Asn Ile
            115                 120                 125 aca ccg ccg ttc acg aaa gcc ttg ttt acc tac gtc aaa gag cgg aag       432
Thr Pro Pro Phe Thr Lys Ala Leu Phe Thr Tyr Val Lys Glu Arg Lys
        130                 135                 140 tac acc ttt tgt acg ccg ggg cat atg ggc ggc acc gca tat caa aaa       480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt       528
```

|  |  |  |  |  |  |  |  |  |  |  |  |  |  |  |  |
|---|---|---|---|---|---|---|---|---|---|---|---|---|---|---|---|
| Ser | Pro | Val | Gly | Cys | Leu | Phe | Tyr | Asp | Phe | Gly | Asn | Thr | Leu |  |  |
|  |  |  | 165 |  |  |  | 170 |  |  |  | 175 |  |  |  |  |

| aag | gct | gat | gtc | tct | att | tcg | gtc | acc | gag | ctt | ggt | tcg | ttg | ctc | gac | 576 |
|---|---|---|---|---|---|---|---|---|---|---|---|---|---|---|---|---|
| Lys | Ala | Asp | Val | Ser | Ile | Ser | Val | Thr | Glu | Leu | Gly | Ser | Leu | Leu | Asp |  |
|  |  |  | 180 |  |  |  |  | 185 |  |  |  |  | 190 |  |  |  |

| cac | acc | ggg | cca | cac | ctg | gaa | gcg | gaa | gag | tac | atc | gcg | cgg | act | ttt | 624 |
|---|---|---|---|---|---|---|---|---|---|---|---|---|---|---|---|---|
| His | Thr | Gly | Pro | His | Leu | Glu | Ala | Glu | Glu | Tyr | Ile | Ala | Arg | Thr | Phe |  |
|  |  | 195 |  |  |  |  | 200 |  |  |  |  | 205 |  |  |  |  |

| ggc | gcg | gaa | cag | agt | tat | atc | gtt | acc | aac | gga | aca | tcg | acg | tcg | aac | 672 |
|---|---|---|---|---|---|---|---|---|---|---|---|---|---|---|---|---|
| Gly | Ala | Glu | Gln | Ser | Tyr | Ile | Val | Thr | Asn | Gly | Thr | Ser | Thr | Ser | Asn |  |
|  | 210 |  |  |  |  | 215 |  |  |  |  | 220 |  |  |  |  |  |

| aaa | att | gtg | ggt | atg | tac | gcc | gcg | cca | tcc | ggc | agt | acg | ctg | ttg | atc | 720 |
|---|---|---|---|---|---|---|---|---|---|---|---|---|---|---|---|---|
| Lys | Ile | Val | Gly | Met | Tyr | Ala | Ala | Pro | Ser | Gly | Ser | Thr | Leu | Leu | Ile |  |
| 225 |  |  |  |  | 230 |  |  |  |  | 235 |  |  |  |  | 240 |  |

| gac | cgc | aat | tgt | cat | aaa | tcg | ctg | gcg | cat | ctg | ttg | atg | atg | aac | gat | 768 |
|---|---|---|---|---|---|---|---|---|---|---|---|---|---|---|---|---|
| Asp | Arg | Asn | Cys | His | Lys | Ser | Leu | Ala | His | Leu | Leu | Met | Met | Asn | Asp |  |
|  |  |  |  | 245 |  |  |  |  | 250 |  |  |  |  | 255 |  |  |

| gta | gtg | cca | gtc | tgg | ctg | aaa | ccg | acg | cgt | aat | gcg | ttg | ggg | att | ctt | 816 |
|---|---|---|---|---|---|---|---|---|---|---|---|---|---|---|---|---|
| Val | Val | Pro | Val | Trp | Leu | Lys | Pro | Thr | Arg | Asn | Ala | Leu | Gly | Ile | Leu |  |
|  |  |  | 260 |  |  |  |  | 265 |  |  |  |  | 270 |  |  |  |

| ggt | ggg | atc | ccg | cgc | cgt | gaa | ttt | act | cgc | gac | agc | atc | gaa | gag | aaa | 864 |
|---|---|---|---|---|---|---|---|---|---|---|---|---|---|---|---|---|
| Gly | Gly | Ile | Pro | Arg | Arg | Glu | Phe | Thr | Arg | Asp | Ser | Ile | Glu | Glu | Lys |  |
|  |  | 275 |  |  |  |  | 280 |  |  |  |  | 285 |  |  |  |  |

| gtc | gct | gct | acc | acg | caa | gca | caa | tgg | ccg | gtt | cat | gcg | gtg | atc | acc | 912 |
|---|---|---|---|---|---|---|---|---|---|---|---|---|---|---|---|---|
| Val | Ala | Ala | Thr | Thr | Gln | Ala | Gln | Trp | Pro | Val | His | Ala | Val | Ile | Thr |  |
|  | 290 |  |  |  |  | 295 |  |  |  |  | 300 |  |  |  |  |  |

| aac | tcc | acc | tat | gat | ggc | ttg | ctc | tac | aac | acc | gac | tgg | atc | aaa | cag | 960 |
|---|---|---|---|---|---|---|---|---|---|---|---|---|---|---|---|---|
| Asn | Ser | Thr | Tyr | Asp | Gly | Leu | Leu | Tyr | Asn | Thr | Asp | Trp | Ile | Lys | Gln |  |
| 305 |  |  |  |  | 310 |  |  |  |  | 315 |  |  |  |  | 320 |  |

| acg | ctg | gat | gtc | ccg | tcg | att | cac | ttc | gat | tct | gcc | tgg | gtg | ccg | tac | 1008 |
|---|---|---|---|---|---|---|---|---|---|---|---|---|---|---|---|---|
| Thr | Leu | Asp | Val | Pro | Ser | Ile | His | Phe | Asp | Ser | Ala | Trp | Val | Pro | Tyr |  |
|  |  |  |  | 325 |  |  |  |  | 330 |  |  |  |  | 335 |  |  |

| acc | cat | ttt | cat | ccg | atc | tac | cag | ggt | aaa | agt | ggt | atg | agc | ggc | gag | 1056 |
|---|---|---|---|---|---|---|---|---|---|---|---|---|---|---|---|---|
| Thr | His | Phe | His | Pro | Ile | Tyr | Gln | Gly | Lys | Ser | Gly | Met | Ser | Gly | Glu |  |
|  |  |  | 340 |  |  |  |  | 345 |  |  |  |  | 350 |  |  |  |

| cgt | gtt | gcg | gga | aaa | gtg | atc | ttc | gaa | acg | caa | tcg | acc | cac | aaa | atg | 1104 |
|---|---|---|---|---|---|---|---|---|---|---|---|---|---|---|---|---|
| Arg | Val | Ala | Gly | Lys | Val | Ile | Phe | Glu | Thr | Gln | Ser | Thr | His | Lys | Met |  |
|  | 355 |  |  |  |  | 360 |  |  |  |  | 365 |  |  |  |  |  |

| ctg | gcg | gcg | tta | tcg | cag | gct | tcg | ctg | atc | cac | att | aaa | ggc | gag | tat | 1152 |
|---|---|---|---|---|---|---|---|---|---|---|---|---|---|---|---|---|
| Leu | Ala | Ala | Leu | Ser | Gln | Ala | Ser | Leu | Ile | His | Ile | Lys | Gly | Glu | Tyr |  |
|  | 370 |  |  |  |  | 375 |  |  |  |  | 380 |  |  |  |  |  |

| gac | gaa | gag | gcc | ttt | aac | gaa | gcc | ttt | atg | atg | cat | acc | acc | acc | tcg | 1200 |
|---|---|---|---|---|---|---|---|---|---|---|---|---|---|---|---|---|
| Asp | Glu | Glu | Ala | Phe | Asn | Glu | Ala | Phe | Met | Met | His | Thr | Thr | Thr | Ser |  |
| 385 |  |  |  |  | 390 |  |  |  |  | 395 |  |  |  |  | 400 |  |

| ccc | agt | tat | ccc | att | gtt | gct | tcg | gtt | gag | acg | gcg | gcg | gcg | atg | ctg | 1248 |
|---|---|---|---|---|---|---|---|---|---|---|---|---|---|---|---|---|
| Pro | Ser | Tyr | Pro | Ile | Val | Ala | Ser | Val | Glu | Thr | Ala | Ala | Ala | Met | Leu |  |
|  |  |  |  | 405 |  |  |  |  | 410 |  |  |  |  | 415 |  |  |

| cgt | ggt | aat | ccg | ggc | aaa | cgg | ctg | att | aac | cgt | tca | gta | gaa | cga | gct | 1296 |
|---|---|---|---|---|---|---|---|---|---|---|---|---|---|---|---|---|
| Arg | Gly | Asn | Pro | Gly | Lys | Arg | Leu | Ile | Asn | Arg | Ser | Val | Glu | Arg | Ala |  |
|  |  |  | 420 |  |  |  |  | 425 |  |  |  |  | 430 |  |  |  |

| ctg | cat | ttt | cgc | aaa | gag | gtc | cag | cgg | ctg | cgg | gaa | gag | tct | gac | ggt | 1344 |
|---|---|---|---|---|---|---|---|---|---|---|---|---|---|---|---|---|
| Leu | His | Phe | Arg | Lys | Glu | Val | Gln | Arg | Leu | Arg | Glu | Glu | Ser | Asp | Gly |  |
|  |  | 435 |  |  |  |  | 440 |  |  |  |  | 445 |  |  |  |  |

| tgg | ttt | ttc | gat | atc | tgg | caa | ccg | ccg | cag | gtg | gat | gaa | gcc | gaa | tgc | 1392 |
|---|---|---|---|---|---|---|---|---|---|---|---|---|---|---|---|---|
| Trp | Phe | Phe | Asp | Ile | Trp | Gln | Pro | Pro | Gln | Val | Asp | Glu | Ala | Glu | Cys |  |
|  | 450 |  |  |  |  | 455 |  |  |  |  | 460 |  |  |  |  |  |

| tgg | ccc | gtt | gcg | cct | ggc | gaa | cag | tgg | cac | ggc | ttt | aac | gat | gcg | gat | 1440 |
|---|---|---|---|---|---|---|---|---|---|---|---|---|---|---|---|---|
| Trp | Pro | Val | Ala | Pro | Gly | Glu | Gln | Trp | His | Gly | Phe | Asn | Asp | Ala | Asp |  |
| 465 |  |  |  |  | 470 |  |  |  |  | 475 |  |  |  |  | 480 |  |

```
gcc gat cat atg ttt ctc gat ccg gtt aaa gtc act att ttg aca ccg    1488
Ala Asp His Met Phe Leu Asp Pro Val Lys Val Thr Ile Leu Thr Pro
            485                 490                 495 ggg atg gac gag cag ggc aat atg agc gag gag ggg atc ccg gcg gcg    1536
Gly Met Asp Glu Gln Gly Asn Met Ser Glu Glu Gly Ile Pro Ala Ala
500                 505                 510 ctg gta gca aaa ttc ctc gac gaa cgt ggg atc gta gta gag aaa acc    1584
Leu Val Ala Lys Phe Leu Asp Glu Arg Gly Ile Val Val Glu Lys Thr
            515                 520                 525 ggc cct tat aac ctg ctg ttt ctc ttt agt att ggc atc gat aaa acc    1632
Gly Pro Tyr Asn Leu Leu Phe Leu Phe Ser Ile Gly Ile Asp Lys Thr
        530                 535                 540 aaa gca atg gga tta ttg cgt ggg ttg acg gaa ttc aaa cgc tct tac    1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa    1728
Asp Leu Asn Leu Arg Ile Lys Asn Met Leu Pro Asp Leu Tyr Ala Glu
                565                 570                 575 gat ccc gat ttc tac cgc aat atg cgt att cag gat ctg gca caa ggg    1776
Asp Pro Asp Phe Tyr Arg Asn Met Arg Ile Gln Asp Leu Ala Gln Gly
            580                 585                 590 atc cat aag ctg att cgt aaa cac gat ctt ccc ggt ttg atg ttg cgg    1824
Ile His Lys Leu Ile Arg Lys His Asp Leu Pro Gly Leu Met Leu Arg
        595                 600                 605 gca ttc gat act ttg ccg gag atg atc atg acg cca cat cag gca tgg    1872
Ala Phe Asp Thr Leu Pro Glu Met Ile Met Thr Pro His Gln Ala Trp
    610                 615                 620 caa cga caa att aaa ggc gaa gta gaa acc att gcg ctg gaa caa ctg    1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta    1968
Val Gly Arg Val Ser Ala Asn Met Ile Leu Pro Tyr Pro Pro Gly Val
                645                 650                 655 ccg ctg ttg atg cct gga gaa atg ctg acc aaa gag agc cgc aca gta    2016
Pro Leu Leu Met Pro Gly Glu Met Leu Thr Lys Glu Ser Arg Thr Val
            660                 665                 670 ctc gat ttt cta ctg atg ctt tgt tcc gtc ggg caa cat tac ccc ggt    2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac    2112
Phe Glu Thr Asp Ile His Gly Ala Lys Gln Asp Glu Asp Gly Val Tyr
    690                 695                 700 cgc gta cga gtc cta aaa atg gcg gga taa                             2142
Arg Val Arg Val Leu Lys Met Ala Gly
705                 710
```

<210> SEQ ID NO 34
<211> LENGTH: 713
<212> TYPE: PRT
<213> ORGANISM: Escherichia coli

<400> SEQUENCE: 34

```
Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60
```

-continued

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
            115                 120                 125

Thr Pro Pro Phe Thr Lys Ala Leu Phe Thr Tyr Val Lys Glu Arg Lys
130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
            195                 200                 205

Gly Ala Glu Gln Ser Tyr Ile Val Thr Asn Gly Thr Ser Thr Ser Asn
210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
            275                 280                 285

Val Ala Ala Thr Thr Gln Ala Gln Trp Pro Val His Ala Val Ile Thr
290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
            355                 360                 365

Leu Ala Ala Leu Ser Gln Ala Ser Leu Ile His Ile Lys Gly Glu Tyr
370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
            435                 440                 445

Trp Phe Phe Asp Ile Trp Gln Pro Pro Gln Val Asp Glu Ala Glu Cys
450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
            485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
            565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
            595                 600                 605

Ala Phe Asp Thr Leu Pro Glu Met Ile Met Thr Pro His Gln Ala Trp
            610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
            645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
            675                 680                 685

Phe Glu Thr Asp Ile His Gly Ala Lys Gln Asp Glu Asp Gly Val Tyr
            690                 695                 700

Arg Val Arg Val Leu Lys Met Ala Gly
705                 710

<210> SEQ ID NO 35
<211> LENGTH: 54
<212> TYPE: DNA
<213> ORGANISM: Artificial
<220> FEATURE:
<223> OTHER INFORMATION: 5'-primer for cadA

<400> SEQUENCE: 35
tttgctttct tctttcaata ccttaacggt atagcgtgaa gcctgctttt ttat          54

<210> SEQ ID NO 36
<211> LENGTH: 54
<212> TYPE: DNA
<213> ORGANISM: Artificial
<220> FEATURE:
<223> OTHER INFORMATION: 3'-primer for cadA

<400> SEQUENCE: 36
agatatgact atgaacgtta ttgcaatatt gaatcacgct caagttagta taaa          54

<210> SEQ ID NO 37
<211> LENGTH: 54
<212> TYPE: DNA
<213> ORGANISM: Artificial
<220> FEATURE:
<223> OTHER INFORMATION: 5'-primer for ldc

<400> SEQUENCE: 37

```
ggaggaacac atgaacatca ttgccattat gggacctgaa gcctgctttt ttat          54
```

<210> SEQ ID NO 38
<211> LENGTH: 53
<212> TYPE: DNA
<213> ORGANISM: Artificial
<220> FEATURE:
<223> OTHER INFORMATION: 3'-primer for ldc

<400> SEQUENCE: 38

```
cgccattttt aggactcgta cgcggtaaac gccgtccgtc aagttagtat aaa           53
```